US009493835B2

(12) United States Patent
Reis, Jr. et al.

(10) Patent No.: US 9,493,835 B2
(45) Date of Patent: *Nov. 15, 2016

(54) SINGLE PROBE, MULTIPLE TEMPERATURE, NUCLEIC ACID DETECTION METHODS, KITS, AND COMPOSITIONS

(75) Inventors: Arthur H. Reis, Jr., Arlington, MA (US); Lawrence J. Wangh, Auburndale, MA (US); Kenneth Pierce, Natick, MA (US)

(73) Assignee: Brandeis University, Waltham, MA (US)

( * ) Notice: Subject to any disclaimer, the term of this patent is extended or adjusted under 35 U.S.C. 154(b) by 893 days.

This patent is subject to a terminal disclaimer.

(21) Appl. No.: 13/389,921

(22) PCT Filed: Aug. 11, 2010

(86) PCT No.: PCT/US2010/045199
§ 371 (c)(1),
(2), (4) Date: Apr. 24, 2012

(87) PCT Pub. No.: WO2011/019837
PCT Pub. Date: Feb. 17, 2011

(65) Prior Publication Data
US 2012/0202203 A1  Aug. 9, 2012

Related U.S. Application Data

(60) Provisional application No. 61/232,999, filed on Aug. 11, 2009.

(51) Int. Cl.
*C12Q 1/68* (2006.01)
*C12P 19/34* (2006.01)

(52) U.S. Cl.
CPC ............ *C12Q 1/6883* (2013.01); *C12Q 1/689* (2013.01); *C12Q 1/6844* (2013.01); *C12Q 1/6858* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,066,584 | A | 11/1991 | Gyllensten et al. |
| 7,198,897 | B2 | 4/2007 | Wangh et al. |
| 2005/0019893 | A1* | 1/2005 | Huletsky et al. ......... 435/252.3 |
| 2006/0177841 | A1* | 8/2006 | Wangh et al. .................... 435/6 |
| 2007/0082340 | A1 | 4/2007 | Huletsky et al. |

FOREIGN PATENT DOCUMENTS

| WO | 2006/044994 | 4/2006 |
| WO | 2008/011004 | 1/2008 |

OTHER PUBLICATIONS

Sanchez, JA. et al. Two-temperature LATE-PCR endpoint genotyping. BMC Biotechnology, vol. 6(44), p. 1-14, 2006.*
Allawi & Santalucia, "Thermodynamics and NMR of internal G.T mismatches in DNA," Biochemistry,1997, 36 (34):10581-10594.
Ausubel, Current Protocols in Molecular Biology, 1988, Chapter 15: The Polymerase Chain Reaction.
Boye et al. "A new multiplex peR for easy screening of methicillin-resistant *Staphylococcus aureus* SCCmec types I-V" Clin Microbiol Infect, 2007, 13(7): 725-727.
Cuny et al. "PCR for the identification of methicillin-resistant *Staphylococcus aureus* (MRSA) strains using a single primer pair specific for SCCmec elements and the neighbouring chromosome-borne orfX," Clin Microbiol Infect, 2005, 11: 834-837.
Gyllensten et al. "Generation of single-stranded DNA by the polymerase chain reaction and its application to direct sequencing of the HLA-DQA locus," Proc Natl Acad Sci USA, 1988, 85: 7652-7656.
Huletsky et al. "New real-time PCR assay for rapid detection of methicillin-resistant *Staphylococcus aureus* directly from specimens containing a mixture of *Staphylococci*" J Clin Microbiol, 2004, 42(5):1875-1884.
International Search Report and Written Opinion for International Application No. PCT/US10/45199, mailed Oct. 28, 2010.
Kondo et al. "Combination of multiplex PCRs for *Staphylococcal* cassette chromosome mec type assignment: rapid identification system for mec, ccr, and major differences in junkyard regions," Antimicrob Agents Chemother, 2007, 264-274.
Kostrikis et al. "Spectral genotyping of human alleles," Science, 1998, 279: 1228-1229.
Le Novere, "Melting, computing the melting temperature of nucleic acid duplex," Bioinformatics, 2001, 17: 1226-1227.
Lopez-Crapez, "A homogeneous europium cryptate-based assay for the diagnosis of mutations by time-resolved fluorescence resonance energy transfer," Nucl Acids Res, 2001, 29: e70.
Marras et al. "Multiplex detection of single-nucleotide variations using molecular beacons," Genet Anal, 1999, 14: 151-156.
Pierce et al. "Linear-After-The-Exponential (LATE)-PCR: primer design criteria for high yields of specific single-stranded DNA and improved real-time detection," Proc Natl Acad Sci USA, 2005, 102(24): 8609-8614.
Poddar et al. "Symmetric vs asymmetric PCR and molecular beacon probe in the detection of a target gene of adenovirus," Mol Cell Probes, 2000, 14: 25-32.
Sanchez et al. "Two-temperature LATE-PCR endpoint genotyping" BMC Biotechnol, 2006, 6(44): 1-14.

(Continued)

*Primary Examiner* — Prabha Chunduru
*Assistant Examiner* — Suryaprabha Chunduru
(74) *Attorney, Agent, or Firm* — Foley Hoag LLP

(57) ABSTRACT

Provided herein are methods, kits, and compositions related to nucleic acid detection assays that allow discrimination of multiple target sequences with a single probe. In particular, provided herein are methods kits, and compositions that include single-probe target sequence discrimination where different target amplicons may have identical probe hybridization sequences by employing multiple temperature endpoint signal probe detection. Also provided herein are methods, kits, and compositions for distinguishing between two or more target amplicons using multiple-temperature endpoint probe detection. In certain embodiments, asymmetric PCR amplification methods are employed (e.g., LATE-PCR amplification).

4 Claims, 40 Drawing Sheets

(56) References Cited

OTHER PUBLICATIONS

Selvin, "[13]Fluorescence resonance energy transfer," Methods Enyzmol, 1995, 246: 300-334.

Stryer, "Fluorescence energy transfer as a spectroscopic ruler," Ann Rev Biochem, 1978, 47:819-846.

Supplemental European Search Report for European Patent Application No. 10808708, mailed Mar. 15, 2013.

Tijssen, Hybridization with Nucleic Acid Probes, Part 1: Theory and Nucleic Acid Preparation, 1993, Elsevier, Table of Contents Only.

Tyagi et al. "Molecular beacons: probes that fluoresce upon hybridization," Nat Biotechnol, 1996, 14: 303-308.

Tyagi et al. "Multicolor molecular beacons for allele discrimination," Nat Biotechnol, 1998, 16: 49-53.

\* cited by examiner

A.

B.

FIGURE 2B-C
B.
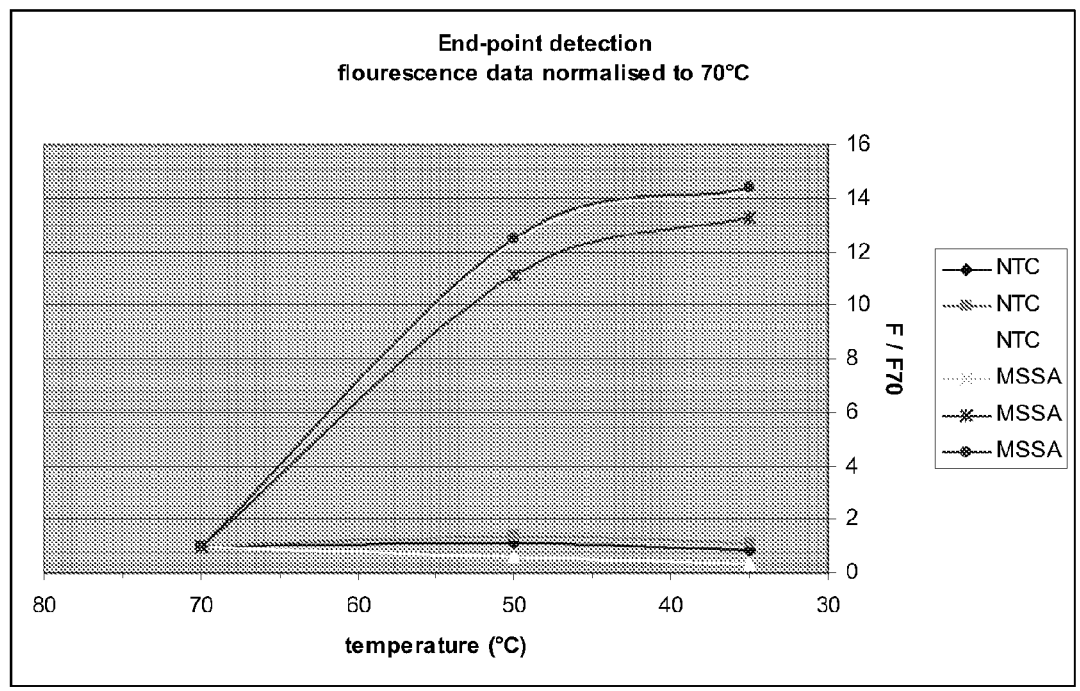
C.
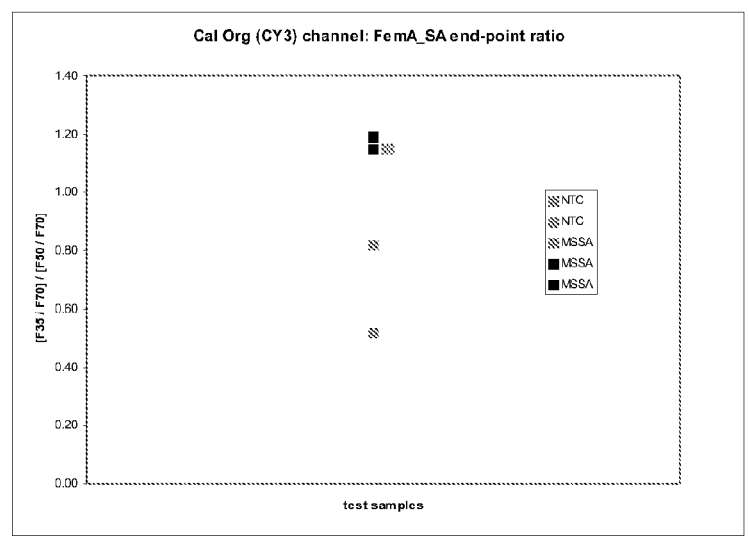

FIGURE 3B-C
B.
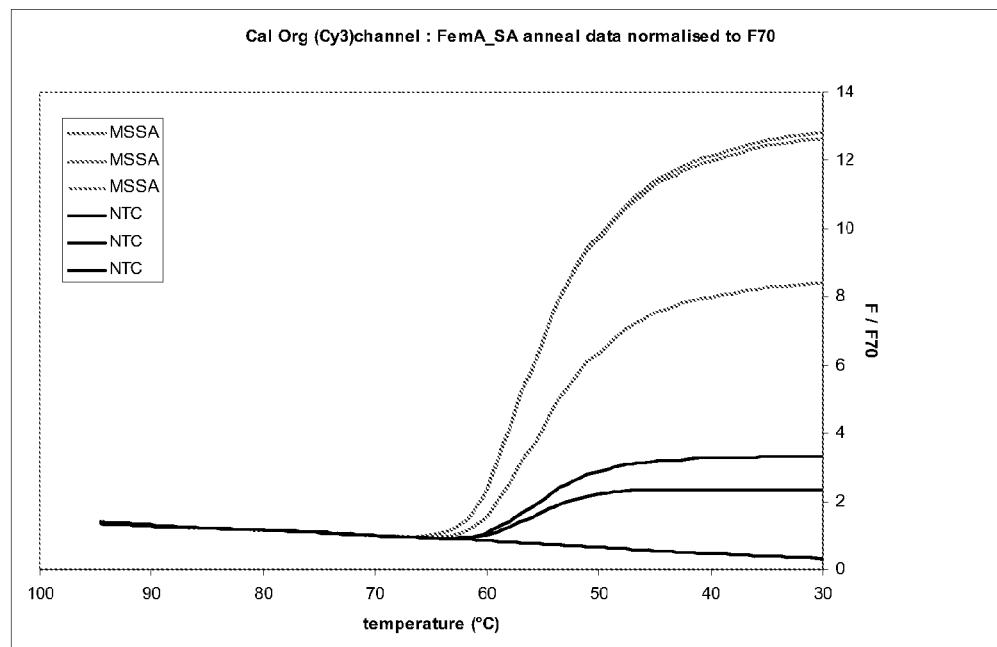
C.
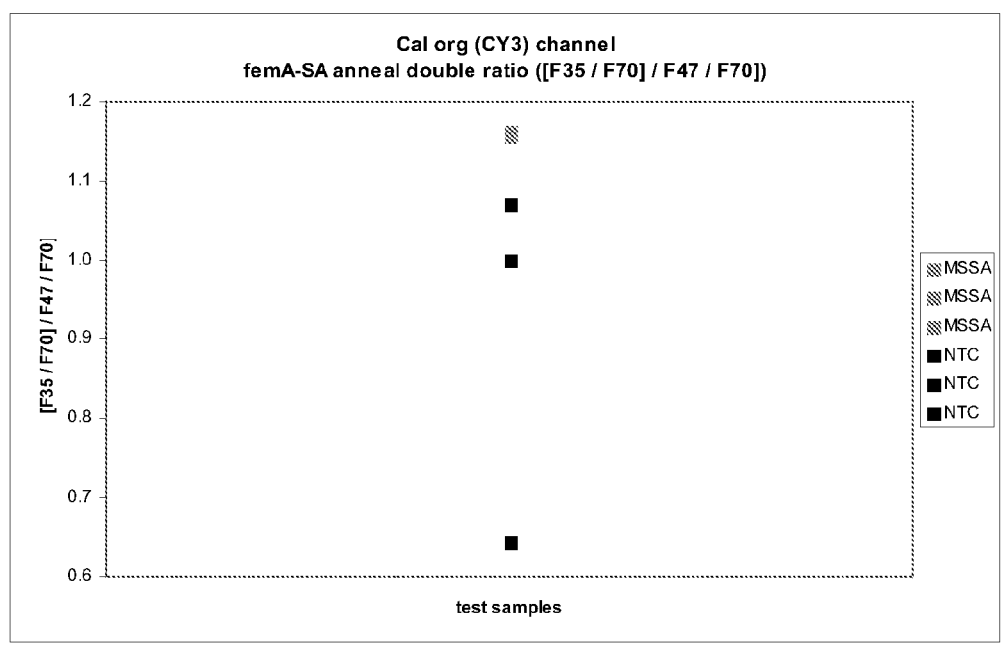

A.

B.

C.

A.

B.

C.

A.

B.

C.

A.

B.

A.

B.

C.

A.

B.

C.

FIGURES 20A-B
A.
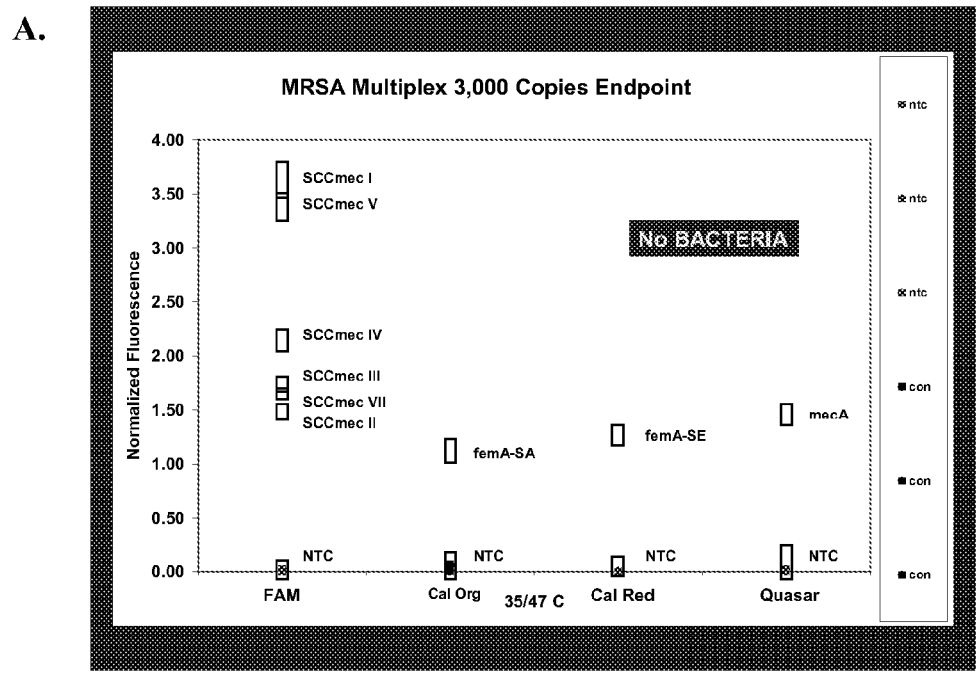
B.
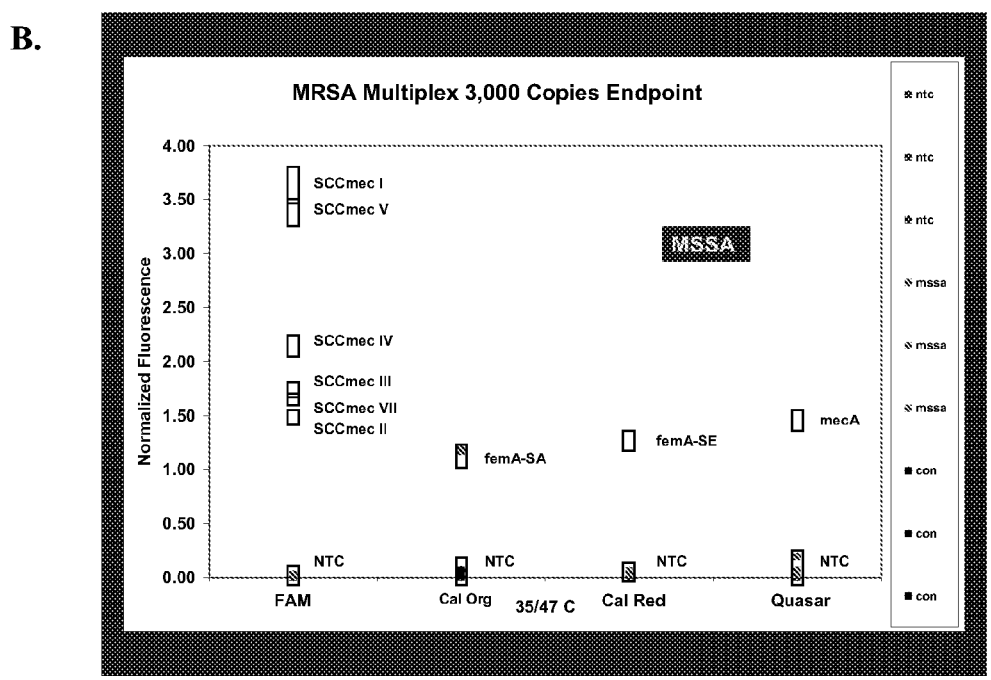

FIGURES 20C-D
C.
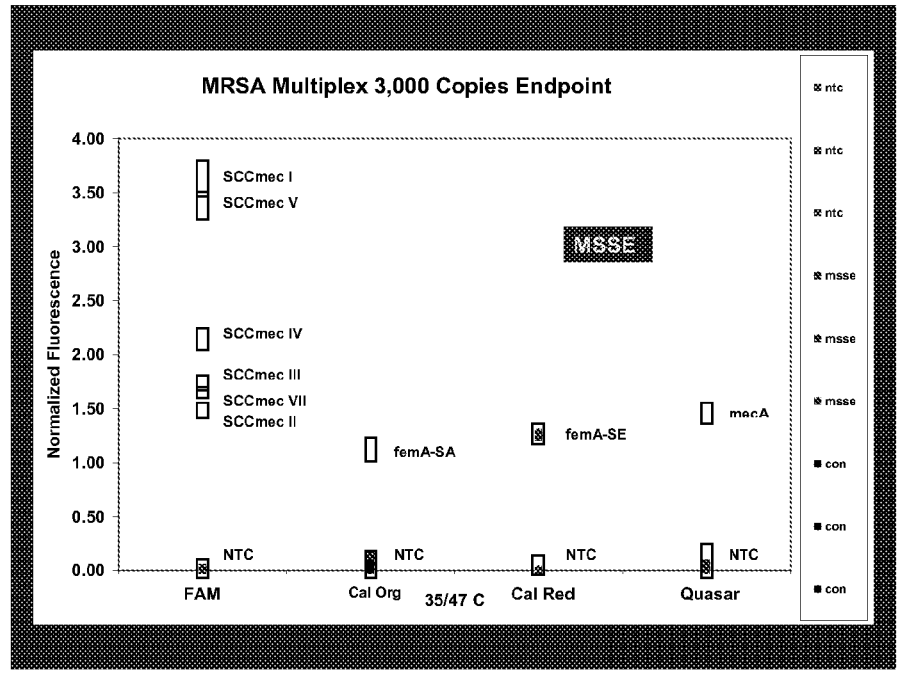
D.
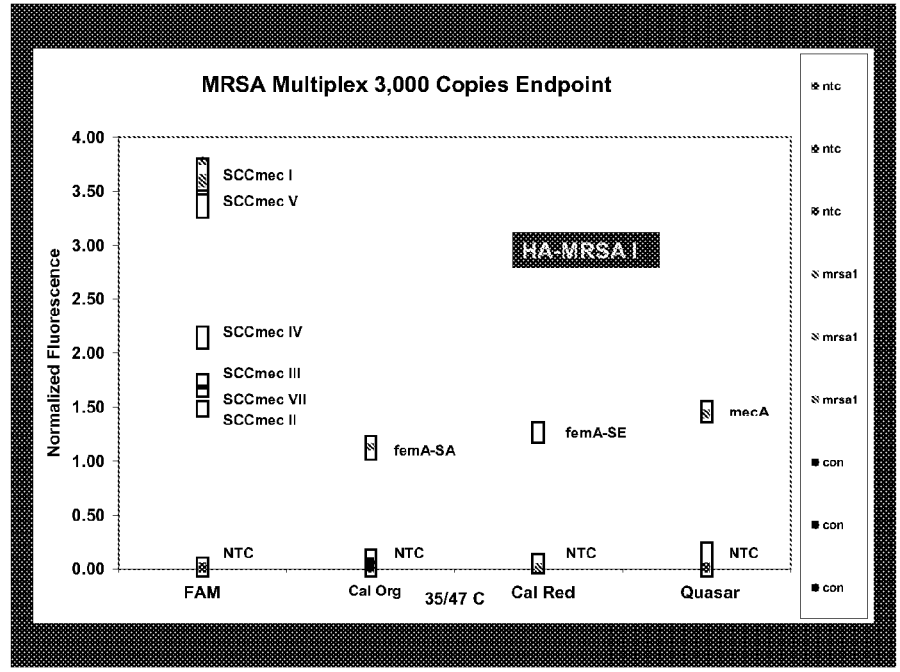

FIGURES 20E-F
E.
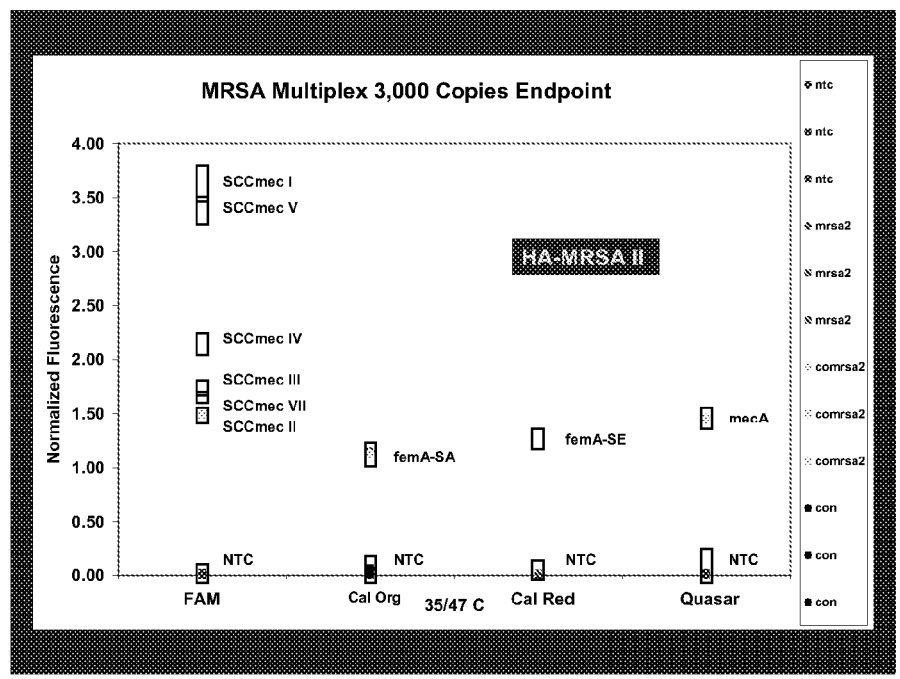
F.
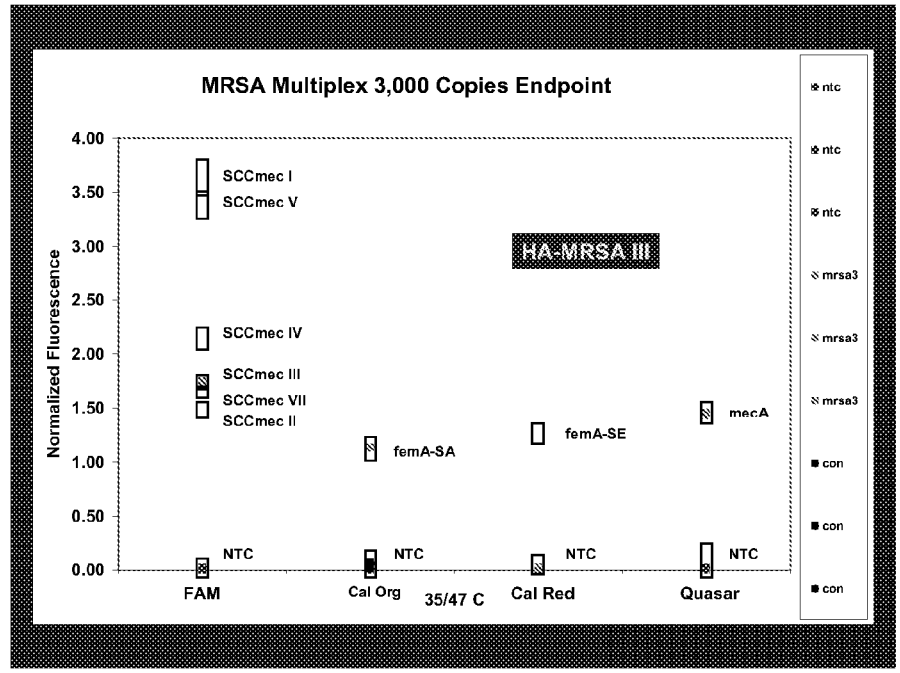

FIGURES 20G-H
G.
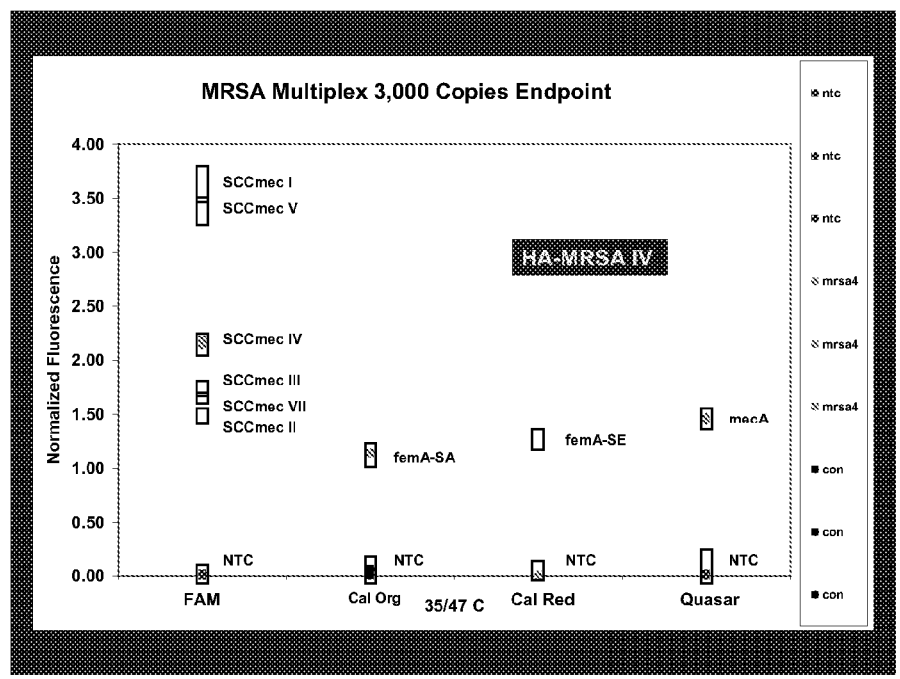
H.
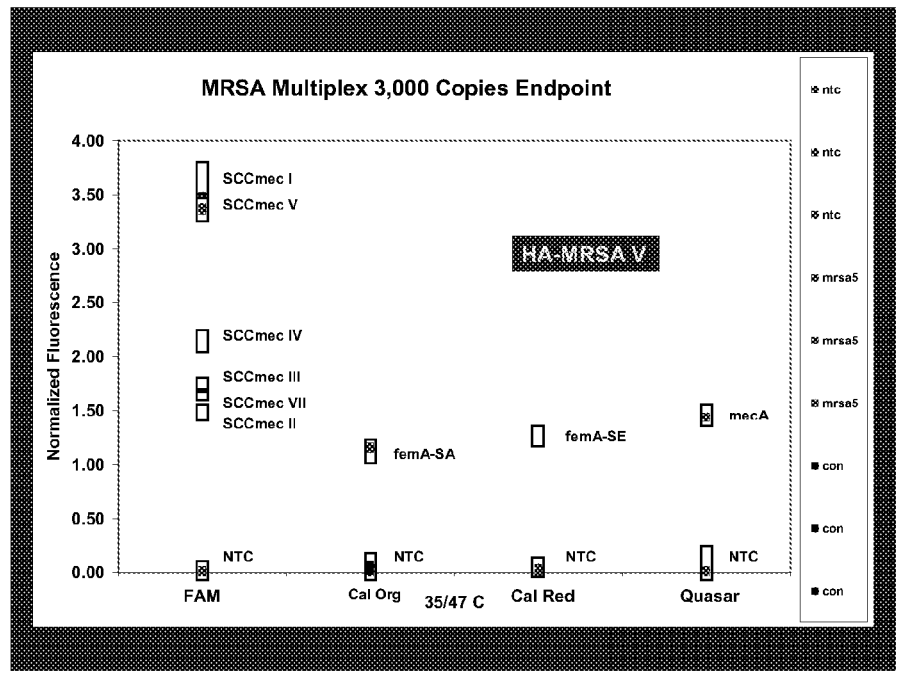

FIGURES 20I-J
I.
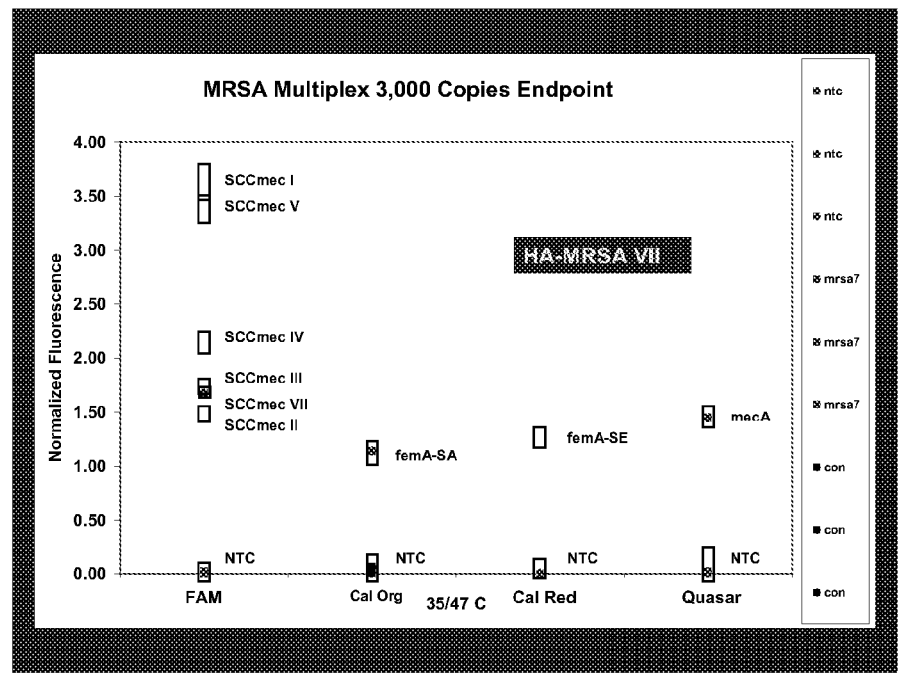
J.
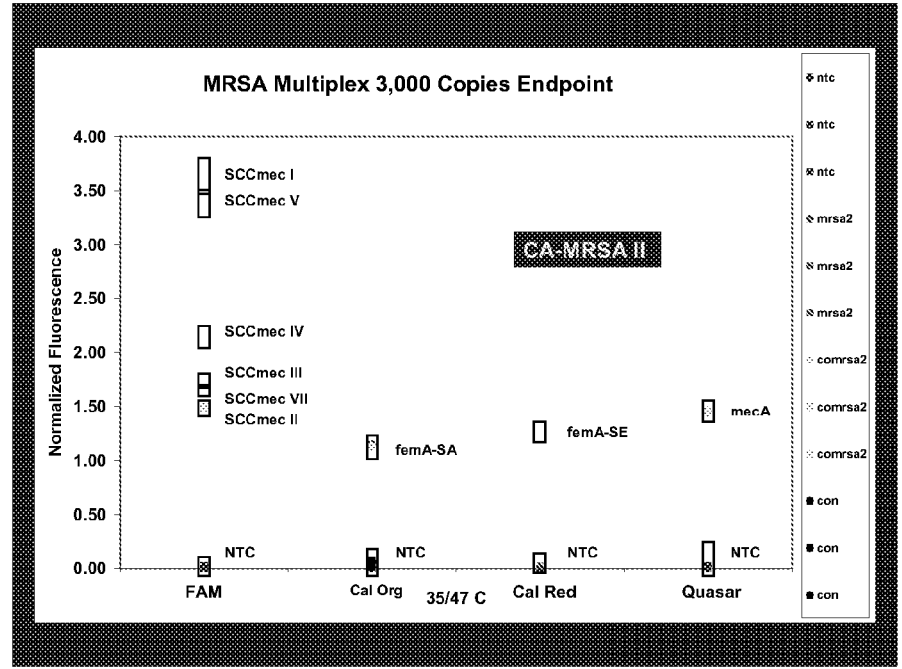

FIGURES 21A-B
A.
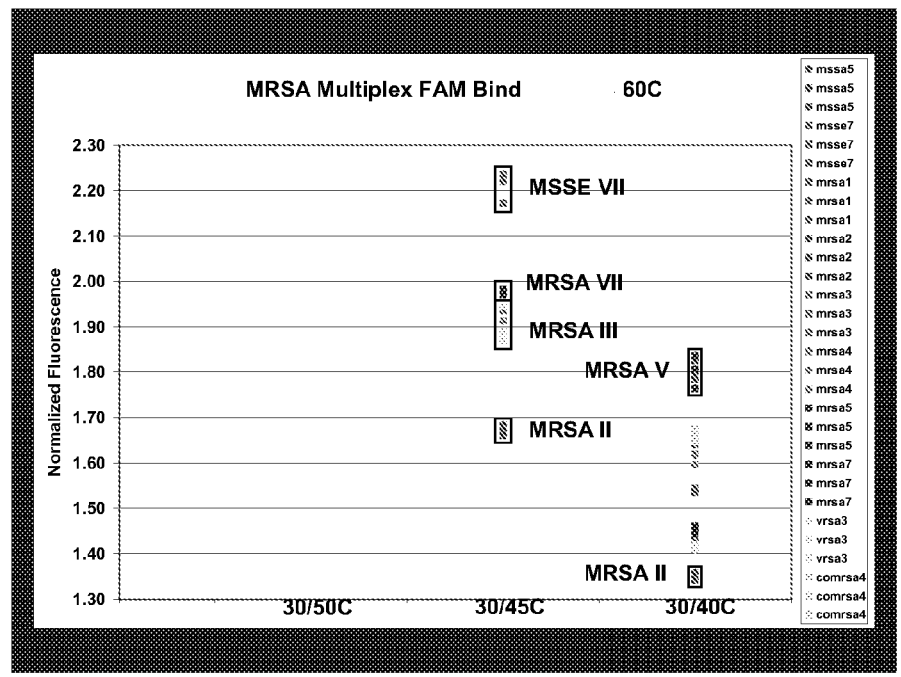
B.
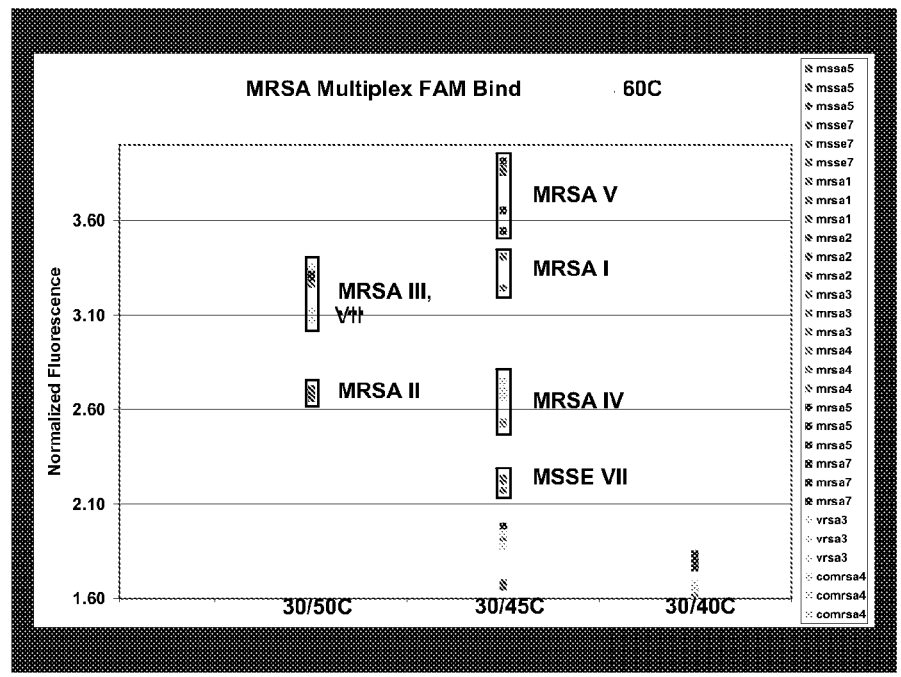

FIGURES 21C-D
C.
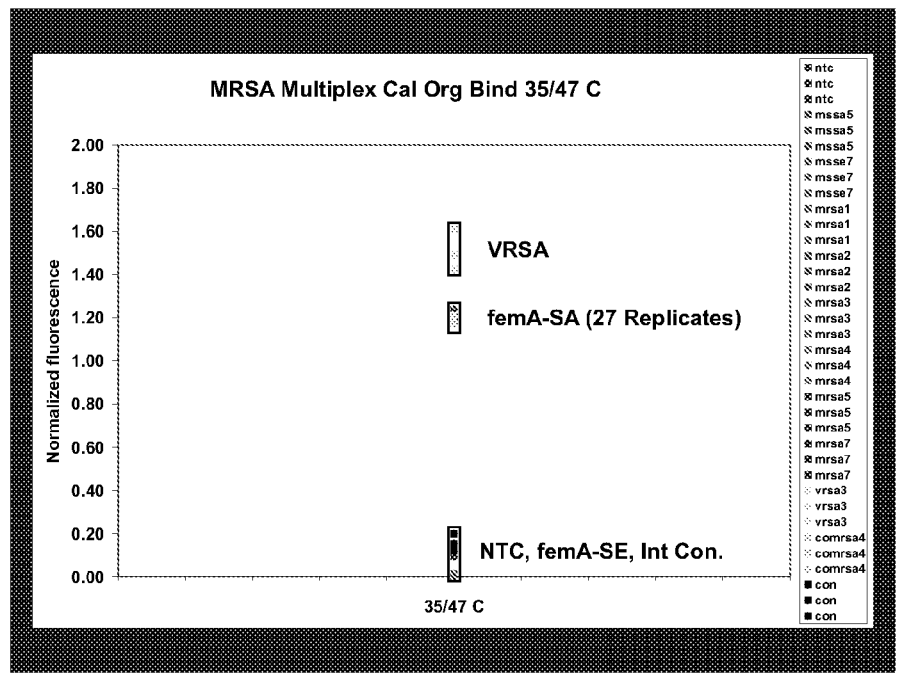
D.
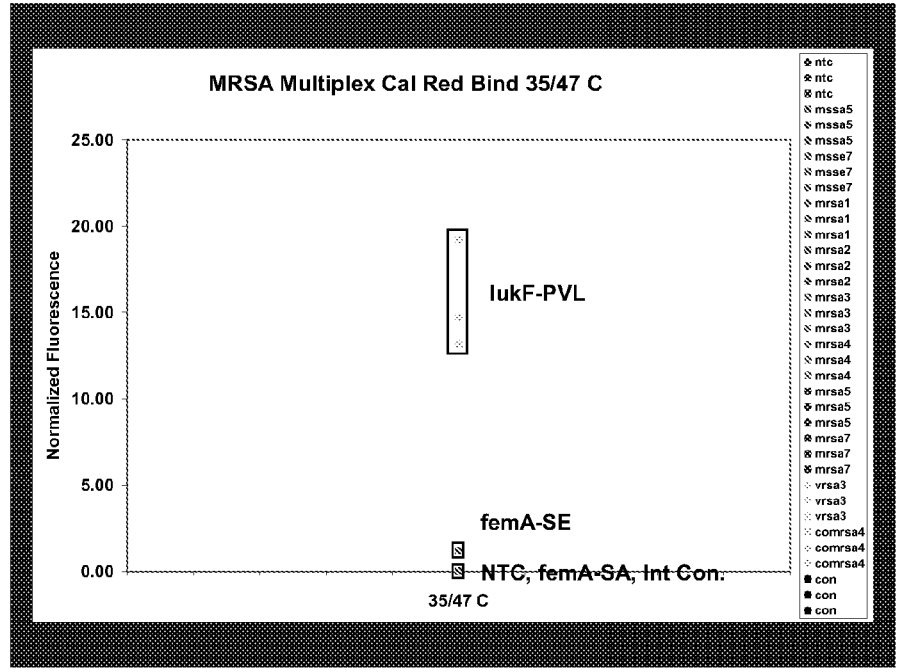

```
                              SEQUENCE LISTING

<160> NUMBER OF SEQ ID NOS: 59

<210> SEQ ID NO 1
<211> LENGTH: 116
<212> TYPE: DNA
<213> ORGANISM: Artificial Sequence
<220> FEATURE:
<223> OTHER INFORMATION: Synthetic

<400> SEQUENCE: 1
ctgattaacc cagtacagat cctttcaatc tatagcgcat tagaaaataa tggcaatatt        60
aacgcacctc acttattaaa agacacttaa ttggcaaatc cggtactgca gaactc          116

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
ctgattaacc cagtacagat cct                                                23

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
gagttctgca gtaccggatt tgcca                                              25

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
aagaggtgcg ttaatattgc tt                                                 22

<210> SEQ ID NO 5
<211> LENGTH: 116
<212> TYPE: DNA
<213> ORGANISM: Artificial Sequence
<220> FEATURE:
```

<223> OTHER INFORMATION: Synthetic

<400> SEQUENCE: 5
cgttgtctat acctacatat cgatccatat ttaccatatc aatacttgaa tcatgatggc    60
gagattacag gtaattgata aaatgagtaa cttaggattt gaacatactg gattcc    116

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
cgttgtctat acctacatat cgatcc    26

<210> SEQ ID NO 7
<211> LENGTH: 35
<212> TYPE: DNA
<213> ORGANISM: Artificial Sequence
<220> FEATURE:
<223> OTHER INFORMATION: Synthetic

<400> SEQUENCE: 7
ggaatccagt atgttcaaat cctaagttac tcatt    35

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
aacctgtaat ctcgccatt    19

<210> SEQ ID NO 9
<211> LENGTH: 120
<212> TYPE: DNA
<213> ORGANISM: Artificial Sequence
<220> FEATURE:
<223> OTHER INFORMATION: Synthetic

<400> SEQUENCE: 9
taagagttga cccatacctt ccatatcaat atttaaatca gggagaaata actggaaatg    60
caggtcatga ttggattttt gatgaattag agagtttagg atataaacac gaaggattcc    120

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
taagagttga cccatacctt cc    22

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11

```
ggaatccttc gtgtttatat cctaaactct ctaattcatc                          40
```

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12

```
attttccagt tatttctccc tat                                            23
```

<210> SEQ ID NO 13
<211> LENGTH: 119
<212> TYPE: DNA
<213> ORGANISM: Artificial Sequence
<220> FEATURE:
<223> OTHER INFORMATION: Synthetic

<400> SEQUENCE: 13

```
ggcagagata gttatcattc aacttatggt aatgaaatgt ttttaggctc aagacaaagc    60
aacttaaatg ctggacaaaa cttcttggaa tatcacaaaa tgccagtgtt atccagagg    119
```

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14

```
ggcagagata gttatcattc aacttat                                        27
```

<210> SEQ ID NO 15
<211> LENGTH: 33
<212> TYPE: DNA
<213> ORGANISM: Artificial Sequence
<220> FEATURE:
<223> OTHER INFORMATION: Synthetic

<400> SEQUENCE: 15

```
cctctggata acactggcat tttgtgatat tcc                                 33
```

<210> SEQ ID NO 16
<211> LENGTH: 15
<212> TYPE: DNA
<213> ORGANISM: Artificial Sequence
<220> FEATURE:
<223> OTHER INFORMATION: Synthetic

<400> SEQUENCE: 16

```
tagttgcttt gtcta                                                     15
```

<210> SEQ ID NO 17
<211> LENGTH: 79
<212> TYPE: DNA
<213> ORGANISM: Artificial Sequence
<220> FEATURE:
<223> OTHER INFORMATION: Synthetic

<400> SEQUENCE: 17

```
gagcaggctg tttcgggctg tgaggtcggt tgtgcggtat tgggaaacag tgccgcgtta    60
gttgttggcg aggtggacc                                                 79
```

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
gagcaggctg tttcgg                                                      16

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggtccacctc gccaacaact aacg                                             24

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
ttaataccgc acaaaa                                                      16

<210> SEQ ID NO 21
<211> LENGTH: 63
<212> TYPE: DNA
<213> ORGANISM: Arabidopsis thaliana

<400> SEQUENCE: 21
gaacattacc tgccatccaa gtgtatcata tcgcaaaacc acaatggtct gttggctcct      60
tgc                                                                    63

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gaacattacc tgccatccaa                                                  20

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
gcaaggagcc aacagaccat tgtg                                             24

<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24
tatttgcgat atgatata                                                18

<210> SEQ ID NO 25
<211> LENGTH: 60
<212> TYPE: DNA
<213> ORGANISM: Arabidopsis thaliana

<400> SEQUENCE: 25
gaacattacc tgccatccaa gttagtggga gcagaccaca atggtctgtt ggctccttgc    60

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gaacattacc tgccatccaa                                              20

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
gcaaggagcc aacagaccat tgtg                                         24

<210> SEQ ID NO 28
<211> LENGTH: 15
<212> TYPE: DNA
<213> ORGANISM: Artificial Sequence
<220> FEATURE:
<223> OTHER INFORMATION: Synthetic

<400> SEQUENCE: 28
aactgctccc acttt                                                   15

<210> SEQ ID NO 29
<211> LENGTH: 95
<212> TYPE: DNA
<213> ORGANISM: Artificial Sequence
<220> FEATURE:
<223> OTHER INFORMATION: Synthetic

<400> SEQUENCE: 29
tcattattcc tcaagaagag atacaatcgg tcacttttaa gaaaggttta cttgcttata    60
aaatggttgt gactactaaa gataacgaag ttcct                              95

<210> SEQ ID NO 30
<211> LENGTH: 29
<212> TYPE: DNA
<213> ORGANISM: Artificial Sequence
<220> FEATURE:
<223> OTHER INFORMATION: Synthetic

<400> SEQUENCE: 30
tcattattcc tcaagaagag atacaatcg                                    29

<210> SEQ ID NO 31

```
<211> LENGTH: 32
<212> TYPE: DNA
<213> ORGANISM: Artificial Sequence
<220> FEATURE:
<223> OTHER INFORMATION: Synthetic

<400> SEQUENCE: 31
aggaacttcg ttatctttag tagtcacaac ca                                     32

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
ataaaccttt cttaaaat                                                     18

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
ttagttttat ttatgatacg cttctcc                                           27

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
accgcatcat ttatgatatg cttctcc                                           27

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
acctcattac ttatgataag cttctcc                                           27

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
tgacattccc acatcaaatg at                                                22

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
```
tttcttaaat gctctataca cttgaa                                              26

<210> SEQ ID NO 38
<211> LENGTH: 98
<212> TYPE: DNA
<213> ORGANISM: Artificial Sequence
<220> FEATURE:
<223> OTHER INFORMATION: Synthetic

<400> SEQUENCE: 38
acctcattac ttatgataag cttctcctcg cataatctta aatgctctgt acacttgttc        60
aattaacaca acccgcatca tttgatgtgg gaatgtca                                98

<210> SEQ ID NO 39
<211> LENGTH: 98
<212> TYPE: DNA
<213> ORGANISM: Artificial Sequence
<220> FEATURE:
<223> OTHER INFORMATION: Synthetic

<400> SEQUENCE: 39
accgcatcat ttatgatatg cttctccacg cataatctta aatgctctat acacttgctc        60
aattaacaca acccgcatca tttgatgtgg gaatgtca                                98

<210> SEQ ID NO 40
<211> LENGTH: 98
<212> TYPE: DNA
<213> ORGANISM: Artificial Sequence
<220> FEATURE:
<223> OTHER INFORMATION: Synthetic

<400> SEQUENCE: 40
ttagttttat ttatgatacg cttctccacg cataatctta aatgctctgt acacttgttc        60
aattaacaca acccgcatca tttgatgtgg gaatgtca                                98

<210> SEQ ID NO 41
<211> LENGTH: 98
<212> TYPE: DNA
<213> ORGANISM: Artificial Sequence
<220> FEATURE:
<223> OTHER INFORMATION: Synthetic

<400> SEQUENCE: 41
accgcatcat ttatgatatg cttctccacg cataatctta aatgctctgt acacttgttc        60
aattaacaca acccgcatca tttgatgtgg gaatgtca                                98

<210> SEQ ID NO 42
<211> LENGTH: 98
<212> TYPE: DNA
<213> ORGANISM: Artificial Sequence
<220> FEATURE:
<223> OTHER INFORMATION: Synthetic

<400> SEQUENCE: 42
accgcatcat ttatgatatg cttctcctcg cataatctta aatgctctgt acacttgttc        60
aattaacaca acccgcatca tttgatgtgg gaatgtca                                98

<210> SEQ ID NO 43
<211> LENGTH: 98
<212> TYPE: DNA
<213> ORGANISM: Artificial Sequence
<220> FEATURE:

<223> OTHER INFORMATION: Synthetic

<400> SEQUENCE: 43
ttagttttat ttatgatacg cttctccacg cataatctta aatgctctat acacttgttc    60
aattaacaca acccgcatca tttgatgtgg gaatgtca    98

<210> SEQ ID NO 44
<211> LENGTH: 98
<212> TYPE: DNA
<213> ORGANISM: Artificial Sequence
<220> FEATURE:
<223> OTHER INFORMATION: Synthetic

<400> SEQUENCE: 44
accgcatcat ttatgatatg cttctcctcg cataatctta aatgctctgt acacttgttc    60
aattaacaca acccgcatca tttgatgtgg gaatgtca    98

<210> SEQ ID NO 45
<211> LENGTH: 98
<212> TYPE: DNA
<213> ORGANISM: Artificial Sequence
<220> FEATURE:
<223> OTHER INFORMATION: Synthetic

<400> SEQUENCE: 45
ttagttttat ttatgatacg cttctcctcg cataatctta aatgctctgt acacttgttc    60
aattaacaca acccgcatca tttgatgtgg gaatgtca    98

<210> SEQ ID NO 46
<211> LENGTH: 98
<212> TYPE: DNA
<213> ORGANISM: Artificial Sequence
<220> FEATURE:
<223> OTHER INFORMATION: Synthetic

<400> SEQUENCE: 46
acctcattac ttatgataag cttctccacg cataatctta aatgctctat acacttgctc    60
aattaacaca acccgcatca tttgatgtgg gaatgtca    98

<210> SEQ ID NO 47
<211> LENGTH: 98
<212> TYPE: DNA
<213> ORGANISM: Artificial Sequence
<220> FEATURE:
<223> OTHER INFORMATION: Synthetic

<400> SEQUENCE: 47
ttagttttat ttatgatacg cttctccacg cataatctta aatgctctat acacttgctc    60
aattaacaca acccgcatca tttgatgtgg gaatgtca    98

<210> SEQ ID NO 48
<211> LENGTH: 98
<212> TYPE: DNA
<213> ORGANISM: Artificial Sequence
<220> FEATURE:
<223> OTHER INFORMATION: Synthetic

<400> SEQUENCE: 48
acctcattac ttatgataag cttctccacg cataatctta aatgctctgt acacttgttc    60
aattaacaca acccgcatca tttgatgtgg gaatgtca    98

```
<210> SEQ ID NO 49
<211> LENGTH: 98
<212> TYPE: DNA
<213> ORGANISM: Artificial Sequence
<220> FEATURE:
<223> OTHER INFORMATION: Synthetic

<400> SEQUENCE: 49
accgcatcat ttatgatatg cttctccacg cataatctta aatgctctgt acacttgttc    60
aattaacaca acccgcatca tttgatgtgg gaatgtca                            98

<210> SEQ ID NO 50
<211> LENGTH: 98
<212> TYPE: DNA
<213> ORGANISM: Artificial Sequence
<220> FEATURE:
<223> OTHER INFORMATION: Synthetic

<400> SEQUENCE: 50
acctcattac ttatgataag cttctccacg cataatctta aatgctctgt acacttgttc    60
aattaacaca acccgcatca tttgatgtgg gaatgtca                            98

<210> SEQ ID NO 51
<211> LENGTH: 98
<212> TYPE: DNA
<213> ORGANISM: Artificial Sequence
<220> FEATURE:
<223> OTHER INFORMATION: Synthetic

<400> SEQUENCE: 51
ttagttttat ttatgatacg cttctccacg cataatctta aatgctctgt acacttgttc    60
aattaacaca acccgcatca tttgatgtgg gaatgtca                            98

<210> SEQ ID NO 52
<211> LENGTH: 98
<212> TYPE: DNA
<213> ORGANISM: Artificial Sequence
<220> FEATURE:
<223> OTHER INFORMATION: Synthetic

<400> SEQUENCE: 52
acctcattac ttatgataag cttctcctcg cataatctta aatgctctgt acacttgttc    60
aattaacaca acccgcatca tttgatgtgg gaatgtca                            98

<210> SEQ ID NO 53
<211> LENGTH: 98
<212> TYPE: DNA
<213> ORGANISM: Artificial Sequence
<220> FEATURE:
<223> OTHER INFORMATION: Synthetic

<400> SEQUENCE: 53
ttagttttat ttatgatacg cttctcctcg cataatctta aatgctctgt acacttgttc    60
aattaacaca acccgcatca tttgatgtgg gaatgtca                            98

<210> SEQ ID NO 54
<211> LENGTH: 98
<212> TYPE: DNA
<213> ORGANISM: Artificial Sequence
<220> FEATURE:
<223> OTHER INFORMATION: Synthetic

<400> SEQUENCE: 54
```

```
acctcattac ttatgataag cttctccacg cataatctta aatgctctat acacttgttc    60
aattaacaca acccgcatca tttgatgtgg gaatgtca                            98
```

<210> SEQ ID NO 55
<211> LENGTH: 98
<212> TYPE: DNA
<213> ORGANISM: Artificial Sequence
<220> FEATURE:
<223> OTHER INFORMATION: Synthetic

<400> SEQUENCE: 55

```
accgcatcat ttatgatatg cttctccacg cataatctta aatgctctat acacttgttc    60
aattaacaca acccgcatca tttgatgtgg gaatgtca                            98
```

<210> SEQ ID NO 56
<211> LENGTH: 168
<212> TYPE: DNA
<213> ORGANISM: Artificial Sequence
<220> FEATURE:
<223> OTHER INFORMATION: Synthetic

<400> SEQUENCE: 56

```
gaggtggcct ttccaataca atattggtct caaaacaaat gaccccaatg tagatttaat    60
aaattatcta cctaaaaata aaatagattc agtaaatgtt agtcaaacat taggttataa   120
cataggtggt aattttaata gtggtccatc aacaggaggt aatggttc                168
```

<210> SEQ ID NO 57
<211> LENGTH: 19
<212> TYPE: DNA
<213> ORGANISM: Artificial Sequence
<220> FEATURE:
<223> OTHER INFORMATION: Synthetic

<400> SEQUENCE: 57

```
gaggtggcct ttccaatac                                                 19
```

<210> SEQ ID NO 58
<211> LENGTH: 28
<212> TYPE: DNA
<213> ORGANISM: Artificial Sequence
<220> FEATURE:
<223> OTHER INFORMATION: Synthetic

<400> SEQUENCE: 58

```
gaaccattac ctcctgttga tggaccac                                       28
```

<210> SEQ ID NO 59
<211> LENGTH: 28
<212> TYPE: DNA
<213> ORGANISM: Artificial Sequence
<220> FEATURE:
<223> OTHER INFORMATION: Synthetic

<400> SEQUENCE: 59

```
tgtaccacct atgttataac ctaatgca                                       28
```

SINGLE PROBE, MULTIPLE TEMPERATURE, NUCLEIC ACID DETECTION METHODS, KITS, AND COMPOSITIONS

This application is a 371 US National Entry of International Patent Application Ser. No. PCT/US2010/045199 filed Aug. 11, 2010, which claims benefit to U.S. provisional patent application No. 61/232,999 filed Aug. 11, 2009, each of which is hereby incorporated by reference in its entirety.

The present application claims priority to U.S. Provisional Patent Application Ser. No. 61/232,999, filed Aug. 11, 2009, the entire disclosure of which is herein incorporated by reference in its entirety.

FIELD

Provided herein are methods, kits, and compositions related to nucleic acid detection assays that allow discrimination of multiple target sequences with a single probe. In particular, provided herein are methods kits, and compositions that include single-probe target sequence discrimination where different target amplicons may have identical probe hybridization sequences by employing multiple temperature end-point signal probe detection. Also provided herein are methods, kits, and compositions for distinguishing between two or more target amplicons using multiple-temperature end-point probe detection. In certain embodiments, asymmetric PCR amplification methods are employed (e.g., LATE-PCR amplification).

BACKGROUND

*Staphylococcus aureus* (*S. aureus*) can be a virulent pathogen of animals and humans. It can also cause severe food poisoning by the production of a toxin. Diseases caused by *S. aureus* cover a very wide clinical spectrum, from simple skin infections to life threatening infections of the bones, heart, and organs. Of particular concern is the recognition that *S. aureus* infection is common after surgery. It is also associated with intravenous tubing and other implants.

The bacterium *S. aureus* may be transmitted between healthy individuals by skin to skin contact, or from a commonly shared item or a surface (e.g., tanning beds, gym equipment, food handling equipment, etc.) where the transfer may be made to a subsequent person who uses the shared item or touches the surface. Of great medical concern is the recognition that healthy people entering hospitals may "carry" *S. aureus* (e.g., on their skin, in their noses, etc.) without any signs or symptoms. In the presence of favorable conditions (often found in, but not limited to hospitals), the *S. aureus* can activate and cause serious infection. In addition, *S. aureus* can also be a source of food poisoning, often caused by a food handler contaminating the food product.

There are two broad categories of *S. aureus* based on an individual clone's susceptibility to a class of *B. lactam* antibiotics that includes methicillin. These are methicillin susceptible *S. aureus* (MSSA), and methicillin resistant *S. aureus* (MRSA). Until only a few years ago, various strains of MRSA were almost exclusively found in hospitals. Now, many are also present in the noses, skin, etc. of people in the non-hospital community. Moreover, these MRSA strains are increasingly causing serious infections in the community. MRSA is particularly serious because very few antibiotics (e.g., vancomycin) have been shown to be uniformly effective against MRSA.

The Center for Disease Control and Prevention actively surveys for the development of methicillin resistant *S. aureus*. In 2000, the Society for Healthcare Epidemiology of America guidelines recommended contact isolation for patients with MRSA. In addition to the morbidity and mortality caused by MRSA, it has been estimated that each case of infection costs at least $23,000. Methicillin-susceptible *Staphylococcus aureus* (MSSA) and Methicillin-resistant *Staphylococcus aureus* (MRSA) are increasingly infecting people worldwide in both hospitals and within the community. The rate of infections in ICUs is especially troubling, rising from 2% in 1974 to 64% in 2004. One in three people carry MSSA while one in 100 people carry MRSA.

SUMMARY

Provided herein are methods, kits, and compositions related to nucleic acid detection assays that allow discrimination of multiple target sequences with a single probe. In particular, provided herein are methods kits, and compositions that include single-probe target sequence discrimination where different target amplicons may have identical probe hybridization sequences by employing multiple temperature end-point signal probe detection. Also provided herein are methods, kits, and compositions for distinguishing between two or more target amplicons using multiple-temperature end-point probe detection. In certain embodiments, asymmetric PCR amplification methods are employed (e.g., LATE-PCR amplification).

In some embodiments, methods are provided for identifying the presence of polymorphic target sequence variants (e.g., SCCmec variants) in a sample, comprising: a) providing: i) a sample suspected of containing: a first or second variant of a polymorphic target sequence, ii) a labeled probe, iii) a first variant temperature/temperature signal ratio, iv) a second variant temperature/temperature signal ratio, v) at least one forward primer, and vi) at least one reverse primer; b) combining the sample, the labeled probe, the forward primer, and the reverse primer to generate a combined sample and treating the combined sample under amplification conditions such that: a first single-stranded amplicon is generated if the first variant is present, and a second single-stranded amplicon is generated if the second variant is present, wherein the first and second single-stranded amplicons each comprise the following identical sequences: i) a probe hybridization sequence, ii) a 5' end corresponding to the sequence of the reverse primer, and iii) a 3' end complementary to the forward primer; and wherein the first and second single-stranded amplicons do not have complete sequence identity; c) exposing the combined sample to multiple temperatures that allow the labeled probe to hybridize to the probe hybridization sequence and produce temperature-dependent signals; d) detecting the temperature-dependent signals at least two temperatures; e) generating an experimental temperature/temperature signal ratio; and f) comparing the experimental temperature/temperature signal ratio with the first and second variant temperature/temperature signal ratios, wherein a match between the experimental temperature/temperature signal ratio and the first or second variant temperature/temperature signal ratio identifies the presence of the first or second variant in the sample.

In certain embodiments, the forward primer comprises a limiting primer and the reverse primer comprises an excess primer, wherein the excess primer is added to the combined sample at a concentration at least two-times (e.g., two-times . . . five-times . . . 50-times . . . 100-times . . .

1000-times . . . ) that of the limiting primer, and wherein the amplification conditions comprise asymmetric PCR conditions. In some embodiments, the forward primer comprises an excess primer and the reverse primer comprises a limiting primer, wherein the excess primer is added to the combined sample at a concentration at least two-times (e.g., two-time . . . five-times . . . 50-times . . . 100-times . . . 1000-times . . . ) that of the limiting primer, and wherein the amplification conditions comprise asymmetric PCR conditions. In other embodiments, the asymmetric PCR conditions are LATE-PCR conditions, and wherein the initial melting temperature of the limiting primer is equal to or higher than the initial melting temperature of the excess primer. In further embodiments, each of the single-stranded amplicons comprise at least one amplicon spacer region selected from: A) a 5' spacer region that is adjacent to the 5' end and the probe hybridization site, and B) a 3' spacer regions adjacent to the 3' end and the probe hybridization site; and wherein at least one of the 5' and 3' spacer regions differ in sequence between the first and second single-stranded amplicons. In particular embodiments, the 5' and/or 3' spacer regions have secondary structure within a temperature range 25-85° C.

In some embodiments, the presence of the first or second variant is identified in the sample by finding a match between the experimental temperature/temperature signal ratio and the first or second variant temperature/temperature signal ratio. In other embodiments, the methods further comprise: providing a combined-variant temperature/temperature signal ratio, and comparing the experimental temperature/temperature signal ratio to the combined-variant temperature/temperature signal ratio, wherein a match between the experimental temperature/temperature signal ratio and the combined-variant temperature/temperature signal ratio identifies the presence of both the first and second variants in the sample. In particular embodiments, the presence of the first and second variants is identified in the sample by finding a match between the experimental temperature/temperature signal ratio and the combined-variant temperature/temperature signal ratio. In other embodiments, a match is found when the experimental temperature/temperature signal ratio is within 0.4 (e.g., 0.4, 0.3, 0.2, 0.1, or 0.0) of the first or second variant temperature/temperature signal ratios.

In further embodiments, the exposing the combined sample to multiple temperatures comprises gradually cooling the combined sample such that the temperature-dependent signals are binding signals. In additional embodiments, the exposing the combined sample to multiple temperatures comprises gradually heating the combined sample such that the temperature-dependent signals are melting signals. In certain embodiments, the gradual cooling or the gradual heating is carried out more than once and the values of these repeats are averaged.

In further embodiments, the generating an experimental temperature/temperature signal ratio includes normalizing the temperature-dependent signals with a reference temperature, and wherein the first and second variant temperature/temperature signal ratios are normalized with the reference temperature.

In particular embodiments, the labeled probe comprises a molecular beacon probe. In certain embodiments, the molecular beacon probe comprises a stem that is precisely two base-pairs in length.

In some embodiments, the polymorphic target sequences comprises a SCCmec region from MRSA spanning the mecA-orfX boundary, and wherein the first and second single-stranded amplicons each comprise a portion of the mecA gene and a portion of the orfX region. In other embodiments, the first or second variants are selected from: SCCmec type I, SCCmec type II, SCCmec type III, SCCmec type IV, SCCmec type V, and SCCmec type VII.

In some embodiments, compositions are provided comprising: a) a labeled probe; b) a forward primer; c) a reverse primer; d) first and second single-stranded amplicons that each comprise the following identical sequences: i) a probe hybridization sequence, ii) a 5' end corresponding to the sequence of the reverse primer, and iii) a 3' end complementary to the forward primer; and wherein the first and second single-stranded amplicons do not have complete sequence identity (e.g., they differ by 1 base, or 2 bases . . . 5 bases . . . or more).

In certain embodiments, systems are provided comprising: a) a labeled probe; b) a first variant temperature/temperature signal ratio; c) a second variant temperature/temperature signal ratio; d) a forward primer; e) a reverse primer; f) first and second single-stranded amplicons that each comprise the following identical sequences: i) a probe hybridization sequence, ii) a 5' end corresponding to the sequence of the reverse primer, and iii) a 3' end complementary to the forward primer; and wherein the first and second single-stranded amplicons do not have complete sequence identity.

In some embodiments, methods are provided for identifying the presence of polymorphic target sequence variants (e.g., SCCmec variants) in a sample comprising: a) providing: i) a sample suspected of containing: a first or second variant of a polymorphic target sequence, ii) a labeled probe, iii) a first variant temperature/temperature signal ratio, iv) a second variant temperature/temperature signal ratio, v) first and second forward primers that differ in sequence, and vi) a reverse primer; b) combining the sample, the labeled probe, the first and second forward primers, and the reverse primer to generate a combined sample and treating the combined sample under amplification conditions such that: a first single-stranded amplicon is generated comprising a first 3' end complementary to the first forward primer, and a second single-stranded amplicon is generated comprising a second 3' end complementary to the second forward primer, and wherein the first and second single-stranded amplicons each further comprise the following identical sequences: i) a probe hybridization sequence, and ii) a 5' end corresponding to the sequence of the reverse primer; c) exposing the combined sample to multiple temperatures that allow the labeled probe to hybridize to the probe hybridization sequence and produce temperature-dependent signals; d) detecting the temperature-dependent signals at least two temperatures; e) generating an experimental temperature/temperature signal ratio; and f) comparing the experimental temperature/temperature signal ratio with the first and second variant temperature/temperature signal ratios, wherein a match between the experimental temperature/temperature signal ratio and the first or second variant temperature/temperature signal ratios identifies the presence of the first or second variant in the sample.

In other embodiments, the first and second forward primers comprise corresponding first and second limiting primers, and the reverse primer comprises an excess primer, wherein the excess primer is added to the combined sample at a concentration at least five-times that of the first and second limiting primers, and wherein the amplification conditions comprise asymmetric PCR conditions. In further embodiments, the first single-stranded amplicon is generated in an amount that is at least 2-fold greater (e.g., 2- fold . . . 10-fold . . . 25-fold . . . 100-fold . . . 1000-fold . . . ) than the second single-stranded amplicon, and wherein there is a match between the experimental temperature/temperature signal ratio and the first variant temperature/temperature signal ratio, thereby identifying the presence of the first variant. In other embodiments, the second single-stranded amplicon is generated in an amount that is at least 2-fold greater (e.g., 2-fold . . . 10-fold . . . 25-fold . . . 100-fold . . . 1000-fold . . . ) than the first single-stranded amplicon, and wherein there is a match between the experimental temperature/temperature signal ratio and the second variant temperature/temperature signal ratio, thereby identifying the presence of the second variant.

In some embodiments, methods are provided for identifying the presence of polymorphic target sequence variants (e.g., SCCmec variants) in a sample comprising: a) providing: i) a sample suspected of containing: a first, second, or third variant of a polymorphic target sequence, ii) a labeled probe, iii) a first variant temperature/temperature signal ratio, iv) a second variant temperature/temperature signal ratio, v) a third variant temperature/temperature signal ratio, vi) a forward primer, and vii) a reverse primer; b) combining the sample, the labeled probe, the forward primer, and the reverse primer to generate a combined sample and treating the combined sample under amplification conditions such that: a first single-stranded amplicon is generated if the first variant is present, a second single-stranded amplicon is generated if the second variant is present, and a third-single stranded amplicon is generated if the third variant is present, wherein the first, second, and third single-stranded amplicons each comprise the following identical sequences: i) a 5' end corresponding to the sequence of the reverse primer, and ii) a 3' end complementary to the forward primer; and wherein the first, second, and third single-stranded amplicons comprise identical or different probe hybridization sequences, and do not have complete sequence identity to each other; c) exposing the combined sample to multiple temperatures that allow the labeled probe to hybridize to the probe hybridization sequences and produce temperature-dependent signals; d) detecting the temperature-dependent signals at least two temperatures; e) generating an experimental temperature/temperature signal ratio; and f) comparing the experimental temperature/temperature signal ratio with the first, second, and third variant temperature/temperature signal ratios, wherein a match between the experimental temperature/temperature signal ratio and the first, second, or third variant temperature/temperature signal ratio identifies the presence of the first, second, or third variant in the sample.

In certain embodiments, the at least two of the first, second, and third single-stranded amplicons comprise identical probe hybridization sequences. In other embodiments, all three of the first, second, and third single-stranded amplicons comprise identical probe hybridization sequences.

In other embodiments, methods are provided for identifying the presence of polymorphic target sequence variants (e.g., SCCmec variants) in a sample comprising: a) providing: i) a sample suspected of containing: a first, second, or third variant of a polymorphic target sequence, ii) a labeled probe, iii) a first variant temperature/temperature signal ratio, iv) a second variant temperature/temperature signal ratio, v) a third variant temperature/temperature signal ratio, vi) first and second forward primers that differ in sequence, and vii) a reverse primer; b) combining the sample, the labeled probe, the first and second forward primers, and the reverse primer to generate a combined sample and treating the combined sample under amplification conditions such that: a first single-stranded amplicon is generated comprising a first 3' end complementary to the first forward primer, a second single-stranded amplicon is generated comprising a second 3' end complementary to the second forward primer, and a third single-stranded amplicon is generated comprising a third 3' end that is complementary to either the first forward primer or the second forward primer, and wherein the first, second, and third single-stranded amplicons each further comprise: i) identical 5' ends corresponding to the sequence of the reverse primer, and ii) identical or different probe hybridization sequences; c) exposing the combined sample to multiple temperatures that allow the labeled probe to hybridize to the probe hybridization sequences and produce temperature-dependent signals; d) detecting the temperature-dependent signals at least two temperatures; e) generating an experimental temperature/temperature signal ratio; and f) comparing the experimental temperature/temperature signal ratio with the first, second, and third variant temperature/temperature signal ratios, wherein a match between the experimental temperature/temperature signal ratio and the first, second, or third variant temperature/temperature signal ratios identifies the presence of the first, second, or third variant in the sample.

In some embodiments, methods are provided for identifying the SCCmec type present in a sample comprising: a) providing: i) a sample suspected of containing a SCCmec containing *Staphylococcus*, including but not limited to type I, type II, type III, type IV, type V, or type VII SCCmec, ii) a labeled probe, iii) temperature/temperature signal ratio (e.g., in a database) for at least one type from the list: type I, type II, type III, type IV, type V, and type VII, iv) first, second, and third forward primers that differ in sequence, and v) a reverse primer; b) combining the sample, the labeled probe, the first, second, and third forward primers, and the reverse primer to generate a combined sample and treating the combined sample under amplification conditions such that: type I, II, III, IV, V, and VII single-stranded amplicons are generated if the corresponding SSCmec types are present in the sample, wherein: the type I single-stranded amplicon comprises a first 3' end complementary to the first forward primer, the type II, IV, and V single-stranded amplicons each comprise identical second 3' ends complementary to the second forward primer, the type III and VII single-stranded amplicons each comprise identical third 3' ends complementary to the third forward primer, wherein the type I, II, III, IV, V, and VII single-stranded amplicons each further comprise: i) identical 5' ends corresponding to the sequence of the reverse primer, and ii) identical or different probe hybridization sequences; and wherein the type I, II, III, IV, V, and VII single-stranded amplicons do not have complete sequence identity; c) exposing the combined sample to multiple temperatures that allow the labeled probe to hybridize to the probe hybridization sequences and produce temperature-dependent signals; d) detecting the temperature-dependent signals at least two temperatures; e) generating an experimental temperature/temperature signal ratio; and f) comparing the experimental temperature/temperature signal ratio with the type I, II, III, IV, V, and VII temperature/temperature signal ratios, wherein a match between the experimental temperature/temperature signal ratio and the type I, II, III, IV, V, or VII temperature/temperature signal ratios identifies the presence of the type I, II, III, IV, V, or VII SCCmec containing *Staphylococcus* in the sample.

In particular embodiments, the type I, III, IV, and V single-stranded amplicons comprise identical probe hybridization sequences with respect to the labeled probe. In other embodiments, the type II and VII single-stranded amplicons comprise identical probe hybridization sequences with respect to the labeled probe. In other embodiments, the forward primers comprises limiting primers and the reverse primer comprises an excess primer, wherein the excess primer is added to the combined sample at a concentration at least five-times (e.g., 5-times . . . 100-times . . . 1000-times . . . ) that of any of the limiting primers, and wherein the amplification conditions comprise asymmetric PCR conditions. In particular embodiments, the asymmetric PCR conditions are LATE-PCR conditions, and wherein the initial melting temperature of the limiting primers are equal to or higher than the initial melting temperature of the excess primer.

In certain embodiments, each of the single-stranded amplicons comprise at least one amplicon spacer region selected from: A) a 5' spacer region that is adjacent to the 5' end and the probe hybridization site, and B) a 3' spacer regions adjacent to the 3' end and the probe hybridization site; and wherein at least one of the 5' and 3' spacer regions differ in sequence between the type IV and type V single-stranded amplicons.

In other embodiments, the presence of the type I, II, III, IV, V, or VII SCCmec containing *Staphylococcus* is identified in the sample by finding a match between the experimental temperature/temperature signal ratio and the type I, type II, type III, type IV, type V, and type VII temperature/temperature signal ratios. In further embodiments, a match is found when the experimental temperature/temperature signal ratio is within 0.4 (e.g., 0.4, 0.3, 0.2, 0.1, and 0.0) of the type I, type II, type III, type IV, type V, and type VII temperature/temperature signal ratios.

In some embodiments, the exposing the combined sample to multiple temperatures comprises gradually cooling the combined sample such that the temperature-dependent signals are binding signals. In further embodiments, the exposing the combined sample to multiple temperatures comprises gradually heating the combined sample such that the temperature-dependent signals are melting signals.

In particular embodiments, the generating an experimental temperature/temperature signal ratio includes normalizing the temperature-dependent signals with a reference temperature, and wherein the type I, type II, type III, type IV, type V, and type VII temperature/temperature signal ratios are normalized with the reference temperature.

In additional embodiments, the labeled probe comprises a molecular beacon probe. In further embodiments, the molecular beacon probe comprises a stem that is precisely two base-pairs in length. In some embodiments, the third forward primer comprises or consists of the sequence shown in SEQ ID NO:33. In other embodiments, the second forward primer comprises or consists of the sequence shown in SEQ ID NO:34. In additional embodiments, the first forward primer comprises or consists of the sequence shown in SEQ ID NO:35. In further embodiments, the reverse primer comprises or consists of the sequence shown in SEQ ID NO:36. In additional embodiments, the labeled probe comprises or consists of the sequence shown in SEQ ID NO:37. In particular embodiments, the type I single-stranded amplicon comprises or consists of the complement of the sequence shown in SEQ ID NO:38. In other embodiments, the type II single-stranded amplicon comprises or consists of the complement of the sequence shown in SEQ ID NO:39. In particular embodiments, the type III single-stranded amplicon comprises or consists of the complement of the sequence shown in SEQ ID NO:40. In further embodiments, the type IV single-stranded amplicon comprises or consists of the complement of the sequence shown in SEQ ID NO:41. In additional embodiments, the type V single-stranded amplicon comprises or consists of the complement of the sequence shown in SEQ ID NO:42. In other embodiments, the type VII single-stranded amplicon comprises or consists of the complement of the sequence shown in SEQ ID NO:43.

In particular embodiments, compositions are provided comprising at least one purified nucleic acid sequence, wherein the at least one purified nucleic acid sequence comprises or consists of a sequence selected from the group consisting of: SEQ ID NO:33, SEQ ID NO:34, SEQ ID NO:35, SEQ ID NO:36, and SEQ ID NO:37, or the complement of any one of these sequences; as well as the complement of any one of these sequences. In certain embodiments, the compositions further comprise at least two purified nucleic acid sequences selected from the recited group. In further embodiments, the compositions further comprise at least three purified nucleic acid sequences selected from the recited group.

In some embodiments, compositions are provided comprising at least one purified nucleic acid sequence, wherein the at least one purified nucleic acid sequence comprises or consists of a sequence selected from the group consisting of: SEQ ID NO:33, SEQ ID NO:34, SEQ ID NO:35, SEQ ID NO:36, SEQ ID NO:37, the complement of SEQ ID NO:38, the complement of SEQ ID NO:39, the complement of SEQ ID NO:40, the complement of SEQ ID NO:41, the complement of SEQ ID NO:42, and the complement of SEQ ID NO:43; as well as the complement of any one of these sequences. In further embodiments, wherein the composition further comprises at least two or at least three, or at least four, or at least five purified nucleic acid sequences selected from the recited group.

In some embodiments, methods are provided of detecting a target sequence comprising: a) providing: i) a forward primer, ii) a reverse primer, iii) a labeled probe, wherein the labeled probe is a molecular beacon with a stem that is precisely two or three base-pairs in length, iv) a sample suspected of containing the target sequence, and v) a target sequence temperature/temperature signal ratio; b) combining the sample, the labeled probe, the forward primer, and the reverse primer to generate a combined sample and treating the combined sample under amplification conditions such that a target amplicon is generated if the target sequence is present in the sample; c) exposing the combined sample to multiple temperatures that allow the labeled probe to hybridize to the target amplicon and produce temperature-dependent signals; d) detecting the temperature-dependent signals at least two temperatures; e) generating an experimental temperature/temperature signal ratio; and f) comparing the experimental temperature/temperature signal ratio with the target sequence temperature/temperature signal ratio, wherein a match between the experimental temperature/temperature signal ratio and the target sequence temperature/temperature signal ratio identifies the presence of the target sequence in the sample.

In particular embodiments, the target sequence is selected from the group consisting of: mecA, femA-SA, femA-SE, lukF-PV, lukS-PV, VanA, and SCCmec. In other embodiments, the labeled probe consists of a sequence selected from the group consisting of: SEQ ID NO:4, SEQ ID NO:8, SEQ ID NO:12, SEQ ID NO:16, SEQ ID NO:20, SEQ ID NO:37, and SEQ ID NO:59, or complement of any of these sequences. In further embodiments, the forward primer consists of a sequence selected from the group consisting of:

SEQ ID NO:3, SEQ ID NO:7, SEQ ID NO:11, SEQ ID NO:15, SEQ ID NO:19, SEQ ID NO:33, SEQ ID NO:34, SEQ ID NO:35, and SEQ ID NO:58, or the complement of any of these sequences. In further embodiments, the reverse primer consists of a sequence selected from the group consisting of: SEQ ID NO:2, SEQ ID NO:6, SEQ ID NO:10, SEQ ID NO:14, SEQ ID NO:18, SEQ ID NO:36, and SEQ ID NO:57, or the complement of any of these sequences. In other embodiments, the target amplicon consists of a sequence selected from the group consisting of: SEQ ID NO:1, SEQ ID NO:5, SEQ ID NO:9, SEQ ID NO:13, SEQ ID NO:17, the complement of SEQ ID NO:38, the complement of SEQ ID NO:39, the complement of SEQ ID NO:40, the complement of SEQ ID NO:41, the complement of SEQ ID NO:42, the complement of SEQ ID NO:43, and the complement of SEQ ID NO:56; or the complement of any of these sequences.

In some embodiments, methods are provided of detecting SCCmec containing *Staphylococcus* comprising: a) providing: i) a forward primer comprising or consisting of a sequence selected from the group consisting of: SEQ ID NO:33, SEQ ID NO:34, and SEQ ID NO:35, ii) a reverse primer comprising or consisting of SEQ ID NO:36, iii) a labeled probe, iv) a sample suspected of containing SCCmec containing *Staphylococcus*; b) combining the sample, the labeled probe, the forward primer, and the reverse primer to generate a combined sample and treating the combined sample under amplification conditions such that a target amplicon is generated if the SCCmec containing *Staphylococcus* is present in the sample; and c) detecting any signal from the labeled probe thereby detecting the presence or absence of the target amplicon in the combined sample.

In certain embodiments, the labeled probe comprises or consists of SEQ ID NO:37. In other embodiments, the labeled probe is a molecular beacon probe, and wherein the molecular beacon probe comprises a stem that is precisely two base-pairs in length. In further embodiments, the target amplicon comprises or consists of the complement of SEQ ID NOs 38-43.

In other embodiments, the forward primer comprises a limiting primer and the reverse primer comprises an excess primer, wherein the excess primer is added to the combined sample at a concentration at least five-times that of the limiting primer, and wherein the amplification conditions comprise asymmetric PCR conditions. In particular embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a SCCmec temperature/temperature signal ratio, wherein a match between the experimental temperature/temperature signal ratio and the SCCmec temperature/temperature signal ratio identifies the presence of SCCmec containing *Staphylococcus* in the sample.

In further embodiments, compositions are provided comprising at least one (e.g., at least one, at least two, at least three, at least four, at least five, at least six, at least seven, or at least eight) purified nucleic acid sequence, wherein the at least one purified nucleic acid sequence comprises or consists of a sequence selected from the group consisting of: any of SEQ ID NOs:33-37, or the complement of any of SEQ ID NOs:38-55.

In additional embodiments, kits are provided comprising at least two purified nucleic acid sequences, wherein the at least two (e.g., at least two, at least three, at least four, at least five, at least six, at least seven, or at least eight) purified nucleic acid sequences each comprises or consist of a sequence selected from the group consisting of: any of SEQ ID NOs:33-37, or the complement of any of SEQ ID NOs:38-55.

In some embodiments, methods are provided of detecting mecA containing *Staphylococcus* comprising: a) providing: i) a forward primer comprising or consisting of SEQ ID NO:3, ii) a reverse primer comprising or consisting of SEQ ID NO:2, iii) a labeled probe, iv) a sample suspected of containing mecA containing *Staphylococcus*; b) combining the sample, the labeled probe, the forward primer, and the reverse primer to generate a combined sample and treating the combined sample under amplification conditions such that a target amplicon is generated if the mecA containing *Staphylococcus* is present in the sample; and c) detecting any signal from the labeled probe thereby detecting the presence or absence of the target amplicon in the combined sample.

In certain embodiments, the labeled probe comprises or consists of SEQ ID NO:4. In other embodiments, the labeled probe is a molecular beacon probe, and wherein the molecular beacon probe comprises a stem that is precisely three base-pairs in length. In further embodiments, the target amplicon comprises or consists of SEQ ID NO:1 or complement thereof.

In other embodiments, the forward primer comprises a limiting primer and the reverse primer comprises an excess primer, wherein the excess primer is added to the combined sample at a concentration at least five-times (e.g., at least 5× . . . 100× . . . 1000× . . . ) that of the limiting primer, and wherein the amplification conditions comprise asymmetric PCR conditions.

In some embodiments, the detecting step comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a mecA temperature/temperature signal ratio, wherein a match between the experimental temperature/temperature signal ratio and the mecA temperature/temperature signal ratio identifies the presence of mecA containing *Staphylococcus* in the sample.

In particular embodiments, compositions are provided comprising at least one (e.g., at least one, at least two, at least three, at least four, at least four, etc) purified nucleic acid sequence, wherein the at least one purified nucleic acid sequence comprises or consists of a sequence selected from the group consisting of: any of SEQ ID NOs:1-4 or complements thereof.

In other embodiments, kits are provided comprising at least two (e.g., at least two, at least three, at least four, etc.) purified nucleic acid sequences, wherein the at least two purified nucleic acid sequences each comprises or consist of a sequence selected from the group consisting of: any of SEQ ID NOs:1-4 or complements thereof.

In further embodiments, methods are provided of detecting femA-SA containing *S. aureus* comprising: a) providing: i) a forward primer comprising or consisting of SEQ ID NO:7, ii) a reverse primer comprising or consisting of SEQ ID NO:6, iii) a labeled probe, iv) a sample suspected of containing femA-SA containing *S. aureus*; b) combining the sample, the labeled probe, the forward primer, and the reverse primer to generate a combined sample and treating the combined sample under amplification conditions such that a target amplicon is generated if the femA-SA containing S. aureus is present in the sample; and c) detecting any signal from the labeled probe thereby detecting the presence or absence of the target amplicon in the combined sample.

In certain embodiments, the labeled probe comprises or consists of SEQ ID NO:8. In other embodiments, the labeled probe is a molecular beacon probe, and wherein the molecular beacon probe comprises a stem that is precisely two base-pairs in length. In further embodiments, the target amplicon comprises or consists of SEQ ID NO:5 or complement thereof.

In additional embodiments, the forward primer comprises a limiting primer and the reverse primer comprises an excess primer, wherein the excess primer is added to the combined sample at a concentration at least five-times (e.g., 5× . . . 100× . . . 1000× . . . ) that of the limiting primer, and wherein the amplification conditions comprise asymmetric PCR conditions.

In further embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a femA-SA temperature/temperature signal ratio, wherein a match between the experimental temperature/temperature signal ratio and the femA-SA temperature/temperature signal ratio identifies the presence of femA-SA containing Staphylococcus in the sample.

In some embodiments, compositions are provided comprising at least one (e.g., at least one, at least two, at least three, or at least four) purified nucleic acid sequence, wherein the at least one purified nucleic acid sequence comprises or consists of a sequence selected from the group consisting of: any of SEQ ID NOs:5-8 or complements thereof.

In other embodiments, kits are provided comprising at least two (e.g., at least two, at least three, or at least four) purified nucleic acid sequences, wherein the at least two purified nucleic acid sequences each comprises or consist of a sequence selected from the group consisting of: any of SEQ ID NOs:1-4 or complements thereof.

In some embodiments, methods are provided of detecting femA-SE containing Staphylococcus comprising: a) providing: i) a forward primer comprising or consisting of SEQ ID NO:11, ii) a reverse primer comprising or consisting of SEQ ID NO:10, iii) a labeled probe, iv) a sample suspected of containing femA-SE containing Staphylococcus; b) combining the sample, the labeled probe, the forward primer, and the reverse primer to generate a combined sample and treating the combined sample under amplification conditions such that a target amplicon is generated if the femA-SE containing Staphylococcus is present in the sample; and c) detecting any signal from the labeled probe thereby detecting the presence or absence of the target amplicon in the combined sample.

In certain embodiments, the labeled probe comprises or consists of SEQ ID NO:12. In some embodiments, the labeled probe is a molecular beacon probe, and wherein the molecular beacon probe comprises a stem that is precisely two base-pairs in length. In other embodiments, the target amplicon comprises or consists of SEQ ID NO:9 or complement thereof.

In particular embodiments, the forward primer comprises a limiting primer and the reverse primer comprises an excess primer, wherein the excess primer is added to the combined sample at a concentration at least five-times (e.g., at least 5× . . . 100× . . . 1000× . . . ) that of the limiting primer, and wherein the amplification conditions comprise asymmetric PCR conditions.

In some embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a femA-SE temperature/temperature signal ratio, wherein a match between the experimental temperature/temperature signal ratio and the femA-SE temperature/temperature signal ratio identifies the presence of femA-SE containing Staphylococcus in the sample.

In some embodiments, compositions are provided comprising at least one (e.g., at least one, at least two, at least three, or at least four) purified nucleic acid sequence, wherein the at least one purified nucleic acid sequence comprises or consists of a sequence selected from the group consisting of: any of SEQ ID NOs:9-12 or complements thereof.

In further embodiments, kits are provided comprising at least two (e.g., at least two, at least three, or at least four) purified nucleic acid sequences, wherein the at least two purified nucleic acid sequences each comprises or consist of a sequence selected from the group consisting of: any of SEQ ID NOs:9-12 or complements thereof.

In particular embodiments, methods are provided of detecting lukF-PV containing Staphylococcus comprising: a) providing: i) a forward primer comprising or consisting of SEQ ID NO:15, ii) a reverse primer comprising or consisting of SEQ ID NO:14, iii) a labeled probe, iv) a sample suspected of containing lukF-PV containing Staphylococcus; b) combining the sample, the labeled probe, the forward primer, and the reverse primer to generate a combined sample and treating the combined sample under amplification conditions such that a target amplicon is generated if the lukF-PV containing Staphylococcus is present in the sample; and c) detecting any signal from the labeled probe thereby detecting the presence or absence of the target amplicon in the combined sample.

In some embodiments, the labeled probe comprises or consists of SEQ ID NO:16. In other embodiments, the labeled probe is a molecular beacon probe, and wherein the molecular beacon probe comprises a stem that is precisely three base-pairs in length. In further embodiments, the target amplicon comprises or consists of SEQ ID NO:13 or complements thereof. In additional embodiments, the forward primer comprises a limiting primer and the reverse primer comprises an excess primer, wherein the excess primer is added to the combined sample at a concentration at least five-times (e.g., 5× . . . 100× . . . 1000× . . . ) that of the limiting primer, and wherein the amplification conditions comprise asymmetric PCR conditions.

In additional embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/ temperature signal ratio with a lukF-PV temperature/temperature signal ratio, wherein a match between the experimental temperature/temperature signal ratio and the lukF-PV temperature/temperature signal ratio identifies the presence of lukF-PV containing *Staphylococcus* in the sample.

In particular embodiments, compositions are provided comprising at least one (e.g., at least one, at least two, at least three, or at least four) purified nucleic acid sequence, wherein the at least one purified nucleic acid sequence comprises or consists of a sequence selected from the group consisting of: any of SEQ ID NOs:13-16 or complements thereof.

In other embodiments, kits are provided comprising at least two (e.g., at least two, at least three, or at least four) purified nucleic acid sequences, wherein the at least two purified nucleic acid sequences each comprises or consist of a sequence selected from the group consisting of: any of SEQ ID NOs:13-16 or complements thereof.

In some embodiments, methods are provided of detecting VanA containing *Staphylococcus* comprising: a) providing: i) a forward primer comprising or consisting of SEQ ID NO:19, ii) a reverse primer comprising or consisting of SEQ ID NO:18, iii) a labeled probe, and iv) a sample suspected of containing VanA containing *Staphylococcus*; b) combining the sample, the labeled probe, the forward primer, and the reverse primer to generate a combined sample and treating the combined sample under amplification conditions such that a target amplicon is generated if the VanA containing *Staphylococcus* is present in the sample; and c) detecting any signal from the labeled probe thereby detecting the presence or absence of the target amplicon in the combined sample.

In further embodiments, the labeled probe comprises or consists of SEQ ID NO:20. In other embodiments, the labeled probe is a molecular beacon probe, and wherein the molecular beacon probe comprises a stem that is precisely two base-pairs in length. In further embodiments, the target amplicon comprises or consists of SEQ ID NO:17 or complement thereof.

In some embodiments, the forward primer comprises a limiting primer and the reverse primer comprises an excess primer, wherein the excess primer is added to the combined sample at a concentration at least five-times (e.g., at least 5× . . . 100× . . . 1000× . . . ) that of the limiting primer, and wherein the amplification conditions comprise asymmetric PCR conditions.

In other embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a VanA temperature/temperature signal ratio, wherein a match between the experimental temperature/temperature signal ratio and the VanA temperature/temperature signal ratio identifies the presence of VanA containing *Staphylococcus* in the sample.

In additional embodiments, compositions are provided comprising at least one (e.g., at least one, at least two, at least three, or at least four) purified nucleic acid sequence, wherein the at least one purified nucleic acid sequence comprises or consists of a sequence selected from the group consisting of: any of SEQ ID NOs:17-20 or complements thereof.

In further embodiments, kits are provided comprising at least two (e.g., at least two, at least three, or at least four) purified nucleic acid sequences, wherein the at least two purified nucleic acid sequences each comprises or consist of a sequence selected from the group consisting of: any of SEQ ID NOs:17-20 or complements thereof.

In some embodiments, methods are provided of detecting lukS-PV containing *Staphylococcus* comprising: a) providing: i) a forward primer comprising or consisting of SEQ ID NO:58, ii) a reverse primer comprising or consisting of SEQ ID NO:57, iii) a labeled probe, iv) a sample suspected of containing lukS-PV containing *Staphylococcus*; b) combining the sample, the labeled probe, the forward primer, and the reverse primer to generate a combined sample and treating the combined sample under amplification conditions such that a target amplicon is generated if the lukS-PV containing *Staphylococcus* is present in the sample; and c) detecting any signal from the labeled probe thereby detecting the presence or absence of the target amplicon in the combined sample.

In certain embodiments, the labeled probe comprises or consists of SEQ ID NO:59. In other embodiments, the labeled probe is a molecular beacon probe, and wherein the molecular beacon probe comprises a stem that is precisely two base-pairs in length. In further embodiments, the target amplicon comprises or consists of SEQ ID NO:56 or complements thereof.

In some embodiments, the forward primer comprises a limiting primer and the reverse primer comprises an excess primer, wherein the excess primer is added to the combined sample at a concentration at least five-times (e.g., 5× . . . 100× . . . 1000× . . . ) that of the limiting primer, and wherein the amplification conditions comprise asymmetric PCR conditions.

In other embodiments, the detecting comprises: i) exposing the combined sample to multiple temperatures that allow the labeled probe to hybridize to the target amplicon and produce temperature-dependent signals; ii) detecting the temperature-dependent signals at least two temperatures; iii) generating an experimental temperature/temperature signal ratio; and iv) comparing the experimental temperature/temperature signal ratio with a lukS-PV temperature/temperature signal ratio, wherein a match between the experimental temperature/temperature signal ratio and the lukS-PV temperature/temperature signal ratio identifies the presence of lukS-PV containing *Staphylococcus* in the sample.

In further embodiments, compositions are provided comprising at least one (e.g., at least one, at least two, at least three, or at least four) purified nucleic acid sequence, wherein the at least one purified nucleic acid sequence comprises or consists of a sequence selected from the group consisting of: any of SEQ ID NOs:56-59 or complements thereof.

In other embodiments, kits are provided comprising at least two (e.g., at least two, at least three, or at least four) purified nucleic acid sequences, wherein the at least two purified nucleic acid sequences, respectively, comprises or consist of a sequence selected from the group consisting of: any of SEQ ID NOs:56-59 or complements thereof.

In some embodiments, methods are provided of detecting bacteria in a sample comprising: a) providing: i) forward primers comprising: a mecA forward primer, a femA-SA forward primer, a femA-SE forward primer, a lukF-PV forward primer, a lukS-PV forward primer, and a VanA forward primer, ii) reverse primers comprising: a mecA reverse primer, a femA-SA reverse primer, a femA-SE reverse primer, a lukF-PV reverse primer, a lukS-PV reverse primer, and a VanA reverse primer, iii) labeled probes comprising: a mecA labeled probe, a femA-SA labeled probe, a femA-SE labeled probe, a lukF-PV labeled probe, a lukS-PV labeled probe, and a VanA labeled probe, iv) a sample suspected of containing a bacteria selected from *S. aureus* and *S. epidermidis*; b) combining the sample, the labeled probe, the forward primer, and the reverse primer to generate a combined sample and treating the combined sample under amplification conditions such that: i) a femA-SA amplicon is generated if the *S. aureus* is present, ii) a femA-SE amplicon is generated if the *S. epidermidis* is present, iii) a mecA amplicon is generated if the bacteria contains a mecA sequence, iv) a lukS-PV amplicon is generated if the bacteria contains a lukS-PV sequence, v) a lukF-PV amplicon is generated if the bacteria contains a lukF-PV sequence, and vi) a VanA amplicon is generated if the bacteria contains a VanA sequence; and c) detecting any signal from the labeled probes thereby detecting the presence or absence of one or more of the femA-SA, femA-SE, mecA, lukS-PV, lukF-PV, and VanA amplicons in the combined sample.

In certain embodiments, the detecting further indicates that the bacteria is not present in the sample, or that one or more of the following is present in the sample: MSSA, MSSE, MRSA, MRSE, VRSA, VRSE, and CA-MRSA. In other embodiments, the labeled probes are molecular beacon probes, and wherein the molecular beacon probes each comprise a stem that is precisely two base-pairs in length or precisely three base-pairs in length.

In further embodiments, the mecA labeled probe comprises or consists of SEQ ID NO: 4, wherein the femA-SA labeled probe comprises or consists of SEQ ID NO:8, wherein the femA-SE labeled probe comprises or consists of SEQ ID NO:12, wherein the lukF-PV labeled probe comprises or consists of SEQ ID NO:16, wherein the lukS-PV labeled probe comprises or consists of SEQ ID NO:59, and wherein the VanA labeled probe comprises or consists of SEQ ID NO:20. In other embodiments, the mecA amplicon comprises or consists of SEQ ID NO:1, wherein the femA-SA amplicon comprises or consists of SEQ ID NO:5, wherein the femA-SE amplicon comprises or consists of SEQ ID NO:9, wherein the lukF-PV amplicon comprises or consists of SEQ ID NO:13, wherein the lukS-PV amplicon comprises or consists of SEQ ID NO:56, and wherein the VanA amplicon comprises or consists of SEQ ID NO:17. In additional embodiments, the mecA forward primer comprises or consists of SEQ ID NO:3, wherein the femA-SA forward primer comprises or consists of SEQ ID NO:7, wherein the femA-SE forward primer comprises or consists of SEQ ID NO:11, wherein the lukF-PV forward primer comprises or consists of SEQ ID NO:15, wherein the lukS-PV forward primer comprises or consists of SEQ ID NO:58, and wherein the VanA forward primer comprises or consists of SEQ ID NO:19. In other embodiments, the mecA reverse primer comprises or consists of SEQ ID NO:2, wherein the femA-SA reverse primer comprises or consists of SEQ ID NO:6, wherein the femA-SE reverse primer comprises or consists of SEQ ID NO:10, wherein the lukF-PV reverse primer comprises or consists of SEQ ID NO:14, wherein the lukS-PV reverse primer comprises or consists of SEQ ID NO:57, and wherein the VanA reverse primer comprises or consists of SEQ ID NO:18.

In other embodiments, the forward primers each comprise a limiting primer and the reverse primers each comprise an excess primer, wherein the excess primers are added to the combined sample at a concentration at least five times (e.g., 5× . . . 25× . . . 100× . . . 1000× . . . ) that of the limiting primers, and wherein the amplification conditions comprise asymmetric PCR conditions.

In some embodiments, the detecting comprises: i) exposing the combined sample to multiple temperatures that allow the labeled probes to hybridize to their corresponding amplicons and produce temperature-dependent signals; ii) detecting the temperature-dependent signals at least two temperatures; iii) generating an experimental temperature/temperature signal ratio; and iv) comparing the experimental temperature/temperature signal ratio with mecA, femA-SA, femA-SE, lukF-PV, lukS-PV, and VanA temperature/temperature signal ratios, wherein a match between the experimental temperature/temperature signal ratio and the mecA, femA-SA, femA-SE, lukF-PV, lukS-PV, and VanA temperature/temperature signal ratios identifies the presence of one or more of the femA-SA, femA-SE, mecA, lukS-PV, lukF-PV, and VanA amplicons in the sample.

In other embodiments, the at least two temperature are 50° C. and 35° C., or any other two temperatures between 70° C. and 25° C. (e.g., 25° C. . . . 53° C. . . . 70° C.). In particular embodiments, the forward primers further comprise a control forward primer; wherein the reverse primers further comprise a control reverse primer; and wherein the labeled probes further comprise a control labeled probe. In additional embodiments, the control forward primer comprises or consists of SEQ ID NO:23, 27, or 31, wherein the control reverse primer comprises or consists of SEQ ID NO:22, 26, or 30, and wherein the control probe comprises or consists of SEQ ID NO:24, 28, or 32.

In some embodiments, the lukS-PVL labeled probe is labeled with FAM dye; wherein the femA-SA and the femA-SE labeled probes are labeled with Cal Orange dye; wherein the vanA and the lukF-PVL labeled probes are labeled with Cal Red dye; and wherein the mecA labeled probe is labeled with Quasar dye.

In additional embodiments, the lukS-PVL labeled probe is labeled with FAM dye; wherein the femA-SA and the vanA labeled probes are labeled with Cal Orange dye; wherein the femA-SE and the lukF-PVL labeled probes are labeled with Cal Red dye; and wherein the mecA labeled probe is labeled with Quasar dye.

In certain embodiments, compositions are provided comprising at least ten (e.g., at least ten . . . at least fifteen . . . or at least twenty) purified nucleic acid sequences, wherein the at least ten purified nucleic acid sequences comprise or consist of a sequence selected from the group consisting of: SEQ ID NOs:2-4, SEQ ID NOs:6-8, SEQ ID NOs:10-12, SEQ ID NOs:14-16, SEQ ID NOs:57-59, SEQ ID NOs:18-20, and SEQ ID NOs:30-32; or complement to any of these sequences.

In some embodiments, kits are provided comprising at least ten (e.g., at least ten . . . at least fifteen . . . or at least twenty) purified nucleic acid sequences, wherein the at least ten purified nucleic acid sequences, respectively, comprise or consist of a sequence selected from the group consisting of: SEQ ID NOs:2-4, SEQ ID NOs:6-8, SEQ ID NOs:10-12, SEQ ID NOs:14-16, SEQ ID NOs:57-59, SEQ ID NOs:18-20, and SEQ ID NOs:30-32, or a complement to any of these sequences.

In further embodiments, methods are provided of detecting bacteria in a sample comprising: a) providing: i) forward primers comprising: a mecA forward primer, a femA-SA forward primer, a femA-SE forward primer, a lukF-PV forward primer, a VanA forward primer, and first, second, and third SCCmec forward primers; ii) reverse primers comprising: a mecA reverse primer, a femA-SA reverse primer, a femA-SE reverse primer, a lukF-PV reverse primer, a VanA reverse primer, and a SCCmec reverse primer; iii) labeled probes comprising: a mecA labeled probe, a femA-SA labeled probe, a femA-SE labeled probe, a lukF-PV labeled probe, a VanA labeled probe, a plurality of SCCmec labeled probes; iv) a sample suspected of containing a bacteria selected from S. aureus and S. epidermidis; b) combining the sample, the labeled probe, the forward primer, and the reverse primer to generate a combined sample and treating the combined sample under amplification conditions such that: i) a femA-SA amplicon is generated if the S. aureus is present, ii) a femA-SE amplicon is generated if the S. epidermidis is present, iii) a mecA amplicon is generated if the bacteria contains a mecA sequence, iv) a lukF-PV amplicon is generated if the bacteria contains a lukF-PV sequence, v) a VanA amplicon is generated if the bacteria contains a VanA sequence, vi) SCCmec type I, type II, type III, type IV, type V, and/or type VII amplicons are generated if the bacteria contains a corresponding SCCmec type I, type II, type III, type IV, type V, or type VII sequence; and c) detecting any signal from the labeled probes thereby detecting the presence or absence of one or more of the femA-SA, femA-SE, mecA, lukF-PV, VanA, SSCmec type I, SSCmec type II, SSCmec type III, SSCmec type IV, SSCmec type V, and SSCmec type VII amplicons in the combined sample.

In certain embodiments, the detecting further indicates that the bacteria is not present in the sample, or that one or more of the following is present in the sample: MSSA, MSSE, MRSA, MRSE, VRSA, VRSE, and MRSA community strain. In other embodiments, the labeled probes are molecular beacon probes, and wherein the molecular beacon probes each comprise a stem that is precisely two base-pairs in length or precisely three base-pairs in length.

In additional embodiments, the mecA labeled probe comprises or consists of SEQ ID NO: 4, wherein the femA-SA labeled probe comprises or consists of SEQ ID NO:8, wherein the femA-SE labeled probe comprises or consists of SEQ ID NO:12, wherein the lukF-PV labeled probe comprises or consists of SEQ ID NO:16, wherein the VanA labeled probe comprises or consists of SEQ ID NO:20, and wherein the SCCmec labeled probe comprises or consists of SEQ ID NO:37. In further embodiments, the mecA amplicon comprises or consists of SEQ ID NO:1, wherein the femA-SA amplicon comprises or consists of SEQ ID NO:5, wherein the femA-SE amplicon comprises or consists of SEQ ID NO:9, wherein the lukF-PV amplicon comprises or consists of SEQ ID NO:13, wherein the VanA amplicon comprises or consists of SEQ ID NO:17, wherein the SSCmec type I amplicon comprises or consists of the complement of SEQ ID NO:38, wherein the SSCmec type II amplicon comprises or consists of the complement of SEQ ID NO:39, wherein the SSCmec type III amplicon comprises or consists of the complement of SEQ ID NO:40, wherein the SSCmec type IV amplicon comprises or consists of the complement of SEQ ID NO:41, wherein the SSCmec type V amplicon comprises or consists of the complement of SEQ ID NO:42, and wherein the SSCmec type VII amplicon comprises or consists of the complement of SEQ ID NO:43.

In further embodiments, the mecA forward primer comprises or consists of SEQ ID NO:3, wherein the femA-SA forward primer comprises or consists of SEQ ID NO:7, wherein the femA-SE forward primer comprises or consists of SEQ ID NO:11, wherein the lukF-PV forward primer comprises or consists of SEQ ID NO:15, wherein the VanA forward primer comprises or consists of SEQ ID NO:19, and wherein the first SCCmec forward primer comprises or consists of SEQ ID NO:33, wherein the second SCCmec forward primer comprises or consists of SEQ ID NO:34, and wherein the third SCCmec forward primer comprises or consists of SEQ ID NO:35.

In other embodiments, the mecA reverse primer comprises or consists of SEQ ID NO:2, wherein the femA-SA reverse primer comprises or consists of SEQ ID NO:6, wherein the femA-SE reverse primer comprises or consists of SEQ ID NO:10, wherein the lukF-PV reverse primer comprises or consists of SEQ ID NO:14, wherein the VanA reverse primer comprises or consists of SEQ ID NO:18, and wherein the SCCmec reverse primer comprises or consists of SEQ ID NO:36.

In particular embodiments, the forward primers each comprise a limiting primer and the reverse primers each comprise an excess primer, wherein the excess primers are added to the combined sample at a concentration at least five-times (e.g., 5× . . . 50× . . . 100× . . . 1000× . . . ) that of the limiting primers, and wherein the amplification conditions comprise asymmetric PCR conditions.

In some embodiments, the detecting comprises: i) exposing the combined sample to multiple temperatures that allow the labeled probes to hybridize to their corresponding amplicons and produce temperature-dependent signals; ii) detecting the temperature-dependent signals at least two temperatures; iii) generating an experimental temperature/temperature signal ratio; and iv) comparing the experimental temperature/temperature signal ratio with mecA, femA-SA, femA-SE, lukF-PV, VanA, SCCmec type I, type II, type III, type IV, type V, and type VII temperature/temperature signal ratios, wherein a match between the experimental temperature/temperature signal ratio and the mecA, femA-SA, femA-SE, lukF-PV, VanA, SCCmec type I, type II, type III, type IV, type V, and/or type VII temperature/temperature signal ratios identifies the presence of one or more of the femA-SA, femA-SE, mecA, lukF-PV, VanA, SCCmec type I, type II, type III, type IV, type V, and/or type VII amplicons in the sample.

In particular embodiments, the at least two temperature are: 48° C. and 35° C. In other embodiments, the SCCmec probe, the femA-SA probe, the femA-SE probe, and the mecA probe are all detected at the 48° C. In additional embodiments, the SCCmec probe, the vanA probe, and the lukF-PVL probe are all detected at the 35° C. In further embodiments, the at least two temperatures are: 50° C., 45° C., 40° C., and 35° C. In other embodiments, the SCCmec probe, the femA-SE probe, and the femA-SA probe are all detected at the 50° C. In further embodiments, the SCCmec probe is detected at the 45° C. In additional embodiments, the SCCmec probe is detected at the 40° C. In other embodiments, the vanA probe, the lukF-PVL probe, and the mecA probe are all detected at the 50° C.

In certain embodiments, the forward primers further comprise a control forward primer; wherein the reverse primers further comprise a control reverse primer; and wherein the labeled probes further comprise a control labeled probe. In particular embodiments, the control forward primer comprises or consists of SEQ ID NO:23, 27, or 31, wherein the control reverse primer comprises or consists of SEQ ID NO:22, 26, or 30, and wherein the control probe comprises or consists of SEQ ID NO:24, 28, or 32.

In some embodiments, the SCCmec labeled probe is labeled with FAM dye; wherein the femA-SA and the vanA labeled probes are labeled with Cal Orange dye; wherein the famA-SE and the lukF-PVL labeled probes are labeled with Cal Red dye; and wherein the mecA labeled probe is labeled with Quasar dye. In further embodiments, a portion of the SCCmec labeled probes are labeled with FAM dye; wherein a portion of the SCCmec labeled probes are labeled with Cal orange dye; wherein the vanA labeled probe is labeled with Cal Orange dye; wherein the femA-SE and the lukF-PVL labeled probes are labeled with Cal Red dye; and wherein the femA-SA and the mecA labeled probes are labeled with Quasar dye.

In particular embodiments, compositions are provided comprising at least ten (e.g., at least ten . . . at least fifteen . . . or at least twenty) purified nucleic acid sequence, wherein the at least ten purified nucleic acid sequences comprises or consists of a sequence selected from the group consisting of: SEQ ID NOs:2-4, SEQ ID NOs:6-8, SEQ ID NOs:10-12, SEQ ID NOs:14-16, SEQ ID NOs:33-37, SEQ ID NOs: 18-20, and SEQ ID NOs:30-32, or any of the complements thereof.

In some embodiments, kits are provided comprising at least ten (e.g., at least ten . . . at least fifteen . . . or at least twenty) purified nucleic acid sequences, wherein the at least ten purified nucleic acid sequences each comprises or consist of a sequence selected from the group consisting of: SEQ ID NOs:2-4, SEQ ID NOs:6-8, SEQ ID NOs:10-12, SEQ ID NOs:14-16, SEQ ID NOs:33-37, SEQ ID NOs: 18-20, and SEQ ID NOs:30-32, or any of the complements thereof.

DESCRIPTION OF THE FIGURES

FIG. 15 shows results from an exemplary MRSA type 1 assay from Example 1.

FIG. 20 shows results from an exemplary MRSA type 3 assay from Example 1. FIG. 20A shows full LATE-PCR multiplex endpoint ratio fluorescence showing control targets. FIG. 20B shows full LATE-PCR multiplex endpoint ratio fluorescence showing MSSA target. FIG. 20C shows full LATE-PCR multiplex endpoint ratio fluorescence showing MSSE target. FIG. 20D shows full LATE-PCR multiplex endpoint ratio fluorescence showing HA-MRSA1 target. FIG. 20E shows full LATE-PCR multiplex endpoint ratio fluorescence showing HA-MRSA2 target. FIG. 20F shows full LATE-PCR multiplex endpoint ratio fluorescence showing HA-MRSA3 target. FIG. 20G shows full LATE-PCR multiplex endpoint ratio fluorescence showing HA-MRSA4 target. FIG. 20H shows full LATE-PCR multiplex endpoint ratio fluorescence showing HA-MRSA5 target. FIG. 20I shows full LATE-PCR multiplex endpoint ratio fluorescence showing HA-MRSA7 target. FIG. 20J shows full LATE-PCR multiplex endpoint ratio fluorescence showing CA-MRSA2 target.

FIG. 21 shows results from an exemplary MRSA type 3 assay from Example 1. FIG. 21A shows full LATE-PCR multiplex at 3 endpoint ratios fluorescence showing SCCmec cassette targets. FIG. 21B shows full LATE-PCR multiplex at 3 endpoint ratios fluorescence showing SCCmec cassette targets. FIG. 21C shows full LATE-PCR multiplex endpoint ratios fluorescence showing vanA and femA-SA targets. FIG. 21D shows full LATE-PCR multiplex endpoint ratios fluorescence showing lukF-PVL and femA-SE targets.

DEFINITIONS

Figure 1:
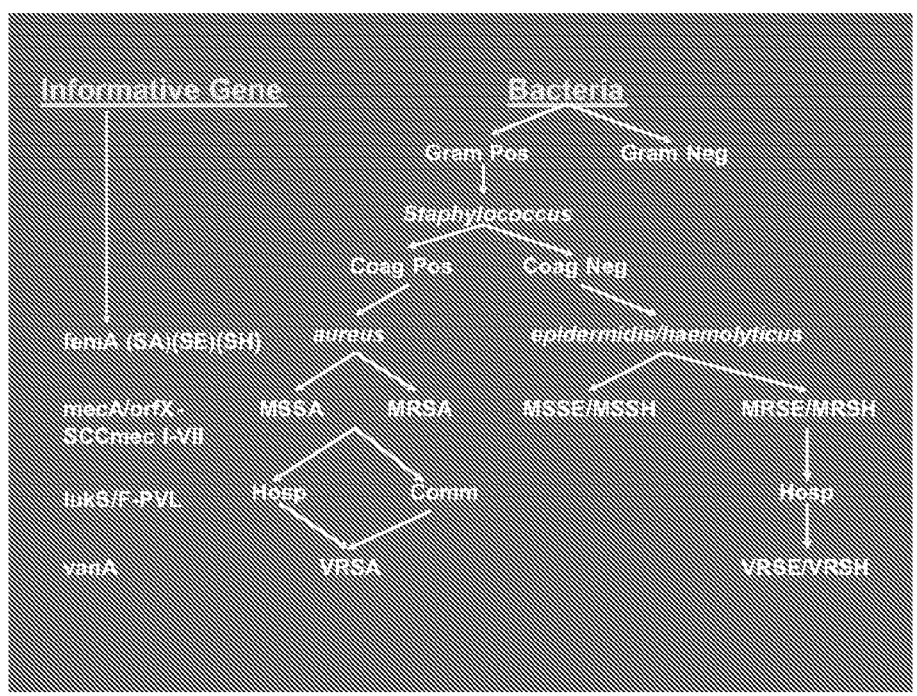
FIG. 1A shows the regions or regions that can be used to distinguish different bacteria types, including *S. aureus* vs. *epidermidis/heamolyticus*; MSSA vs. MRSA; hospital acquired vs. community acquired, and VRSA.
FIG. 1B shows 42 possible outcomes that are possible with certain embodiments of the *Staphylococcus* detection assays provided herein.

As used herein, the phrase "probe hybridization sequence" is used is reference to a particular target sequence and a particular probe, and it is the sequence in the target sequence that hybridizes to the particular probe. The probe may be fully or partially complementary to the target sequence over the length of the probe hybridization sequence. However, the 5' and 3' terminal bases in the probe hybridization sequence are exactly complementary the probe (i.e., there are not mis-matches at the 5' and 3' terminal ends of the probe hybridization sequence).

A "molecular beacon probe" is a single-stranded oligonucleotide, typically 25 to 35 bases-long, in which the bases on the 3' and 5' ends are complementary forming a "stem," typically for 5 to 8 base pairs. In certain embodiments, the molecular beacons employed have stems that are exactly 2 or 3 base pairs in length. A molecular beacon probe forms a hairpin structure at temperatures at and below those used to anneal the primers to the template (typically below about 60° C.). The double-helical stem of the hairpin brings a fluorophore (or other label) attached to the 5' end of the probe very close to a quencher attached to the 3' end of the probe. The probe does not fluoresce (or otherwise provide a signal) in this conformation. If a probe is heated above the temperature needed to melt the double stranded stem apart, or the probe is allowed to hybridize to a target oligonucleotide that is complementary to the sequence within the single-strand loop of the probe, the fluorophore and the quencher are separated, and the fluorophore fluoresces in the resulting conformation. Therefore, in a series of PCR cycles the strength of the fluorescent signal increases in proportion to the amount of the beacon hybridized to the amplicon, when the signal is read at the annealing temperature. Molecular beacons with different loop sequences can be conjugated to different fluorophores in order to monitor increases in amplicons that differ by as little as one base (Tyagi, S. and Kramer, F. R. (1996), Nat. Biotech. 14:303 308; Tyagi, S. et al., (1998), Nat. Biotech. 16: 49 53; Kostrikis, L. G. et al., (1998), Science 279: 1228 1229; all of which are herein incorporated by reference).

As used herein, the term "amplicon" refers to a nucleic acid generated using primer pairs, such as those described herein. The amplicon is typically single-stranded DNA (e.g., the result of asymmetric amplification), however, it may be RNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. In certain embodiments, the type of amplification is asymmetric PCR (e.g., LATE-PCR) which is described in, for example, U.S. Pat. No. 7,198,897 and Pierce et al., PNAS, 2005, 102(24):8609-8614, both of which are herein incorporated by reference in their entireties. In particular embodiments, LATE-PCR is employed using multiple endpoint temperature detection (see, e.g., U.S. Pat. Pub. 2006/0177841 and Sanchez et al., BMC Biotechnology, 2006, 6:44, pages 1-14, both of which are herein incorporated by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This may be importance in amplification reactions, as well as detection methods that depend upon binding between nucleic acids.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_M$) of the formed hybrid, and the G:C ratio within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference in its entirety.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

In some embodiments, the oligonucleotide primer pairs described herein can be purified. As used herein, "purified oligonucleotide primer pair," "purified primer pair," or "purified" means an oligonucleotide primer pair that is chemically-synthesized to have a specific sequence and a specific number of linked nucleosides. This term is meant to explicitly exclude nucleotides that are generated at random to yield a mixture of several compounds of the same length each with randomly generated sequence. As used herein, the term "purified" or "to purify" refers to the removal of one or more components (e.g., contaminants) from a sample.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68: 90-99; the phosphodiester method of Brown et al. (1979) *Meth Enzymol.* 68: 109-151; the diethylphosphoramidite method of Beaucage et al. (1981) *Tetrahedron Lett.* 22: 1859-1862; the triester method of Matteucci et al. (1981) *J Am Chem Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference in their entireties.

As used herein a "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, etc.) from one or more bioagents, such as MRSA. Samples can include, for example, blood, saliva, urine, feces, anorectal swabs, vaginal swabs, cervical swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxygenin; luminogenic, phosphorescent or fluorogenic moieties; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246:300, each incorporated herein by reference in its entirety). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In some embodiments, the emission spectrum of the acceptor dye is distinct from the emission spectrum of the donor dye such that emissions from the dyes can be differentiated (e.g., spectrally resolved) from each other.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral.

"$T_M$," or "melting temperature," of an oligonucleotide describes the temperature (in degrees Celsius) at which 50% of the molecules in a population of a single-stranded oligonucleotide are hybridized to their complementary sequence and 50% of the molecules in the population are not-hybridized to said complementary sequence. The $T_M$ of a primer or probe can be determined empirically by means of a melting curve. In some cases it can also be calculated. For the design of symmetric and asymmetric PCR primer pairs, balanced $T_M$'s are generally calculated by one of the three methods discussed earlier, that is, the "% GC", or the "2(A+T) plus 4 (G+C)", or "Nearest Neighbor" formula at some chosen set of conditions of monovalent salt concentration and primer concentration. In the case of Nearest Neighbor calculations the $T_M$'s of both primers will depend on the concentrations chosen for use in calculation or measurement, the difference between the $T_M$'s of the two primers will not change substantially as long as the primer concentrations are equimolar, as they normally are with respect to PCR primer measurements and calculations. $T_M[1]$ describes the calculated $T_M$ of a PCR primer at particular standard conditions of 1 micromolar (1 uM=10$^{-6}$M) primer concentration, and 0.07 molar monovalent cations. In this application, unless otherwise stated, $T_M[1]$ is calculated using Nearest Neighbor formula, $T_M=\Delta H/(\Delta S+R \ln(C/2))-273.15+12 \log [M]$. This formula is based on the published formula (Le Novere, N. (2001), "MELTING, Computing the Melting Temperature of Nucleic Acid Duplex," Bioinformatics 17: 1226 7). $\Delta H$ is the enthalpy and $\Delta S$ is the entropy (both $\Delta H$ and $\Delta S$ calculations are based on Allawi and SantaLucia, 1997), C is the concentration of the oligonucleotide (10$^{-6}$M), R is the universal gas constant, and [M] is the molar concentration of monovalent cations (0.07). According to this formula the nucleotide base composition of the oligonucleotide (contained in the terms $\Delta H$ and $\Delta S$), the salt concentration, and the concentration of the oligonucleotide (contained in the term C) influence the $T_M$. In general for oligonucleotides of the same length, the $T_M$ increases as the percentage of guanine and cytosine bases of the oligonucleotide increases, but the $T_M$ decreases as the concentration of the oligonucleotide decreases. In the case of a primer with nucleotides other than A, T, C and G or with covalent modification, $T_M[1]$ is measured empirically by hybridization melting analysis as known in the art.

"$T_M[0]$" means the $T_M$ of a PCR primer or probe at the start of a PCR amplification taking into account its starting concentration, length, and composition. Unless otherwise stated, $T_M[0]$ is the calculated $T_M$ of a PCR primer at the actual starting concentration of that primer in the reaction mixture, under assumed standard conditions of 0.07 M monovalent cations and the presence of a vast excess concentration of a target oligonucleotide having a sequence complementary to that of the primer. In instances where a target sequence is not fully complementary to a primer it is important to consider not only the $T_M[0]$ of the primer against its complements but also the concentration-adjusted melting point of the imperfect hybrid formed between the primer and the target. In this application, $T_M[0]$ for a primer is calculated using the Nearest Neighbor formula and conditions stated in the previous paragraph, but using the actual starting micromolar concentration of the primer. In the case of a primer with nucleotides other than A, T, C and G or with covalent modification, $T_M[0]$ is measured empirically by hybridization melting analysis.

As used herein superscript X refers to the Excess Primer, superscript L refers to the Limiting Primer, superscript A refers to the amplicon, and superscript P refers to the probe.

$T_M^A$ means the melting temperature of an amplicon, either a double-stranded amplicon or a single-stranded amplicon hybridized to its complement. In this application, unless otherwise stated, the melting point of an amplicon, or $T_M^A$, refers to the $T_M$ calculated by the following % GC formula: $T_M^A=81.5+0.41(\% \text{ G}+\% \text{ C})-500/L+16.6 \log [M]/(1+0.7[M])$, where L is the length in nucleotides and [M] is the molar concentration of monovalent cations.

$T_M[0]^P$ refers to the concentration-adjusted melting temperature of the probe to its target, or the portion of probe that actually is complementary to the target sequence (e.g., the loop sequence of a molecular beacon probe). In the case of most linear probes, $T_M[0]^P$ is calculated using the Nearest Neighbor formula given above, as for $T_M[0]$, or preferably is measured empirically. In the case of molecular beacons, a rough estimate of $T_M[0]^P$ can be calculated using commercially available computer programs that utilize the % GC method, see Marras, S. A. et al. (1999) "Multiplex Detection of Single-Nucleotide Variations Using Molecular Beacons," Genet. Anal. 14:151 156, or using the Nearest Neighbor formula, or preferably is measured empirically. In the case of probes having non-conventional bases and for double-stranded probes, $T_M[0]^P$ is determined empirically.

$C_T$ means threshold cycle and signifies the cycle of a real-time PCR amplification assay in which signal from a reporter indicative of amplicons generation first becomes detectable above background. Because empirically measured background levels can be slightly variable, it is standard practice to measure the $C_T$ at the point in the reaction when the signal reaches 10 standard deviations above the background level averaged over the 5-10 preceding thermal cycles.

DETAILED DESCRIPTION

Provided herein are methods, kits, and compositions related to nucleic acid detection assays that allow discrimination of multiple target sequences with a single probe. In particular, provided herein are methods kits, and compositions that include single-probe target sequence discrimination where different target amplicons may have identical probe hybridization sequences by employing multiple temperature end-point signal probe detection. Also provided herein are methods, kits, and compositions for distinguishing between two or more target amplicons using multiple-temperature end-point probe detection. In certain embodiments, asymmetric PCR amplification methods are employed (e.g., LATE-PCR amplification).

Work conducted during the development of embodiments described herein demonstrated that polymorphic nucleic acid targets could be detected with a single probe, even where the probe hybridization site on two or more polymorphic targets was identical. This finding is surprising as the art has relied on the use of different probes for different target sequences, or the use of single probe where the probe hybridization site is different (see, e.g., Sanchez et al., BMC Biotechnology, 2006, 6:44, pages 1-14, and U.S. Pat. Pub. 2006/0177841; both of which are herein incorporated by reference). While not limited to any particular mechanism, and an understanding of the mechanism is not necessary to practice the methods, compositions, and kits provided herein, it is believed that targets with identical probe hybridization regions can be distinguished based on the secondary structure of the target sequences.

While the polymorphic target sequences in embodiments of the assays have identical probe hybridization sites, such sequences do not have complete sequence identity (e.g., amplicons from two or more target sequences do not have complete sequence identity). Base differences between different target sequence amplicons may be located adjacent to the probe hybridization site, e.g., immediately adjacent, or may be further away near the 5' and 3' ends. Such base differences, it has been discovered, cause a single probe to have a different melting temperature for the probe hybridization site present on two or more target sequences. The melting temperature differences can be employed to distinguish different target sequences with a single probe, even though they have identical probe hybridization sites. Preferably, the melting or annealing of the probe to different target amplicons is measured at least two different temperatures along a melting or binding curve such that a temperature/temperature signal ratio is generated. Different target sequences, while potentially very similar in sequence, and identical at the probe hybridization site for a given probe, will have different, characteristic, temperature/temperature signal ratios. Such differences in temperature/temperature signal ratios allows such polymorphic target sequences to be distinguished with a single labeled probe.

In certain embodiments, the assays described herein employ primer pairs to amplify target nucleic acid sequences. The methods described herein are not limited by the type of amplification that is employed. In certain embodiments, asymmetric PCR is employed, such as LATE-PCR.

PCR is a repeated series of steps of denaturation, or strand melting, to create single-stranded templates; primer annealing; and primer extension by a thermally stable DNA polymerase such as Thermus aquaticus (Taq) DNA polymerase. A typical three-step PCR protocol (see Innis et al., Chapter 1) may include denaturation, or strand melting, at 93-95 degrees C. for more than 5 sec, primer annealing at 55-65 degrees C. for 10-60 sec, and primer extension for 15-120 sec at a temperature at which the polymerase is highly active, for example, 72 degrees C. for Taq DNA polymerase. A typical two-step PCR protocol may differ by having the same temperature for primer annealing as for primer extension, for example, 60 degrees C. or 72 degrees C. For either three-step PCR or two-step PCR, an amplification involves cycling the reaction mixture through the foregoing series of steps numerous times, typically 25-40 times. During the course of the reaction the times and temperatures of individual steps in the reaction may remain unchanged from cycle to cycle, or they may be changed at one or more points in the course of the reaction to promote efficiency or enhance selectivity. In addition to the pair of primers and target nucleic acid a PCR reaction mixture typically contains each of the four deoxyribonucleotide 5' triphosphates (dNTPs) at equimolar concentrations, a thermostable polymerase, a divalent cation, and a buffering agent. A reverse transcriptase is included for RNA targets, unless the polymerase possesses that activity. The volume of such reactions is typically 25-100 ul. Multiple target sequences can be amplified in the same reaction. In the case of cDNA amplification, PCR is preceded by a separate reaction for reverse transcription of RNA into cDNA, unless the polymerase used in the PCR possesses reverse transcriptase activity. The number of cycles for a particular PCR amplification depends on several factors including: a) the amount of the starting material, b) the efficiency of the reaction, and c) the method and sensitivity of detection or subsequent analysis of the product. Cycling conditions, reagent concentrations, primer design, and appropriate apparatuses for typical cyclic amplification reactions are known (see, for example, Ausubel, F. Current Protocols in Molecular Biology (1988) Chapter 15: "The Polymerase Chain Reaction," J. Wiley (New York, N.Y. (USA)).

In an idealized example, each strand of each amplicon molecule binds a primer at one end and serves as a template for a subsequent round of synthesis. The rate of generation of primer extension products, or amplicons, is thus generally exponential, theoretically doubling during each cycle. The amplicons include both plus (+) and minus (−) strands, which hybridize to one another to form double strands. To differentiate typical PCR from special variations described herein, typical PCR is referred to as "symmetric" PCR. Symmetric PCR thus results in an exponential increase of one or more double-stranded amplicon molecules, and both strands of each amplicon accumulate in equal amounts during each round of replication. The efficiency of exponential amplification via symmetric PCR eventually declines, and the rate of amplicon accumulation slows down and stops. Kinetic analysis of symmetric PCR reveals that reactions are composed of: a) an undetected amplification phase (initial cycles) during which both strands of the target sequence increase exponentially, but the amount of the product thus far accumulated is below the detectable level for the particular method of detection in use; b) a detected amplification phase (additional cycles) during which both strands of the target sequence continue to increase in parallel and the amount of the product is detectable; c) a plateau phase (terminal cycles) during which synthesis of both strands of the amplicon gradually stops and the amount of product no longer increases. Symmetric reactions slow down and stop because the increasing concentrations of complementary amplicon strands hybridize to each other (reanneal), and this out-competes the ability of the separate primers to hybridize to their respective target strands. Typically reactions are run long enough to guarantee accumulation of a detectable amount of product, without regard to the exact number of cycles needed to accomplish that purpose.

A technique that has found limited use for making single-stranded DNA directly in a PCR reaction is "asymmetric PCR." Gyllensten and Erlich, "Generation of Single-Stranded DNA by the polymerase chain reaction and its application to direct sequencing of the HLA-DQA Locus," Proc. Natl. Acad. Sci. (USA) 85: 7652 7656 (1988); Gyllensten, U. B. and Erlich, H. A. (1991) "Methods for generating single stranded DNA by the polymerase chain reaction" U.S. Pat. No. 5,066,584, Nov. 19, 1991; all of which are herein incorporated by reference in their entireties. Asymmetric PCR differs from symmetric PCR in that one of the primers is added in limiting amount, typically $1/100$th to $1/5$th of the concentration of the other primer. Double-stranded amplicon accumulates during the early temperature cycles, as in symmetric PCR, but one primer is depleted, typically after 15-25 PCR cycles, depending on the number of starting templates. Linear amplification of one strand takes place during subsequent cycles utilizing the undepleted primer. Primers used in asymmetric PCR reactions reported in the literature, including the Gyllensten patent, are often the same primers for use in symmetric PCR. Poddar (Poddar, S. (2000) "Symmetric vs. Asymmetric PCR and Molecular Beacon Probe in the Detection of a Target Gene of Adenovirus," Mol. Cell Probes 14: 25 32 compared symmetric and asymmetric PCR for amplifying an adenovirus substrate by an end-point assay that included 40 thermal cycles. He reported that a primers ratio of 50:1 was optimal and that asymmetric PCR assays had better sensitivity that, however, dropped significantly for dilute substrate solutions that presumably contained lower numbers of target molecules. In some embodiments, asymmetric PCR is used with embodiments of the assays described herein.

In certain embodiments, an amplification method is used that is known as "Linear-After-The Exponential PCR" or, for short, "LATE-PCR." LATE-PCR is a non-symmetric PCR method; that is, it utilizes unequal concentrations of primers and yields single-stranded primer-extension products, or amplicons. LATE-PCR includes innovations in primer design, in temperature cycling profiles, and in hybridization probe design. Being a type of PCR process, LATE-PCR utilizes the basic steps of strand melting, primer annealing, and primer extension by a DNA polymerase caused or enabled to occur repeatedly by a series of temperature cycles. In the early cycles of a LATE-PCR amplification, when both primers are present, LATE-PCR amplification amplifies both strands of a target sequence exponentially, as occurs in conventional symmetric PCR. LATE-PCR then switches to synthesis of only one strand of the target sequence for additional cycles of amplification. In certain real-time LATE-PCR assays, the limiting primer is exhausted within a few cycles after the reaction reaches its $C_T$ value, and in the certain assays one cycle after the reaction reaches its $C_T$ value. As defined above, the $C_T$ value is the thermal cycle at which signal becomes detectable above the empirically determined background level of the reaction. Whereas a symmetric PCR amplification typically reaches a plateau phase and stops generating new amplicons by the 50th thermal cycle, LATE-PCR amplifications do not plateau and continue to generate single-stranded amplicons well beyond the 50th cycle, even through the 100th cycle. LATE-PCR amplifications and assays typically include at least 60 cycles, preferably at least 70 cycles when small (10,000 or less) numbers of target molecules are present at the start of amplification.

With certain exceptions, the ingredients of a reaction mixture for LATE-PCR amplification are generally the same as the ingredients of a reaction mixture for a corresponding symmetric PCR amplification. The mixture typically includes each of the four deoxyribonucleotide 5' triphosphates (dNTPs) at equimolar concentrations, a thermostable polymerase, a divalent cation, and a buffering agent. As with symmetric PCR amplifications, it may include additional ingredients, for example reverse transcriptase for RNA targets. Non-natural dNTPs may be utilized. For instance, dUTP can be substituted for dTTP and used at 3 times the concentration of the other dNTPs due to the less efficient incorporation by Taq DNA polymerase.

In certain embodiments, the starting molar concentration of one primer, the "Limiting Primer," is less than the starting molar concentration of the other primer, the "Excess Primer." The ratio of the starting concentrations of the Excess Primer and the Limiting Primer is generally at least 5:1, preferably at least 10:1, and more preferably at least 20:1. The ratio of Excess Primer to Limiting Primer can be, for example, 5:1 . . . 10:1, 15:1 . . . 20:1 . . . 25:1 . . . 30:1 . . . 35:1 . . . 40:1 . . . 45:1 . . . 50:1 . . . 55:1 . . . 60:1 . . . 65:1 . . . 70:1 . . . 75:1 . . . 80:1 . . . 85:1 . . . 90:1 . . . 95:1 . . . or 100:1 . . . 1000:1 . . . or more. Primer length and sequence are adjusted or modified, preferably at the 5' end of the molecule, such that the concentration-adjusted melting temperature of the Limiting Primer at the start of the reaction, $T_M[0]^L$, is greater than or equal (plus or minus 0.5 degrees C.) to the concentration-adjusted melting point of the Excess Primer at the start of the reaction, $T_M[0]^X$. Preferably the difference $(T_M[0]^L - T_M[0]^X)$ is at least +3, and more preferably the difference is at least +5 degrees C.

Amplifications and assays according to embodiments of methods described herein can be performed with initial reaction mixtures having ranges of concentrations of target molecules and primers. LATE-PCR assays are particularly suited for amplifications that utilize small reaction-mixture volumes and relatively few molecules containing the target sequence, sometimes referred to as "low copy number." While LATE-PCR can be used to assay samples containing large amounts of target, for example up to $10^6$ copies of target molecules, other ranges that can be employed are much smaller amounts, from to 1-50,000 copies, 1-10,000 copies and 1-1,000 copies. In certain embodiments, the concentration of the Limiting Primer is from a few nanomolar (nM) up to 200 nM. The Limiting Primer concentration is preferably as far toward the low end of the range as detection sensitivity permits.

As with PCR, either symmetric or asymmetric, LATE-PCR amplifications include repeated thermal cycling through the steps of strand melting, primer annealing and primer extension. Temperatures and times for the three steps are typically, as with symmetric PCR, 93-95 degrees C. for at least 5 sec for strand melting, 55-65 degrees C. for 10-60 sec for annealing primers, and 72 degrees C. for 15-120 sec for primer extension. For 3-step PCR amplifications, primer annealing times are generally in the range of 10-20 sec. Variations of temperature and time for PCR amplifications are known to persons skilled in the art and are generally applicable to LATE-PCR as well. For example, so-called "2-step" PCR, in which one temperature is used for both primer annealing and primer extension, can be used for LATE-PCR. In the case of "2-step" reactions the combined annealing-extension step can be longer than 30 sec, but preferably as short as possible and generally not longer that 120 sec.

Design of primer pairs for use in LATE-PCR can be performed directly, as will be explained. Alternatively, it can begin with selecting or designing a primer pair for symmetric PCR by known methods, followed by modifications for LATE-PCR. In general, symmetric PCR primers are designed to have equal melting points at some set of standard conditions of primers concentration and salt concentration. Symmetric PCR primers are conveniently designed and analyzed utilizing an available computer program. For symmetric and asymmetric PCR the standard techniques for calculating melting temperatures ($T_M$) have been the "Nearest Neighbor" method and the "2(A+T)+4 (G+C)" method. As discussed above, $T_M[1]$ which is the $T_M$ of the primer at a standard primer concentration of 1 uM and 0.07M salt (monovalent cations). Conversion from the $T_M$ given by a typical computer program to $T_M[1]$ generally has minimal effect on the relationship of the $T_M$'s of a primer pair. For the concentration-adjusted melting temperatures of primer pairs in embodiments described herein, either actual measurement or an appropriate calculation is generally required.

In practice, once a particular target sequence (for instance a sequence flanking a mutation within a gene) has been chosen for amplification, several candidate pairs of equal $T_M$ primers are designed via a computer program such as Oligo 6.0® using the program's default values. The candidate primer pairs can then be scrutinized on the basis of additional criteria, such as possible primer-dimer formation, that are known in the art to cause non-desirable primer qualities. Satisfactory pairs of candidate primers are further scrutinized using software such as "Blast" for possible non-specific matches to DNA sequences elsewhere in the known genome from the species of the target sequence (Madden, T. L. et al. (1996) "Applications of Network BLAST Server," Meth. Enzymol. 266: 131 141). Primers pairs are then compared as to their $T_M[0]$ values at several different possible concentrations and ratios such that the primer chosen to be the Limiting Primer will have an equal or greater $T_M[0]$ relative to the primer chosen to be the Excess Primer. In addition, pairs of candidate primers are examined in relation to the sequence of the amplicon they are expected to generate. For instance, certain target sequences may contain a GC-rich sequence at one end and a less GC-rich sequence at the other end. Where that occurs, choosing the Limiting Primer sequence within sequences at the GC-rich end will assist in achieving a higher melting point for the Limiting Primer relative to the Excess Primer, which will consists of sequences in the less GC-rich end. Examination of the candidate primer pairs relative to the amplicon sequence may suggest additional or different ways of modifying the sequences of one or both members of the pair, such as deliberately increasing or decreasing the length of the primer, most preferably at its 5' end, or introducing changes in base sequences within the primer which deliberately cause it to mismatch with its target in small regions. All such changes will increase or decrease the $T_M[0]$ of either the Limiting or Excess primer.

EXAMPLES

The following Examples are presented in order to provide certain exemplary embodiments of the assays described herein and are not intended to limit the scope thereof.

Example 1

Monoplex and Multiplex Detection of *Staphylococcus aureus*

This Example describes various monoplex and multiplex *S. aureus* detection assays using a form of asymmetric PCR called LATE-PCR, as well as multiple temperature end point reads designed to generate temperature/temperature signal ratios. The genes or regions that can be used to distinguish different bacteria types are shown in FIG. 1A. The assays shown in the Example below identify both Methicillin-susceptible *Staphylococcus aureus* (MSSA) and Methicillin-resistant *Staphylococcus aureus* (MRSA), by femA-SA, mecA, and orfX-SCCmec gene detection, as well as differentiate Staph A from other coagulase negative Staph. For example, *Staphylococcus epidermidis*, MSSE and MRSE are distinguished via femA-SE gene detection. In order to distinguish hospital acquired HA-MRSA from community acquired MRSA (CA-MRSA), the PVL toxin genes lukF-PVL or lukS-PVL are employed. Vancomycin resistance in MRSA is distinguished using the vanA gene. Table 1 shows the various amplification targets and putative result(s).

TABLE 1

| Amplification target | Putative result |
|---|---|
| femA-SA. | MSSA |
| femA-SA, mecA, orfX-SCCmec I-VII | MRSA |
| femA-SA, orfX-SCCmec I-VII | MSSA (SCCmec I-VII inserted, mecA excised) |
| femA-SE | MSSE |
| femA-SE, mecA | MRSE |
| femA-SA/femA-SE | MSSA vs. MSSE mixture: |
| femA-SA, lukF-PVL | CA-MSSA |
| femA-SA, orfX-SCCmec I-VII, mecA, lukF-PVL | CA-MRSA |
| femA-SA, orfX-SCCmec I-VII, mecA, vanA | VRSA |
| femA-SE, mecA, vanA | VRSE |
| Controls only | No bacteria |

The genes of interest in the assays below, as shown in FIG. 1A, are femA, mecA, lukF-PVL, vanA, and the SCCmec-orfX boundary. With the full multi-plex of all of these targets, there are 42 possible outcomes, as shown in FIG. 1B. Detection of these genes allows for a wide target differentiation, for example, in a single multiplex assay. In some cases the sequence differences of a gene are used to differentiate two different distinct targets. The various gene/region targets are reviewed below.

The femA gene is used as the main criteria for detection and differentiation between *Staphylococcus aureus* and *Staphylococcus epidermidis*. The mecA gene is used to distinguish Methicillin-susceptible *Staphylococcus aureus* (MSSA) and Methicillin-resistant *Staphylococcus aureus* (MRSA). The mecA gene is located in the SCCmec cassette and can also 'pop-out' of the cassette leaving the cassette behind in the organism and rendering the bacteria once again susceptible to Methicillin. The lukF-PVL gene is an indicator of a deadly toxin that can be incorporated into the *S. aureus* bacteria and is usually associated with the a community acquired strain of *S. aureus* and not the hospital acquired type. It can be incorporated into MSSA and MRSA. The vanA gene determines resistance to vancomycin, one of the last line antibiotics for the treatment of *S. aureus* infections. The vanA gene is also found in other bacteria specifically enterococci faecalis and faecium. The SCCmec cassette carries the mecA gene and therefore when it inserted in *S. aureus* it confers resistance to methicillin antibiotics. The SCCmec is inserted at the 3' end of the orfX gene. The orfX gene is highly conserved while the SCCmec cassettes are not and have been described in the literature as having I-VII distinct types and sub-types to each of the main varieties. The assay described in the Examples below is designed to detect each of the SCCmec types and determine the SCCmec type present in the organism. This result is accomplished using three different limiting primers that are located in the SCCmec sequence and a single excess primer and probe located in the conserved orfX sequence. The $T_M$ of the limiting primers vary from 66° C. to 50° C. depending on sequence variation. The probe has a single mismatch for several of the SCCmec types.

Material and Methods

The following materials and methods are used for the assays described below. Table 2 provides the forward/limiting, reverse/excess, target amplicon, and probe sequences used to detect the above discussed targets. In Table 2, in the various amplicons, the excess/reverse primer sequence, probe hybridization sequence, and complement of limiting primer are all underlined. The probes in Table 2 (molecular beacon probes) are shown with the hybridization portion of the probe underlined, and the part of the probe that forms the "stem" of the molecular beacon non-underlined.

TABLE 2

| Name | Sequence | SEQ ID NO: | Bases | $T_M$ ° C. |
|---|---|---|---|---|
| mecA amplicon | CTGATTAACCCAGTACAGATCCTTTCAATCTATAGC GCATTAGAAAATAATGGCAATATTAACGCACCTCAC TTATTAAAAGACACTTAATTGGCAAATCCGGTACTG CAGAACTC | 1 | 116 | 80.0 |
| mecA excess primer | CTGATTAACCCAGTACAGATCCT | 2 | 23 | 65.3 |
| mecA limiting primer | GAGTTCTGCAGTACCGGATTTGCCA | 3 | 24 | 68.5 |
| mecA probe | Quasar-AAGAGGTGCGTTAATATTGCTT-BHQ2 | 4 | 22 | 58.7 |
| femA-SA amplicon | CGTTGTCTATACCTACATATCGATCCATATTTACCA TATCAATACTTGAATCATGATGGCGAGATTACAGGT AATTGATAAAATGAGTAACTTAGGATTTGAACATAC TGGATTCC | 5 | 116 | 78.6 |
| femA-SA excess primer | CGTTGTCTATACCTACATATCGATCC | 6 | 26 | 65.5 |
| femA-SA Limiting primer | GGAATCCAGTATGTTCAAATCCTAAGTTACTCATT | 7 | 35 | 67.0 |
| femA-SA probe | Cal Org-AACCTGTAATCTCGCCATT-BHQ1 | 8 | 19 | 58.4 |
| femA-SE amplicon | TAAGAGTTGACCCATACCTTCCATATCAATATTTAA ATCAGGGAGAAATAACTGGAAATGCAGGTCATGATT GGATTTTTGATGAATTAGAGAGTTTAGGATATAAAC ACGAAGGATTCC | 9 | 120 | 78.3 |
| femA-SE Excess primer | TAAGAGTTGACCCATACCTTCC | 10 | 22 | 64.9 |
| femA-SE Limiting primer | GGAATCCTTCGTGTTTATATCCTAAACTCTCTAATT CATC | 11 | 40 | 67.9 |
| femA-SE probe | Cal Red- ATTTTCCAGTTATTTCTCCCTAT -BHQ2 | 12 | 23 | 56.9 |
| lukF-PV amplicon | GGCAGAGATAGTTATCATTCAACTTATGGTAATGAA ATGTTTTTAGGCTAAGACAAAGCAACTTAAATGCT GGACAAAACTTCTTGGAATATCACAAAATGCCAGTG TTATCCAGAGG | 13 | 119 | 79.4 |
| lukF-PV Excess Primer | GGCAGAGATAGTTATCATTCAACTTAT | 14 | 27 | 64.4 |
| lukF-PV Limiting Primer | CCTCTGGATAACACTGGCATTTTGTGATATTCC | 15 | 33 | 69.0 |

TABLE 2-continued

| Name | Sequence | SEQ ID NO: | Bases | T$_M$ °C. |
|---|---|---|---|---|
| lukF-PV probe | Cal Red-TAGTTGCTTTGTCTA-BHQ2 | 16 | 15 | 46.5 |
| lukS-PV amplicon | GAGGTGGCCTTTCCAATACAATATTGGTCTCAAAAC AAATGACCCCAATGTAGATTTAATAAATTATCTACC TAAAAATAAAATAGATTCAGTAAATGTTAGTCAAAC ATTAGGTTATAACATAGGTGGTAATTTTAATAGTGG TCCATCAACAGGAGGTAATGGTTC | 56 | 158 | 78.6 |
| lukS-PV Excess Primer | GAGGTGGCCTTTCCAATAC | 57 | 19 | 64.4 |
| lukS-PV Limiting primer | GAACCATTACCTCCTGTTGATGGACCAC | 58 | 28 | 69.2 |
| lukS-PV probe FAM | BHQ1- TGTACCACCTATGTTATAACCTAATGCA - | 59 | 28 | 58.6 |
| VanA Amplicon: 7596-7675 | GAGCAGGCTGTTTCGGGCTGTGAGGTCGGTTGTGCG GTATTGGGAAACAGTGCCGCGTTAGTTGTTGGCGAG GTGGACC | 17 | 79 | 87.0 |
| vanA Excess Primer | GAGCAGGCTGTTTCGG | 18 | 16 | 64.5 |
| vanA Limiting Primer | GGTCCACCTCGCCAACAACTAACG | 19 | 24 | 69.7 |
| vanA probe | Cal Org- TTAATACCGCACAAAA -BHQ1 | 20 | 16 | 45.6 |
| Internal control DNA sequence | GAACATTACCTGCCATCCAAGTGTATCATATCGCAA AACCACAATGGTCTGTTGGCTCCTTGC Arabidopsis thaliana chromosome 1 | 21 | 63 | |
| Excess Primer reverse complement | GAACATTACCTGCCATCCAA | 22 | 20 | 63.4 |
| Limiting Primer | GCAAGGAGCCAACAGACCATTGTG | 23 | 24 | 68.2 |
| Internal ctrl probe | FAM- TATTTGCGATATGATATA -BHQ1 | 24 | 18 | 44.4 |
| External control DNA sequence | GAACATTACCTGCCATCCAAGTTAGTGGGAGCAGAC CACAATGGTCTGTTGGCTCCTTGC Arabidopsis thaliana chromosome 1 | 25 | 60 | |
| Excess Primer reverse complement | GAACATTACCTGCCATCCAA | 26 | 20 | 63.4 |
| Limiting Primer | GCAAGGAGCCAACAGACCATTGTG | 27 | 24 | 68.2 |
| External Ctrl probe | Quasar670- AACTGCTCCCACTTT - BHQ2 | 28 | 15 | 47.5 |
| Additional control DNA sequence | TCATTATTCCTCAAGAAGAGATACAATCGGTCACTT TTAAGAAAGGTTTACTTGCTTATAAAATGGTTGTGA CTACTAAAGATAACGAAGTTCCT | 29 | 95 | 75.9 |
| Excess Primer reverse | TCATTATTCCTCAAGAAGAGATACAATCG | 30 | 29 | 65.8 |
| Limiting Primer | AGGAACTTCGTTATCTTTAGTAGTCACAACCA | 31 | 32 | 67.1 |
| Ctrl probe | FAM (or Quasar)-ATAAACCTTTCTTAAAAT - BHQ1 (or BHQ2) | 32 | 18 | 43.9 |

The SCCmec amplicons, primers and probes are designed to cover the possible SCCmec cassettes that are referenced in the literature. Although the cassettes have different numbering schemes, they are derived from the following references: "Combination of Multiplex PCRs for Staphylococcal Cassette Chromosome mec Type Assignment: Rapid Identification System for mec, ccr, and Major Differences in Junkyard Regions", Yoko Kondo, Teruyo Ito, Xiao Xue Ma, Shinya Watanabe, Barry N. Kreiswirth, Jerome Etienne, and Keiichi Hiramatsu, ANTIMICROBIAL AGENTS AND CHEMOTHERAPY, January 2007, p. 264-274; and "PCR for the identification of methicillin resistant *Staphylococcus aureus* (MRSA) strains using a single primer pair specific for SCCmec elements and the neighboring chromosome-borne orfX", C. Cuny and W. Witte, Clin Microbiol Infect 2005; 11: 834-837; and "New Real-Time PCR Assay for Rapid Detection of Methicillin-Resistant *Staphylococcus aureus* Directly from Specimens Containing a Mixture of Staphylococci", A. Huletsky, R. Giroux, V. Rossbach, M. Gagnon, M. Vaillancourt, M. Bernier, F. Gagnon, K. Truchon, M. Bastien, F. J. Picard, A. van Belkum, M. Ouellette, P. H. Roy, and M. G. Bergeron1, JOURNAL OF CLINICAL MICROBIOLOGY, May 2004, p. 1875-1884; all of which are herein incorporated by reference in their entireties. Table 3 provides the forward/limiting, reverse/excess, target amplicon, and probe sequences used to detect the various SCCmec cassette targets. In Table 3, in the various target sequences, the complement of the excess primer sequence, probe hybridization sequence, and limiting primer sequences are all underlined. The probe in Table 3 (molecular beacon probes) is shown with the hybridization portion of the probe underlined, and the part of the probe that forms the "stem" of the molecular beacon non-underlined.

TABLE 3

| Name | Sequence | SEQ ID NO: | Bases | $T_M$, °C. |
|---|---|---|---|---|
| LimPriIII H3, H7, M3, M5 | TTAGTTTTATTTATGATACGCTTCTCC | 33 | 27 | 60-50 |
| LimPriII H2, H4, H5, M2, M4 | ACCGCATCATTTATGATATGCTTCTCC | 34 | 27 | 66-50 |
| LimPriI H1, M1 | ACCTCATTACTTATGATAAGCTTCTCC | 35 | 27 | 66 |
| Excess Primer | TGACATTCCCACATCAAATGAT | 36 | 22 | 64.4 |
| Bridge Probe | FAM- TTTCTTAAATGCTCTATACACTTGAA-BHQ1 | 37 | 26 | 56.8/50.0 |
| SCCmec I | ACCTCATTACTTATGATAAGCTTCTCCTCGCATAATCTTAAATGCTCTGTACACTTGTTCAATTAACACAACCCGCATCATTTGATGTGGGAATGTCA | 38 | 98 | 80.0 |
| SCCmec II | ACCGCATCATTTATGATATGCTTCTCCACGCATAATCTTAAATGCTCTATACACTTGCTCAATTAACACAACCCGCATCATTTGATGTGGGAATGTCA | 39 | 98 | 80.0 |
| SCCmec III | TTAGTTTTATTTATGATACGCTTCTCCACGCATAATCTTAAATGCTCTGTACACTTGTTCAATTAACACAACCCGCATCATTTGATGTGGGAATGTCA | 40 | 98 | 80.0 |
| SCCmec IV | ACCGCATCATTTGTGGTACGCTTCTCCACGCATAATCTTAAATGCTCTGTACACTTGTTCAATTAACACAACCCGCATCATTTGATGTGGGAATGTCA | 41 | 98 | 80.0 |
| SCCmec V | ACCGCATCATTTATGATATGCTTCTCCTCGCATAATCTTAAATGCTCTGTACACTTGTTCAATTAACACAACCCGCATCATTTGATGTGGGAATGTCA | 42 | 98 | 80.0 |
| SCCmec VII | TTAGTTTTATTTGTGGTACGCTTCTCCACGCATAATCTTAAATGCTCTATACACTTGTTCAATTAACACAACCCGCATCATTTGATGTGGGAATGTCA | 43 | 98 | 80.0 |

When the limiting primers get incorporated in the LATE-PCR reaction there is a mixture of all three products for each SCCmec cassette, but based on the primer $T_M$, one will be dominant. The targets generated for each SCCmec are shown below in Table 4 and the dominant target is shown in bold type.

TABLE 4

New Targets Generated by Limiting Primers

SCCmec I: Lim 1
ACCTCATTACTTATGATAAGCTTCTCCTCGCATAA<u>T</u>CTTAAATGCTCTGTACACTTGTTCAATTAACAC
AACCCGC<u>ATCATTTGATGTGGGAATGTCA</u> (SEQ ID NO: 38)

SCCmec I: Lim 2
ACCGCATCATTTATGATATGCTTCTCCTCGCATAA<u>T</u>CTTAAATGCTCTGTACACTTGTTCAATTAACAC
AACCCGC<u>ATCATTTGATGTGGGAATGTCA</u> (SEQ ID NO: 44)

SCCmec I: Lim 3
<u>TTAGTTTTATTTATGATACGCTTCTCCTCGCATAA</u>TCTTAAATGCTCTGTACACTTGTTCAATTAACAC
AACCCGC<u>ATCATTTGATGTGGGAATGTCA</u> (SEQ ID NO: 45)

SCCmec II: Lim 1
<u>ACCTCATTACTTATGATAAGCTTCTCCACGCATAA</u>TCTTAAATGCTCTATACACTTGCTCAATTAACAC
AACCCGC<u>ATCATTTGATGTGGGAATGTCA</u> (SEQ ID NO: 46)

SCCmec II: Lim 2
ACCGCATCATTTATGATATGCTTCTCCACGCATAA<u>T</u>CTTAAATGCTCTATACACTTGCTCAATTAACAC
AACCCGC<u>ATCATTTGATGTGGGAATGTCA</u> (SEQ ID NO: 39)

SCCmec II: Lim 3
<u>TTAGTTTTATTTATGATACGCTTCTCCACGCATAA</u>TCTTAAATGCTCTATACACTTGCTCAATTAACAC
AACCCGC<u>ATCATTTGATGTGGGAATGTCA</u> (SEQ ID NO: 47)

SCCmec III: Lim 1
ACCTCATTACTTATGATAAGCTTCTCCACGCATAA<u>T</u>CTTAAATGCTCTGTACACTTGTTCAATTAACAC
AACCCGC<u>ATCATTTGATGTGGGAATGTCA</u> (SEQ ID NO: 48)

SCCmec III: Lim 2
ACCGCATCATTTATGATATGCTTCTCCACGCATAA<u>T</u>CTTAAATGCTCTGTACACTTGTTCAATTAACAC
AACCCGC<u>ATCATTTGATGTGGGAATGTCA</u> (SEQ ID NO: 49)

SCCmec III: Lim 3
TTAGTTTTATTTATGATACGCTTCTCCACGCATAA<u>T</u>CTTAAATGCTCTGTACACTTGTTCAATTAACAC
AACCCGC<u>ATCATTTGATGTGGGAATGTCA</u> (SEQ ID NO: 40)

SCCmec IV: Lim 1
<u>ACCTCATTACTTATGATAAGCTTCTCCACGCATAA</u>TCTTAAATGCTCTGTACACTTGTTCAATTAACAC
AACCCGC<u>ATCATTTGATGTGGGAATGTCA</u> (SEQ ID NO: 50)

SCCmec IV: Lim 2
ACCGCATCATTTATGATATGCTTCTCCACGCATAA<u>T</u>CTTAAATGCTCTGTACACTTGTTCAATTAACAC
AACCCGC<u>ATCATTTGATGTGGGAATGTCA</u> (SEQ ID NO: 41)

SCCmec IV: Lim3
<u>TTAGTTTTATTTATGATACGCTTCTCCACGCATAA</u>TCTTAAATGCTCTGTACACTTGTTCAATTAACAC
AACCCGC<u>ATCATTTGATGTGGGAATGTCA</u> (SEQ ID NO: 51)

SCCmec V: Lim 1
ACCTCATTACTTATGATAAGCTTCTCCTCGCATAA<u>T</u>CTTAAATGCTCTGTACACTTGTTCAATTAACAC
AACCCGC<u>ATCATTTGATGTGGGAATGTCA</u> (SEQ ID NO: 52)

SCCmec V: Lim 2
ACCGCATCATTTATGATATGCTTCTCCTCGCATAA<u>T</u>CTTAAATGCTCTGTACACTTGTTCAATTAACAC
AACCCGC<u>ATCATTTGATGTGGGAATGTCA</u> (SEQ ID NO: 42)

SCCmec V: Lim 3
<u>TTAGTTTTATTTATGATACGCTTCTCCTCGCATAA</u>TCTTAAATGCTCTGTACACTTGTTCAATTAACAC
AACCCGC<u>ATCATTTGATGTGGGAATGTCA</u> (SEQ ID NO: 53)

SCCmec VII: Lim 1
ACCTCATTACTTATGATAAGCTTCTCCACGCATAA<u>T</u>CTTAAATGCTCTATACACTTGTTCAATTAACAC
AACCCGC<u>ATCATTTGATGTGGGAATGTCA</u> (SEQ ID NO: 54)

SCCmec VII: Lim 2
ACCGCATCATTTATGATATGCTTCTCCACGCATAA<u>T</u>CTTAAATGCTCTATACACTTGTTCAATTAACAC
AACCCGC<u>ATCATTTGATGTGGGAATGTCA</u> (SEQ ID NO: 55)

SCCmec VII: Lim 3
TTAGTTTTATTTATGATACGCTTCTCCACGCATAA<u>T</u>CTTAAATGCTCTATACACTTGTTCAATTAACAC
AACCCGC<u>ATCATTTGATGTGGGAATGTCA</u> (SEQ ID NO: 43)

Other reagents used in the assays below are as shown in Table 5.

TABLE 5

| | |
|---|---|
| Taq Polymerase | 1.25 U/25 uL |
| Tfi- Polymerase | 0.4 uL/25 uL |
| Primesafe #1 | 100 nM for Tfi- |
| Primesafe #2 | 300 nM for Pt Taq |
| Easyplex LDL22 | 300 nM for Tfi- |
| Easyplex 4D22 | 600 nM for Tfi- |
| Magnesium | 3 mM |
| Tfi- Buffer | 1X |
| Taq Buffer | 1X |
| dNTPS | 250 uM |
| RNA Free Water | |
| Limiting Primer | 50 nM |
| Excess Primer | 1 uM |
| Probe | 100 nM |
| DNA Copy Number | ~3000/25 uL |

Exemplary Monoplex Assay

To describe how the 1-plex assays are performed, the protocol for the femA assay is described below, beginning with source of materials in Table 6.

TABLE 6

| Materials | |
|---|---|
| Nuclease free water | Ambion |
| PCR buffer | Invitrogen |
| MgCl2 (Tfi kit) | Invitrogen |
| Lim primer (FemA_SA) | Biosearch |
| Ex primer (FemA-SA) | Biosearch |
| Probe (FemA-SA) | Biosearch |

TABLE 6-continued

| Materials | |
|---|---|
| dNTPs | Roche |
| Pt Tfi (—) (taq) | Invitrogen |
| FemA-SA amplicon | Eurogentec |

Samples: FemA_SA amplicon ($1 \times 10^6$) (Eurogentec)
10-fold dilution series of this to give $1 \times 10^6$ with nuclease free water.

Methods
1. Label 2 eppendorf tubes 'NTC mix' and 'FemA-SA mix'
2. Pipette the volumes of reagents listed in the table 7 (below) labeled 'mix' into both tubes.
3. Add the stated volume of nuclease free water to both tubes.
4. Vortex and spin the tubes, and in the meantime prepare the EZplex and TFi mix.
5. Add the given volume of EZplex and TFI mix to the NTC and FEMA-SA tubes.
6. Vortex and spin.
7. Aliquot 25 μl of the NTC mix into 3 smartcycler tubes, labelled NTC and sealed.
8. Transfer the NTC smartcycler tubes and the femA-SA mix into lab3.
9. Spin down the smartcycler tubes and insert into smart cycler machine.
10. Add given volume of Amplicon/to FemA-SA mix, centrifuge and aliquot 25 μl into 3 smartcyler tubes labelled femA-SA.
11. Spin down these tubes and insert into the SmartCyler block.

TABLE 7

Components of MRSA 1-plex assay (femA).

| water | working stock | [final] | μl/25 μl | 1x | 5x | 10x |
|---|---|---|---|---|---|---|
| Nuclease free water | n/a | n/a | 13 | 13 | 65 | 130 |
| Total | | | 13 | 13 | 65 | 130 |
| Mix | | | | | | |
| PCR buffer | 5X | 1 | 5 | 5 | 25 | 50 |
| MgCl2 (Tfi kit) | 50 mM | 3 nM | 1.5 | 1.5 | 7.5 | 15 |
| Lim primer (FemA_SA) | 10 μM | 50 nM | 0.125 | 0.125 | 0.625 | 1.25 |
| Ex primer (FemA-SA) | 100 μM | 1000 nM | 0.25 | 0.25 | 1.25 | 2.5 |
| Probe (FemA-SA) | 10 μM | 100 nM | 0.25 | 0.25 | 1.25 | 2.5 |
| dNTPs | 10 mM | 250 μM | 0.625 | 0.625 | 3.125 | 6.25 |
| Total | | | 7.75 | 7.75 | 38.75 | 77.5 |
| mix 4d22 and tfi together first then add to mix | | | | | | |
| TFi | | | | | | |
| Pt Tfi (—) (taq) | 5 U/μl | 2 U/25 μl | 0.25 | 0.25 | 1.25 | 2.5 |
| 4d22 ezplex | | | 0 | 0 | 0 | 0 |
| Total | | | 0.25 | 0.25 | 1.25 | 2.5 |
| DNA | | | 4 | 4 | 20 | 40 |
| Total | | | 4 | 4 | 20 | 40 |
| subtotal | | | 25 | 25 | 125 | 250 |

| | NTC | MSSA |
|---|---|---|
| water | 85 | 65 |
| mix | 38.75 | 38.75 |
| tfi- | 1.25 | 1.25 |
| dna | 0 | 20 |
| | 125 | 125 |

12. Thermocycle using the following profile:
a) 95° C., 3 min
b) 50 cycles of:
  i. 95° C., 10 s
  ii. 58° C., 15 s
  iii. 68° C., 30 s
c) End-point detection:
  i. 70° C., read for 30 s
  ii. 50° C., read for 30 s
  iii. 35° C., read for 30 s
d) Anneal curve detection (using instrument software, otherwise 30 s read at each degree)
  i. 95° C. to 30° C.
e) Melt curve detection (using instrument software, otherwise 30 s read at each degree)
  i. 30° C. to 95° C.

Analysis of Resulting Data can be Conducted as Follows for the Exemplary femA Monoplex and Other Monoplex Targets:

a) End-Point Detection.

Figure 2A:
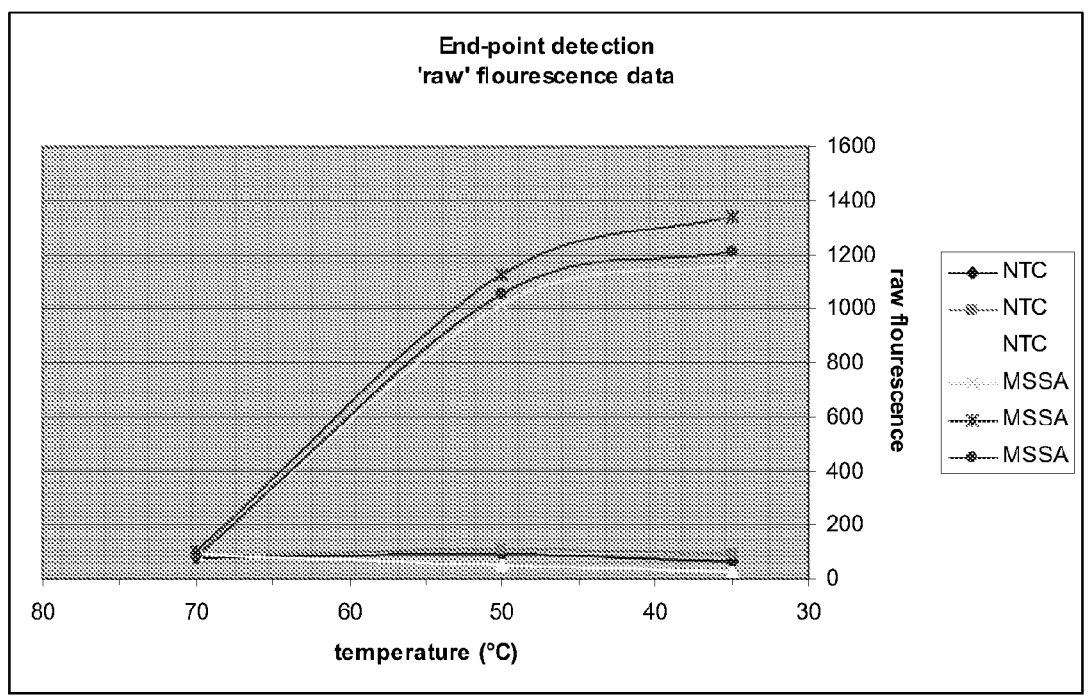
FIG. 2 shows end point detection results from the exemplary monoplex detection of FemA-SA described in Example 1. Exemplary raw fluorescence data is shown in FIG. 2A. Normalized data to 70° C. F/F70 is shown in FIG. 2B. Calculated end-point double ratio [F35/F70]/F50/F70] is shown in FIG. 2C.

End-point detection method/algorithm can be employed on automated instruments. Exemplary raw fluorescence data is shown in FIG. 2A. Normalized data to 70 C F/F70 is shown in FIG. 2B. Calculated end-point double ratio [F35/F70]/[F50/F70] is shown in FIG. 2C.

b) Anneal Curve Detection.

Figure 3A:
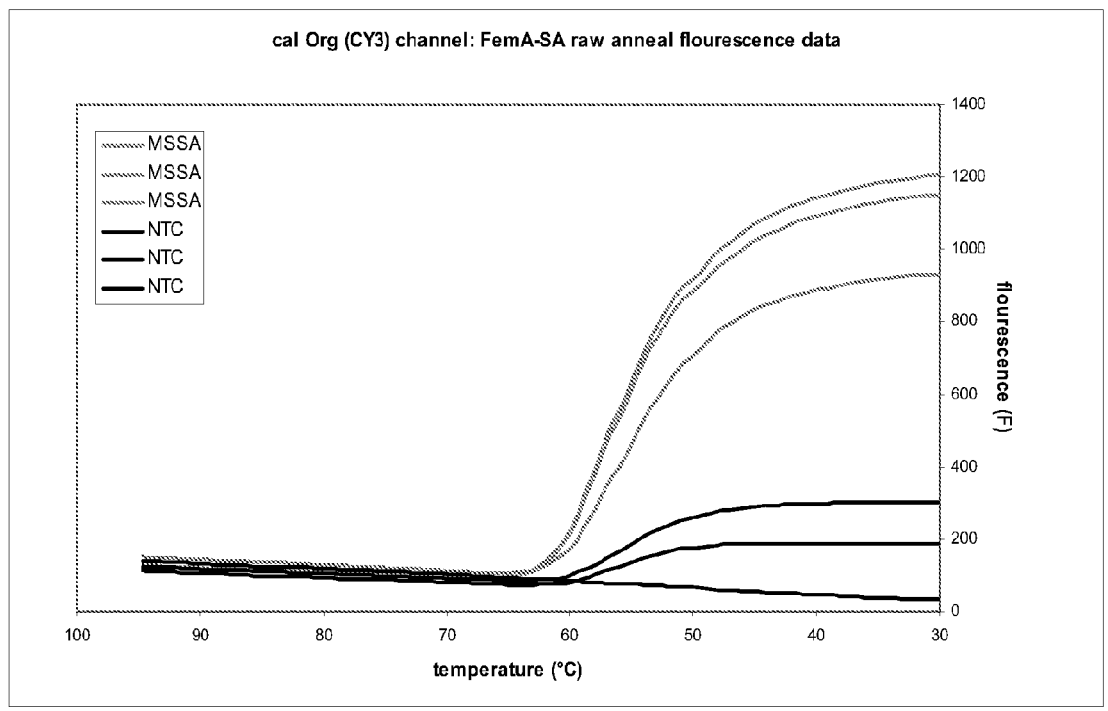
FIG. 3 shows anneal curve detection results from the exemplary monoplex detection of FemA-SA described in Example 1. The anneal raw fluorescence data is shown in FIG. 3A, the normalized anneal fluorescence data to F70° C. is shown in FIG. 3B, and the calculated anneal ratio (double ratio): [F35/F70]/F47/F70], is shown in FIG. 3C.

This method is performed to help optimize the end-point detection method/algorithm. The anneal curve method also allows detection of products (potentially non-specific) which may be formed during PCR. The anneal raw fluorescence data is shown in FIG. 3A, the normalized anneal fluorescence data to F70° C. is shown in FIG. 3B, and the calculated anneal ratio (double ratio): [F35/F70]/[F47/F70], is shown in FIG. 3C.

c) Melt Curve Detection

Figure 4:
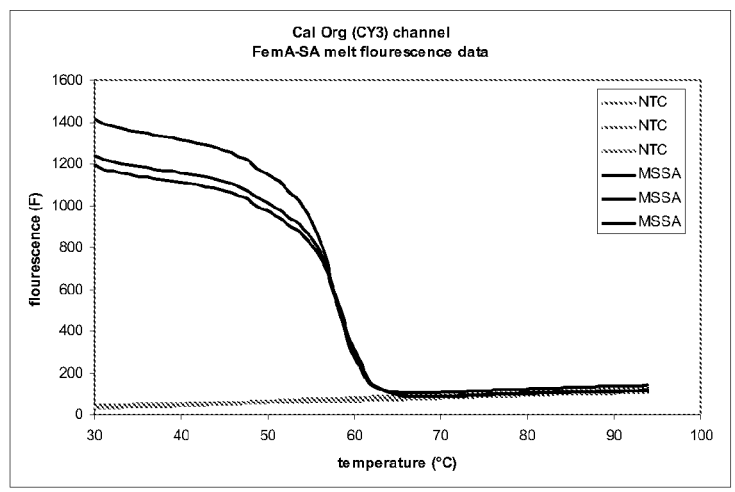
FIG. 4 shows melt curve detection results from the exemplary monoplex detection of FemA-SA described in Example 1. The anneal raw fluorescence data is shown in FIG. 4A, the normalized anneal fluorescence data to F70° C. is shown in FIG. 4B, and the calculated anneal ratio (double ratio): [F35/F70]/F47/F70], is shown in FIG. 4C.
Figure 4:
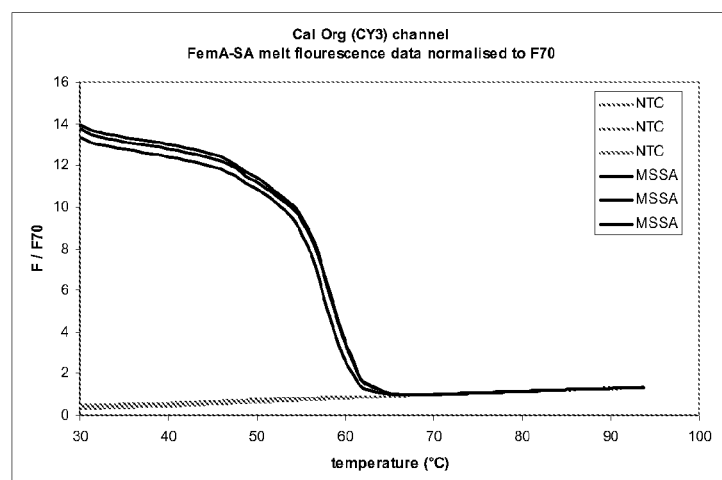
Figure 4:
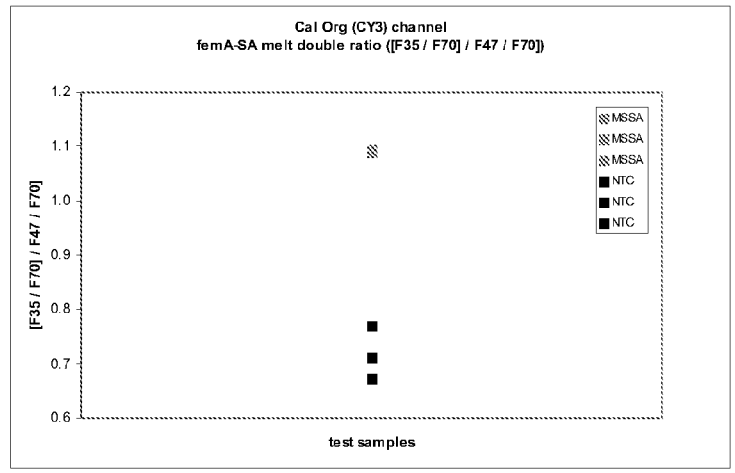

Similar to the anneal curve method, melt curve detection is performed to help optimize the end-point detection method/algorithm. The melt curve method also allows detection of products (potentially non-specific) which may be formed during PCR. The melt raw fluorescence data is shown in FIG. 4A, the normalized melt melt fluorescence data to 70° C. is shown in FIG. 4B, and the calculated melt ratio (double ratio): [F35/F70]/F47/F70], is shown in FIG. 4C.

Exemplary Multiplex Detection

To describe how to perform a MRSA multiplex assay, as an example, the protocol to perform the femA_SA, femA-SE, and mecA is described below beginning with a description of the materials in Table 8.

TABLE 8

| Materials | |
|---|---|
| Nuclease free water | Ambion |
| PCR buffer | Invitrogen |
| MgCl2 (Tfi kit) | Invitrogen |
| Lim primer (FemA_SA) | Biosearch |
| Ex primer (FemA-SA) | Biosearch |
| Probe (FemA-SA) | Biosearch |
| Lim primer (FemA_SE) | Biosearch |
| Ex primer (FemA-SE) | Biosearch |
| Probe (FemA-SE) | Biosearch |
| Lim primer (mecA) | Biosearch |

TABLE 8-continued

| Materials | |
|---|---|
| Ex primer (mecA) | Biosearch |
| Probe (mecA) | Biosearch |
| dNTPs | Roche |
| Pt Tfi (—) (taq | Invitrogen |

Samples

FemA_SA amplicon ($1\times10^{12}$) dilute to give $1\times10^6$ with NFW.

FemA_SE amplicon ($1\times10^{12}$) dilute to give $1\times10^6$ with NFW.

MecA amplicon ($1\times10^{12}$) dilute to give $1\times10^6$ with NFW.

Methods

1. Label 4 eppendorf tubes 'NTC mix' and 'assay mix'

2. Pipette the volumes of reagents listed in Table 9 (below) labeled 'mix' into both tubes 3. Add the stated volume of nuclease free water to both tubes.

4. Vortex and spin the tubes, and in the meantime prepare the EZplex and TFi mix, 5. Add the given volume of EZplex and TFI mix to the NTC and assay tubes.

6. Vortex and spin

7. Aliquot 25 µl of the NTC mix into 3 smartcycler tubes, labeled NTC and seal.

8. Transfer the NTC smartcycler tubes and the 'assay mix' into lab 3

9. Spin down the smartcycler tubes and insert into smart cycler machine,

10. Add given volume of Amplicon/to 'assay mix', centrifuge and aliquot 25 µl into 3 smartcyler tubes labeled appropriately.

11. Spin down these tubes and insert into the smartcycler block.

12. Thermocycle using the following profile:
a) 95° C., 3 min
b) 50 cycles of:
  i. 95° C., 10 s
  ii. 58° C., 15 s
  iii. 68° C., 30 s
c) End-point detection:
  i. 70° C., read for 30 s
  ii. 50° C., read for 30 s
  iii. 35° C., read for 30 s
d) Anneal curve detection (using instrument software, otherwise 30 s read at each degree)
  i. 95° C. to 30° C.
e) Melt curve detection (using instrument software, otherwise 30 s read at each degree)
  i. 30° C. to 95° C.

TABLE 9

Components of MRSA multiplex assay (femA_SA, femA-SE, and mecA).

| mix | working stock | | [final] | | μl/25 μl | 1x | 5x | 10x |
|---|---|---|---|---|---|---|---|---|
| Nuclease free water | n/a | | n/a | | 2.25 | 2.25 | 11.25 | 22.50 |
| Total | | | | | 2.25 | 2.25 | 11.25 | 22.50 |
| PCR buffer | 5X | | 1 | | 5.00 | 5.00 | 25.00 | 50.00 |
| MgCl2 (Tfi kit) | 50 | mM | 3 | mM | 1.50 | 1.50 | 7.50 | 15.00 |
| Lim primer FemA-SA | 10 | μM | 50 | mM | 0.13 | 0.13 | 0.63 | 1.25 |
| Lim primer FemA-SE | 10 | μM | 50 | mM | 0.13 | 0.13 | 0.63 | 1.25 |
| Lim primer MecA | 10 | μM | 50 | mM | 0.13 | 0.13 | 0.63 | 1.25 |
| Ex primer FemA-SA | 100 | μM | 1 | μM | 0.25 | 0.25 | 1.25 | 2.50 |
| Ex primer FemA-SE | 100 | μM | 1 | μM | 0.25 | 0.25 | 1.25 | 2.50 |
| Exc primer MecA | 100 | μM | 1 | μM | 0.25 | 0.25 | 1.25 | 2.50 |
| probe FemA-SA | 10 | μM | 100 | mM | 0.25 | 0.25 | 1.25 | 2.50 |
| probe FemA-SE | 10 | μM | 100 | mM | 0.25 | 0.25 | 1.25 | 2.50 |
| probe MecA | 10 | μM | 100 | mM | 0.25 | 0.25 | 1.25 | 2.50 |
| dNTPs | 10 | mM | 250 | μM | 0.63 | 0.63 | 3.13 | 6.25 |
| Total | | | | | 9 | 9 | 45 | 90 |
| mix 4d22 and tfi together first then add to mix | | | | | | | | |
| Pt Tfi (—) (taq) | 5 | U/μl | 2 U/25 μl | | 0.25 | 0.25 | 1.25 | 2.50 |
| 4D22 | 10 | μM | 600 | nM | 1.50 | 1.50 | 7.50 | 15.00 |
| Total | | | | | 1.75 | 1.75 | 8.75 | 17.50 |
| DNA FemA-SA | | | | | 4.00 | 4.00 | 20.00 | 40.00 |
| DNA FemA-SE | | | | | 4.00 | 4.00 | 20.00 | 40.00 |
| DNA MecA | | | | | 4.00 | 4.00 | 20.00 | 40.00 |
| Total | | | | | 12.00 | 12.00 | 60.00 | 120.00 |
| subtotal | | | | | 25.00 | 25.0 | 125.0 | 250.0 |

| | NTC (x5) | Mplex (x10) |
|---|---|---|
| water | 71.25 | 22.50 |
| mix | 45 | 90 |
| tfi-ezplex | 8.75 | 17.50 |
| femA-SE dna | 0 | 40 |
| femA_SA dna | 0 | 40 |
| DNA MecA | 0 | 40 |
| | 125 | 250 |

Analysis of Resulting Data can be Conducted as Follows for the Exemplary Multi-Plex Assay and Other Multi-Plex Assays:

a) End-Point Detection.

Figure 5:
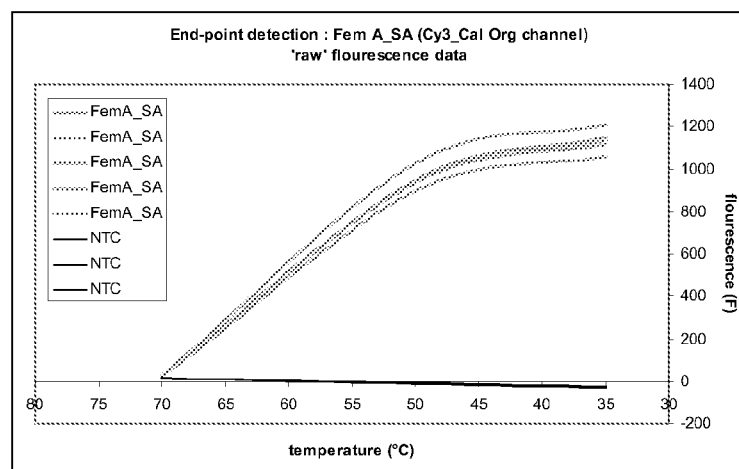
FIGS. 5A-C show (femA-SA, FemA-SE, and MecA respectively) raw fluorescent end point detection results from the exemplary multi-plex detection of FemA-SA, FemA-SE, and mecA described in Example 1.
Figure 5:
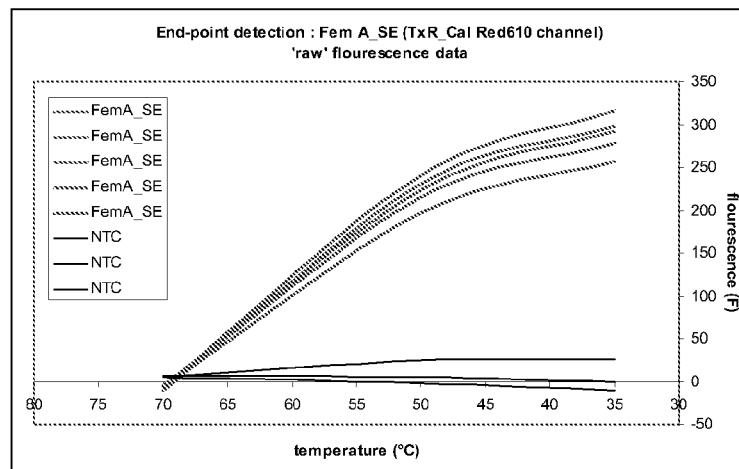
Figure 5:
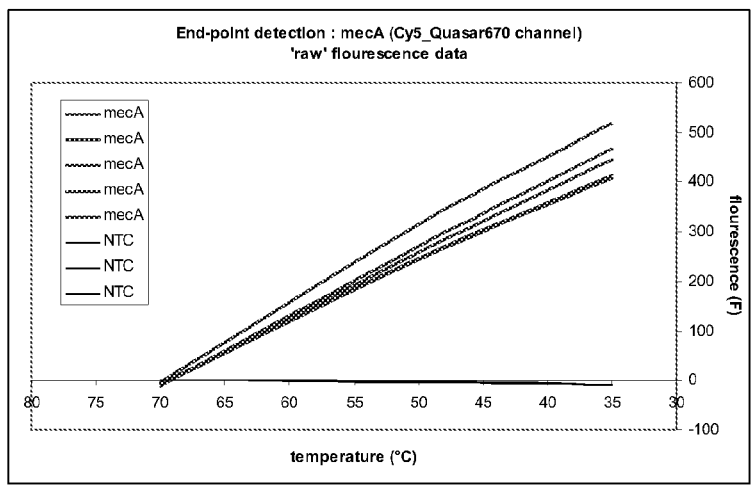
Figure 6:
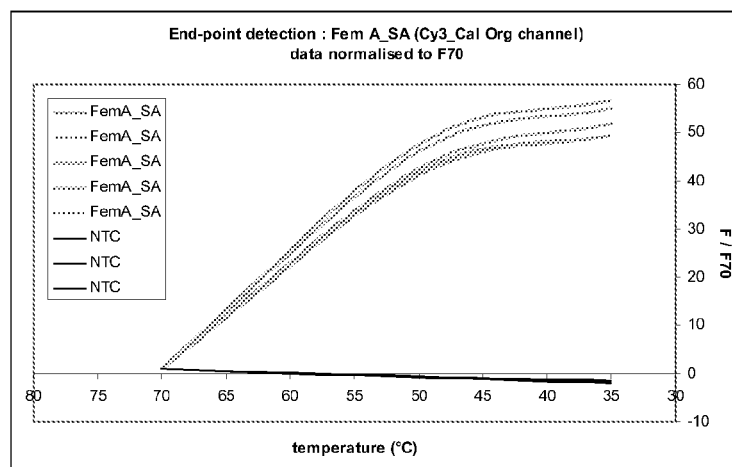
FIGS. 6A-C (femA-SA, FemA-SE, and MecA respectively) show normalized end point detection results from the exemplary multi-plex detection of FemA-SA, FemA-SE, and mecA described in Example 1.
Figure 6:
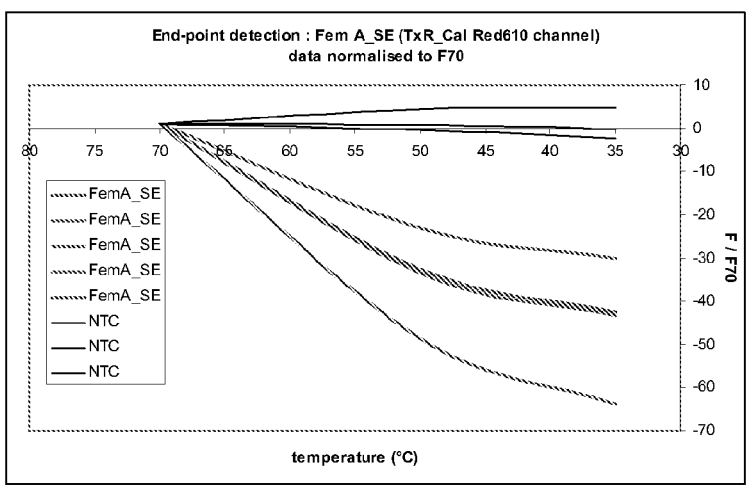
Figure 6:
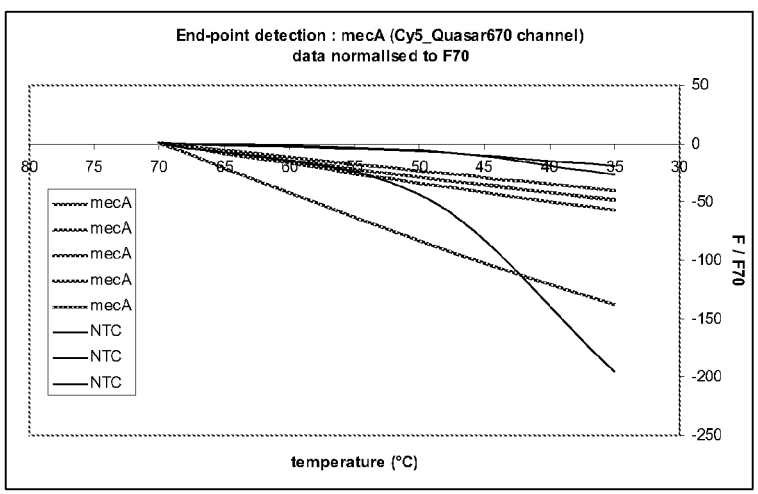
Figure 7:
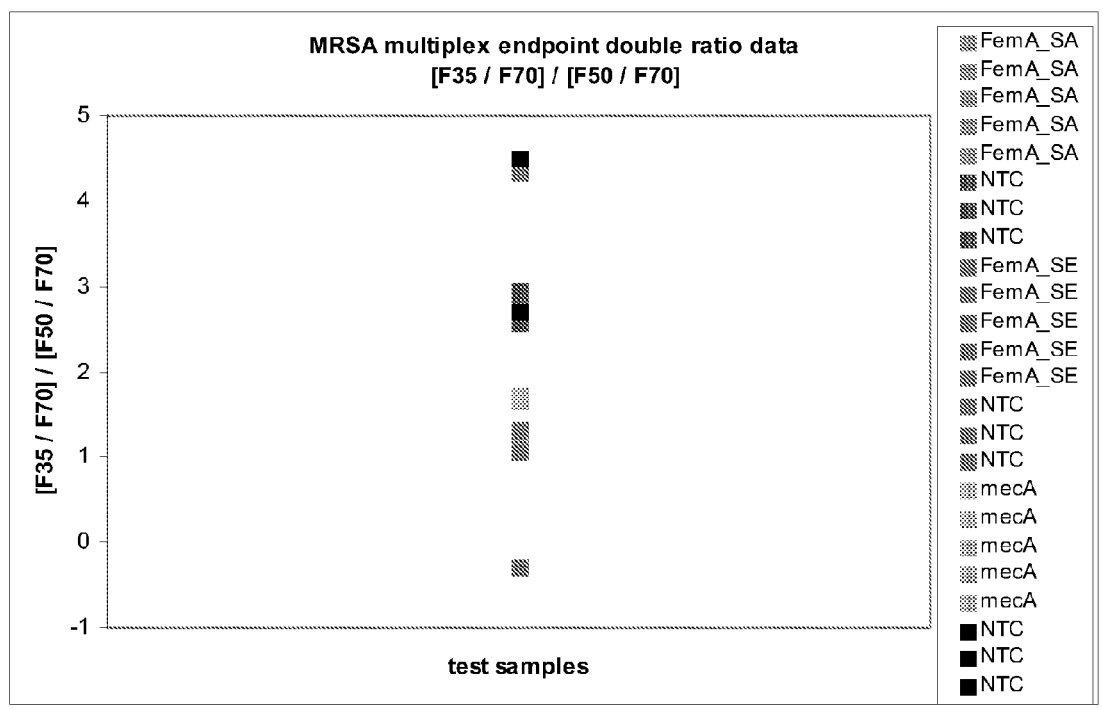
FIG. 7 shows calculated end-point double ratios [F35/F70]/F50/F70] results from the exemplary multi-plex detection of FemA-SA, FemA-SE, and mecA described in Example 1.

End-point detection method/algorithm can be employed on automated instruments. Exemplary raw fluorescence data is shown in FIG. 5A-C. Normalized data to 70 C F/F70 is shown in FIG. 6A-C. Calculated end-point double ratios [F35/F70]/F50/F70] are shown in FIG. 7.

b) Anneal Curve Detection.

Figure 8:
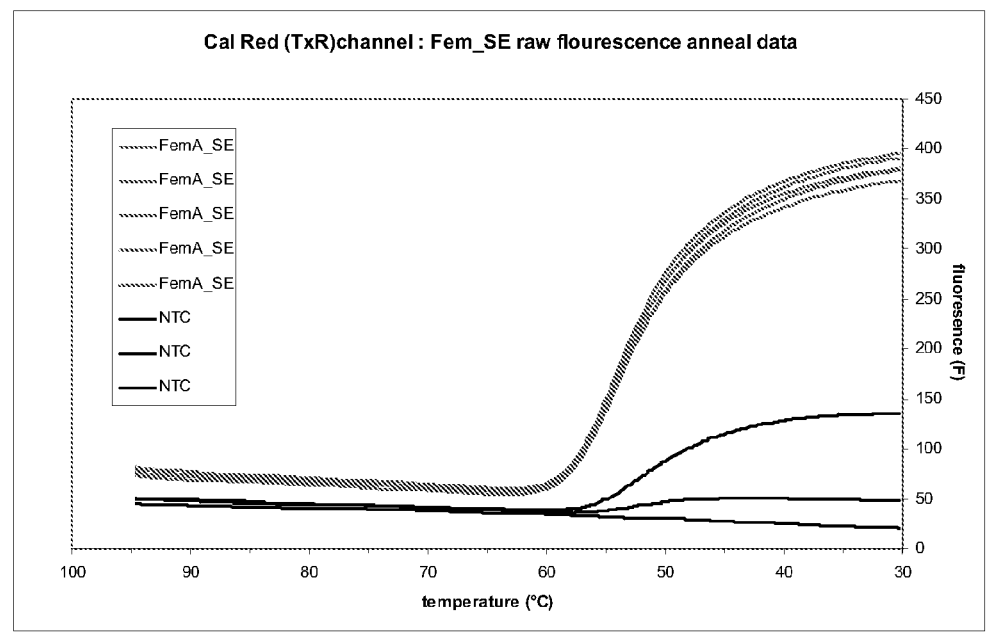
FIGS. 8A-B (FemA-SE and MecA respectively) show raw fluorescent anneal curve detection results from the exemplary multi-plex detection of FemA-SA, FemA-SE, and mecA described in Example 1.
Figure 8:
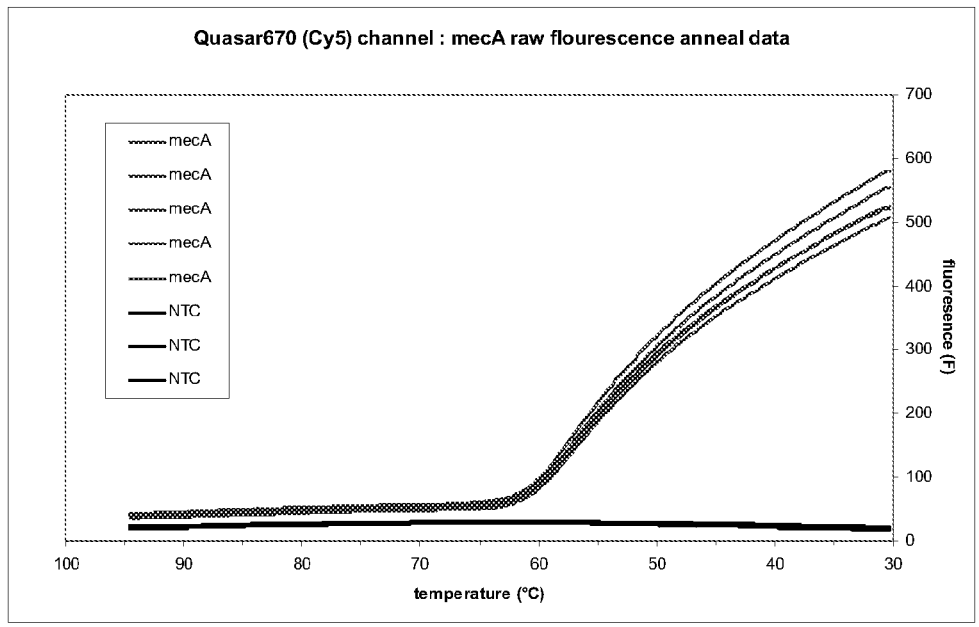
Figure 9:
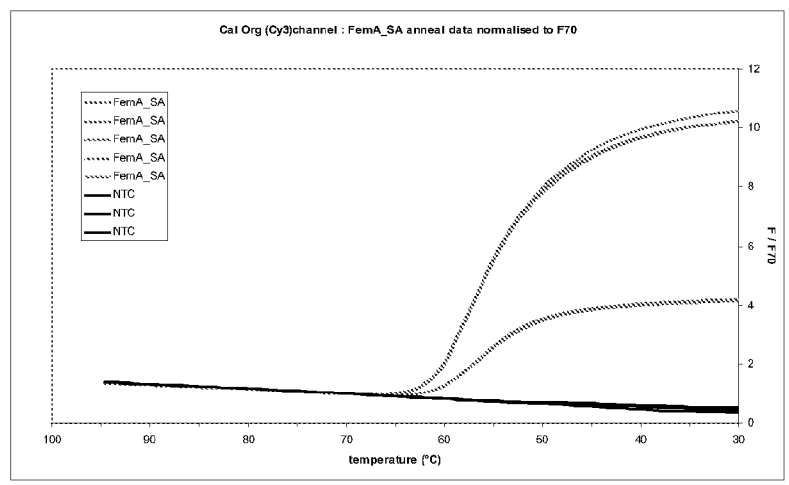
FIGS. 9A-C (femA-SA, FemA-SE, and MecA respectively) show normalized anneal curve detection results from the exemplary multi-plex detection of FemA-SA, FemA-SE, and mecA described in Example 1.
Figure 9:
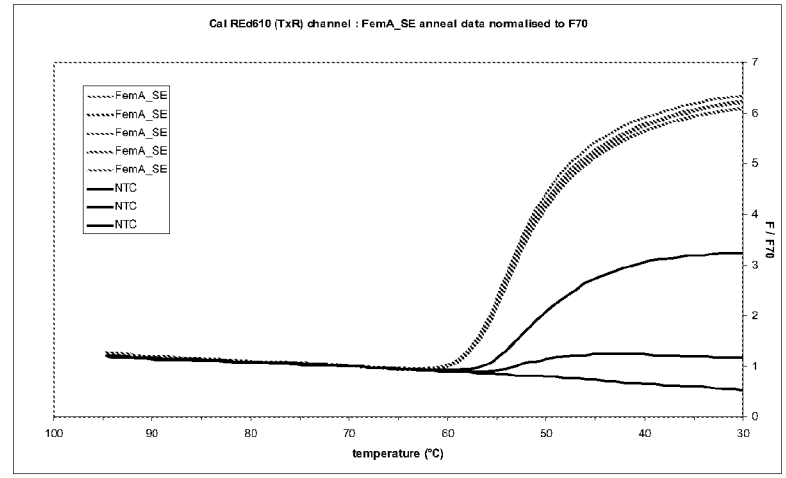
Figure 9:
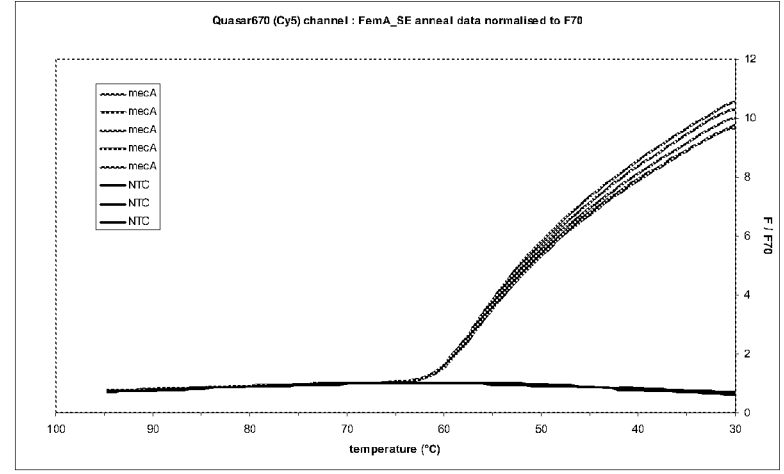
Figure 10:
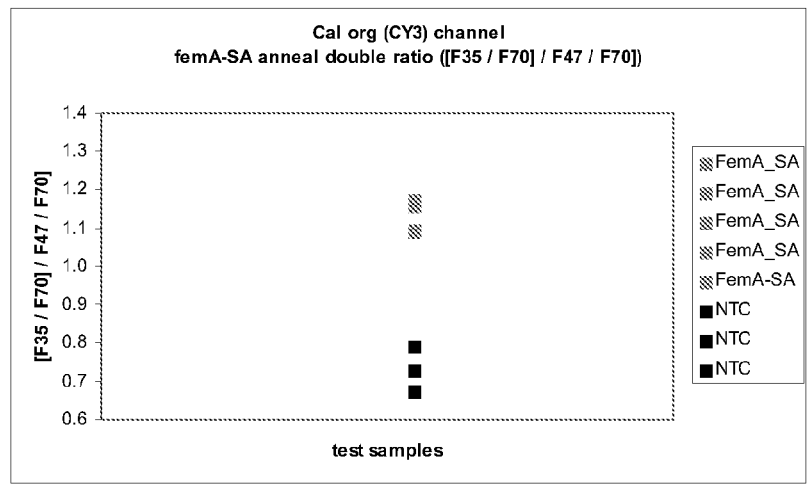
FIGS. 10A-C (femA-SA, FemA-SE, and MecA respectively) shows calculated end-point double ratios [F35/F70]/F50/F70] results from the exemplary multi-plex detection of FemA-SA, FemA-SE, and mecA described in Example 1.
Figure 10:
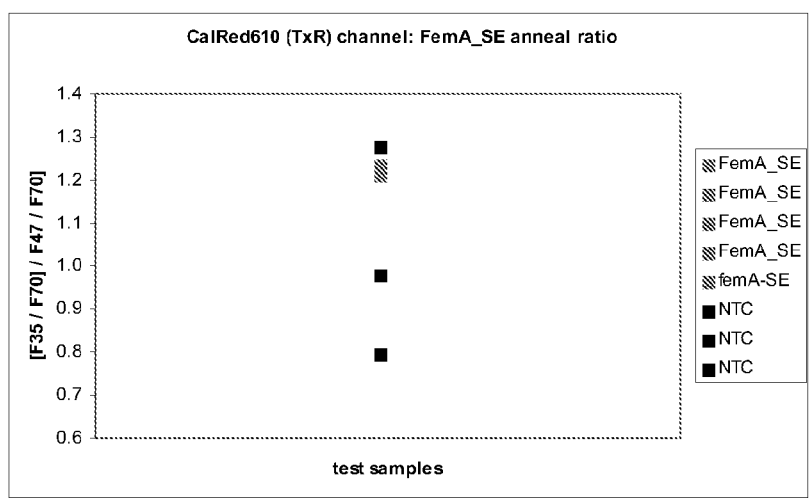
Figure 10:
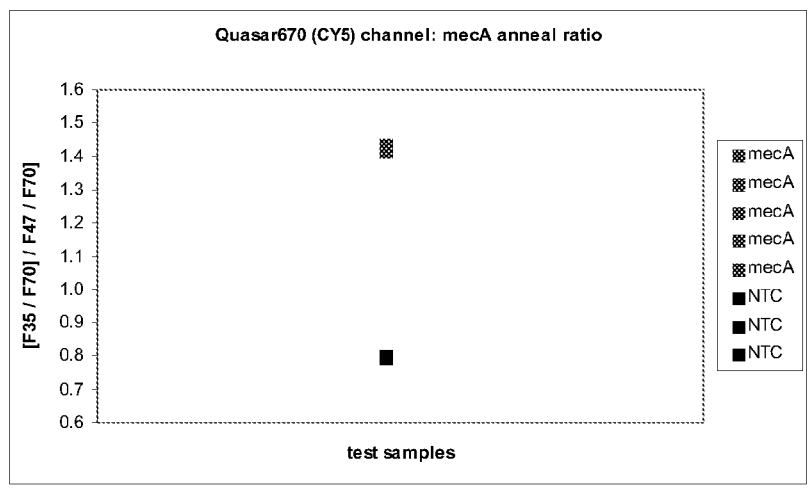

This method is performed to help optimize the end-point detection method/algorithm. The anneal curve method also allows detection of products (potentially non-specific) which may be formed during PCR. The anneal raw fluorescence data is shown in FIG. 8A-B, the normalized anneal fluorescence data to F70° C. is shown in FIG. 9A-C, and the calculated anneal ratios (double ratios): [F35/F70]/F47/F70], are shown in FIG. 10A-C.

c) Melt Curve Detection

Figure 11:
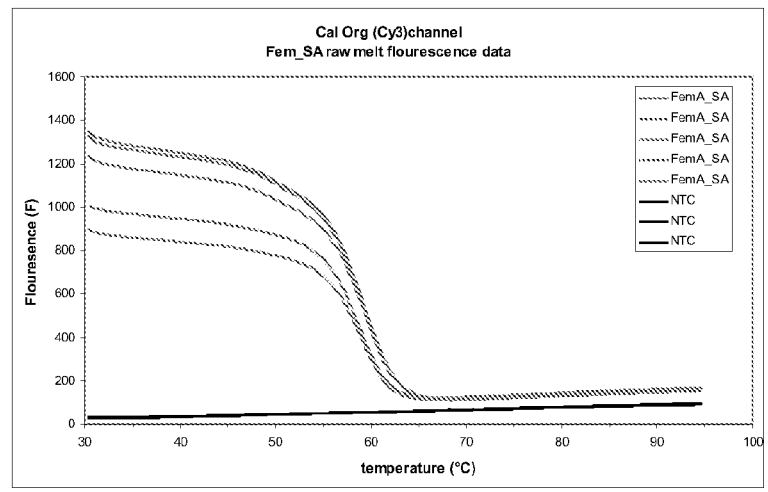
FIGS. 11A-C (femA-SA, FemA-SE and MecA respectively) show raw fluorescent melt curve detection results from the exemplary multi-plex detection of FemA-SA, FemA-SE, and mecA described in Example 1.
Figure 11:
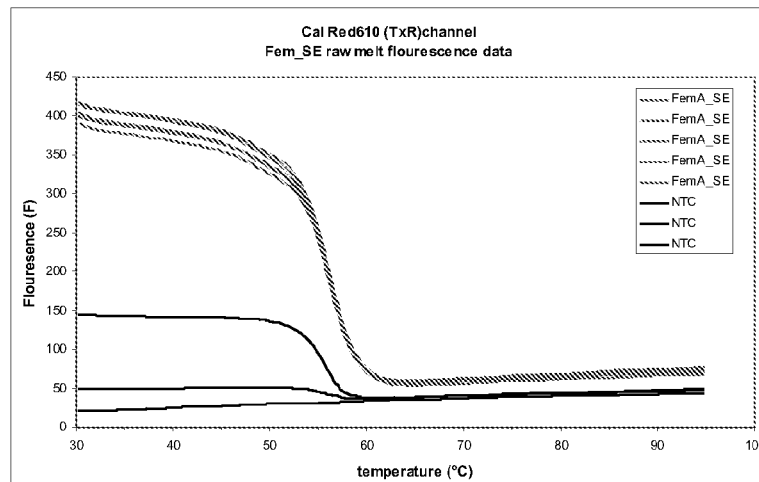
Figure 11:
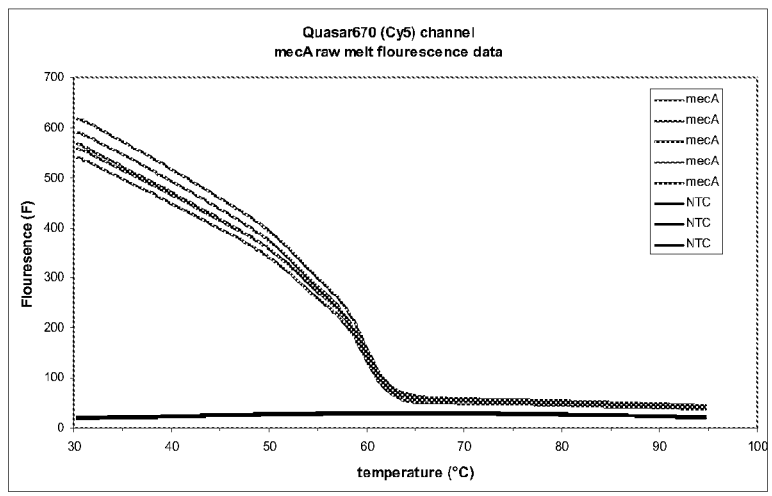
Figure 12:
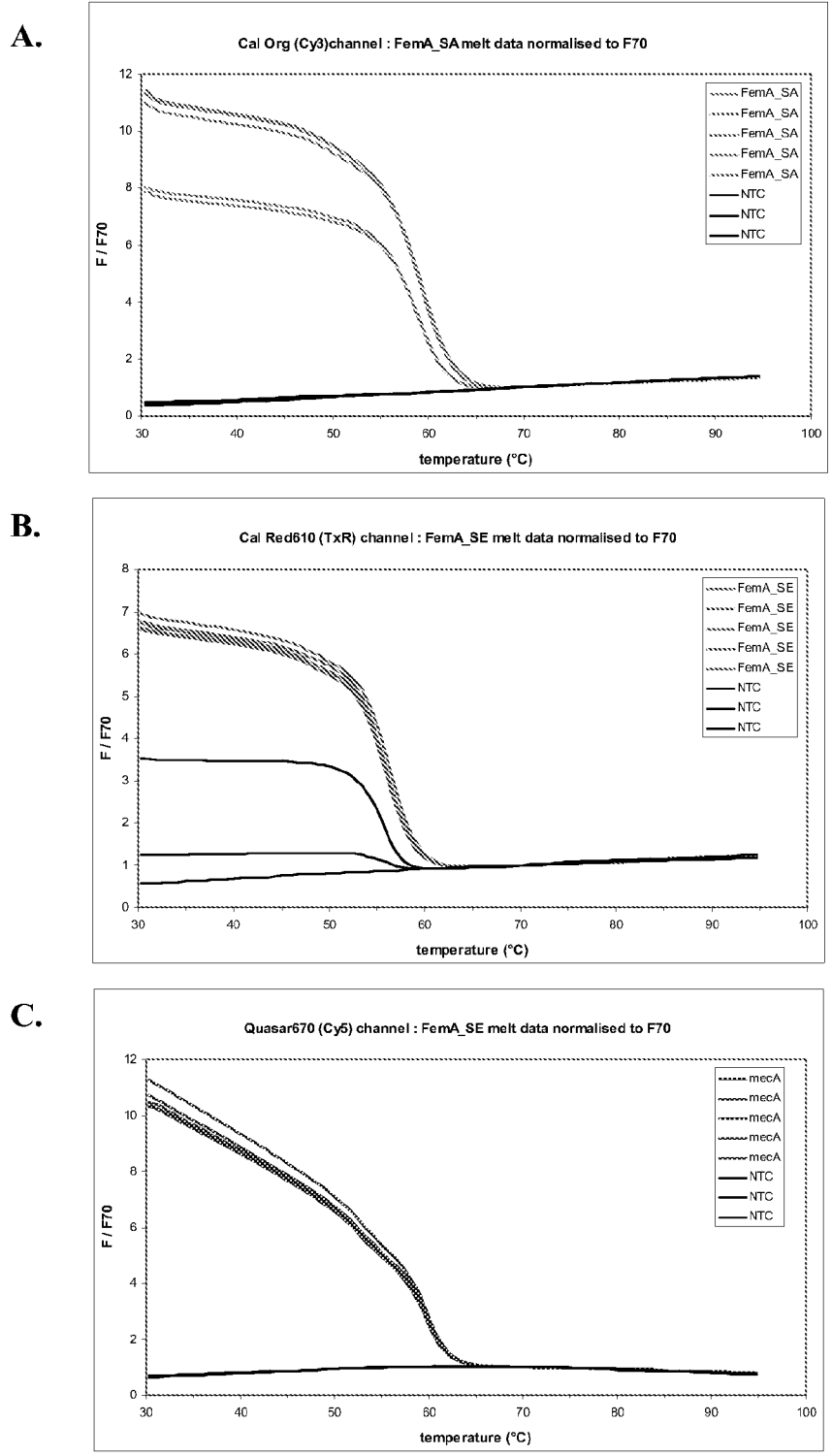
FIGS. 12A-C (femA-SA, FemA-SE, and MecA respectively) show normalized melt curve detection results from the exemplary multi-plex detection of FemA-SA, FemA-SE, and mecA described in Example 1.
Figure 13:
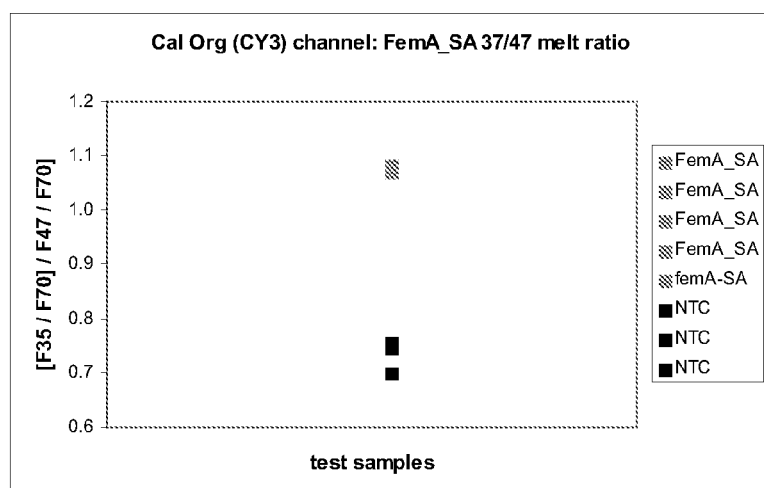
FIGS. 13A-C (femA-SA, FemA-SE, and MecA respectively) shows calculated end-point double ratios [F35/F70]/F50/F70] results from the exemplary multi-plex detection of FemA-SA, FemA-SE, and mecA described in Example 1.
Figure 13:
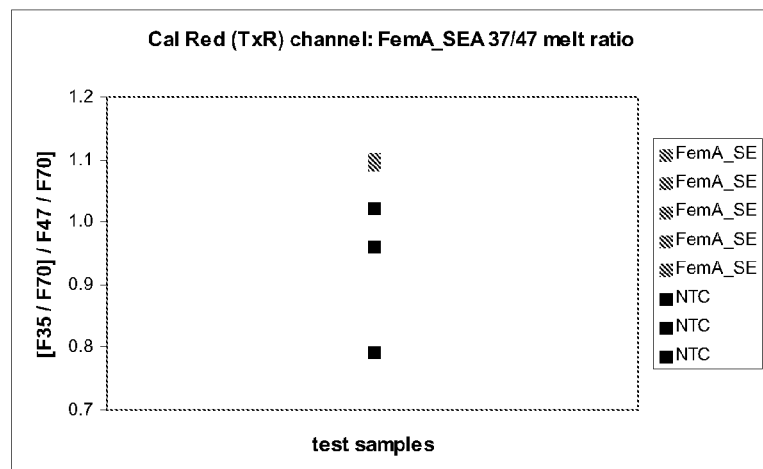
Figure 13:
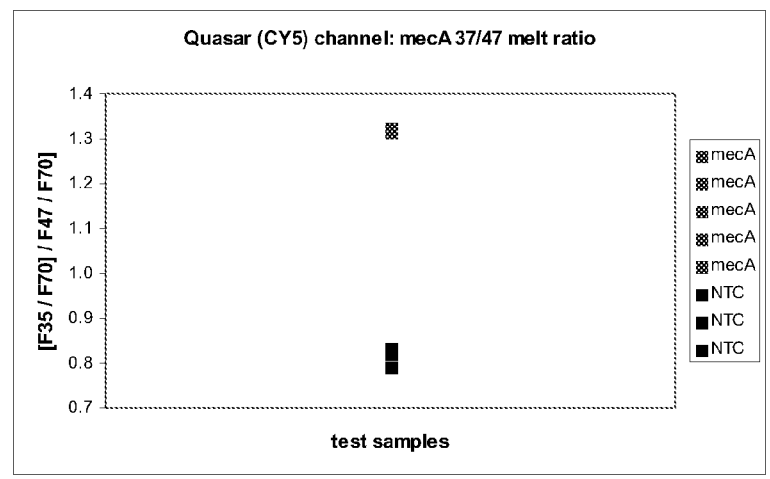

Similar to the anneal curve method, melt curve detection is performed to help optimize the end-point detection method/algorithm. The melt curve method also allows detection of products (potentially non-specific) which may be formed during PCR. The melt raw fluorescence data is shown in FIGS. 11A-C, the normalized melt melt fluorescence data to 70° C. is shown in FIG. 12A-C, and the calculated calculated melt ratios (double ratios): [F35/F70]/F47/F70], are shown in FIG. 13A-C.

EXEMPLARY ASSAYS

Exemplary MRSA 1 Assays

Figure 14:
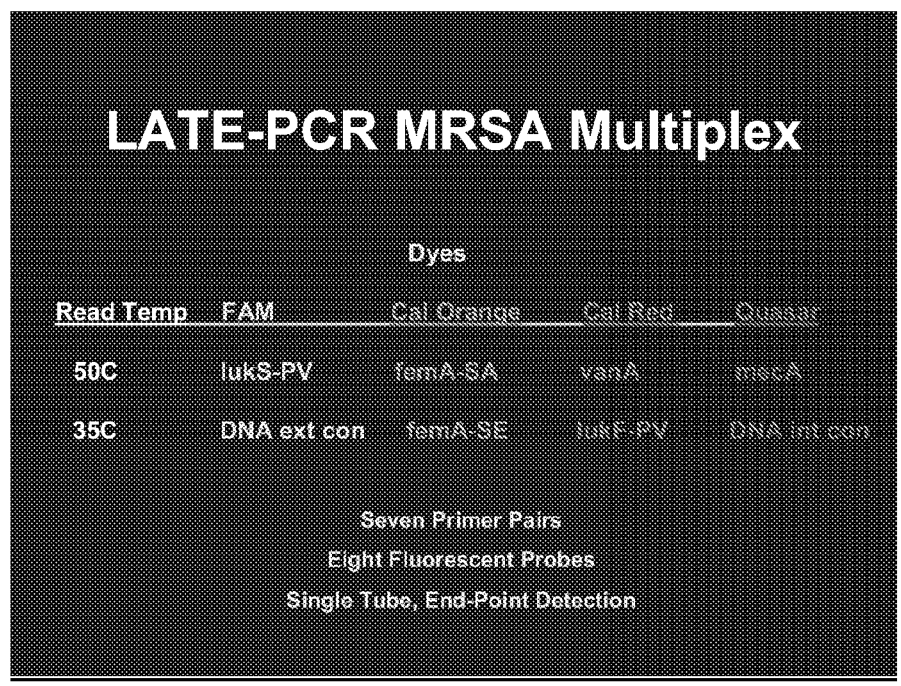
FIG. 14 shows an exemplary "MRSA 1" type assay configuration.

The MRSA 1 multiplex assay employs all of the components except for the SCCmec cassettes. In this assay both PVL toxin genes are incorporated, lukS/F. The femA-SA/SE genes are also read in the same Cal Org channel at different probe $T_M$'s. Also, two controls are incorporated into the assay. The full assay is shown in FIG. 14.

Figure 15A:
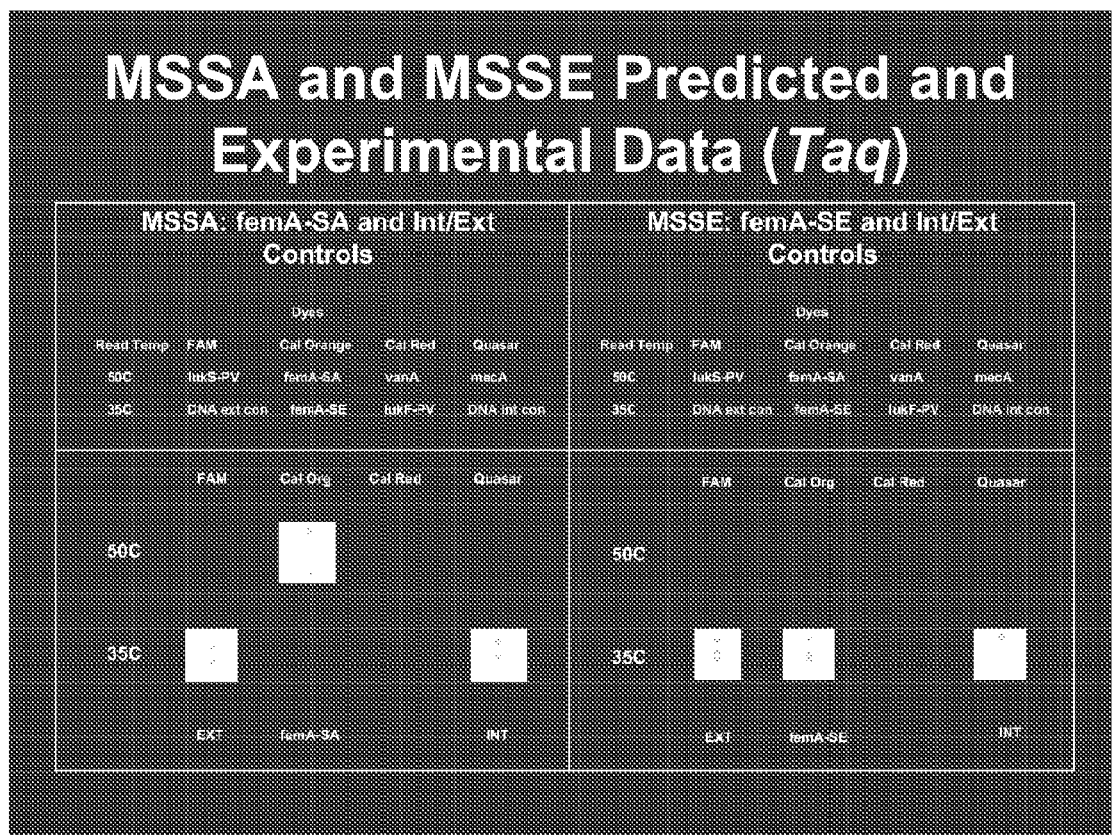
FIG. 15A shows full LATE-PCR multiplex results for MSSA and MSSE targets, showing only correct predicted results.
Figure 15B:
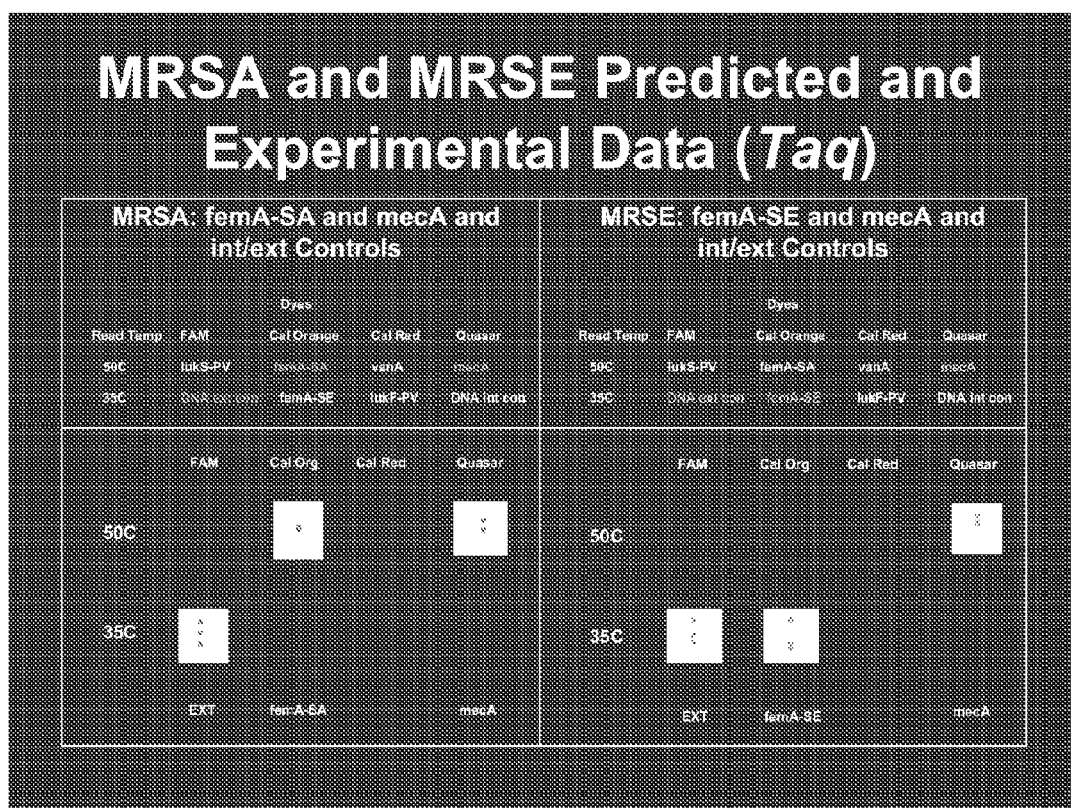
FIG. 15B shows full LATE-PCR multiplex results for MRSA and MRSE targets, showing only correct predicted results.
Figure 15C:
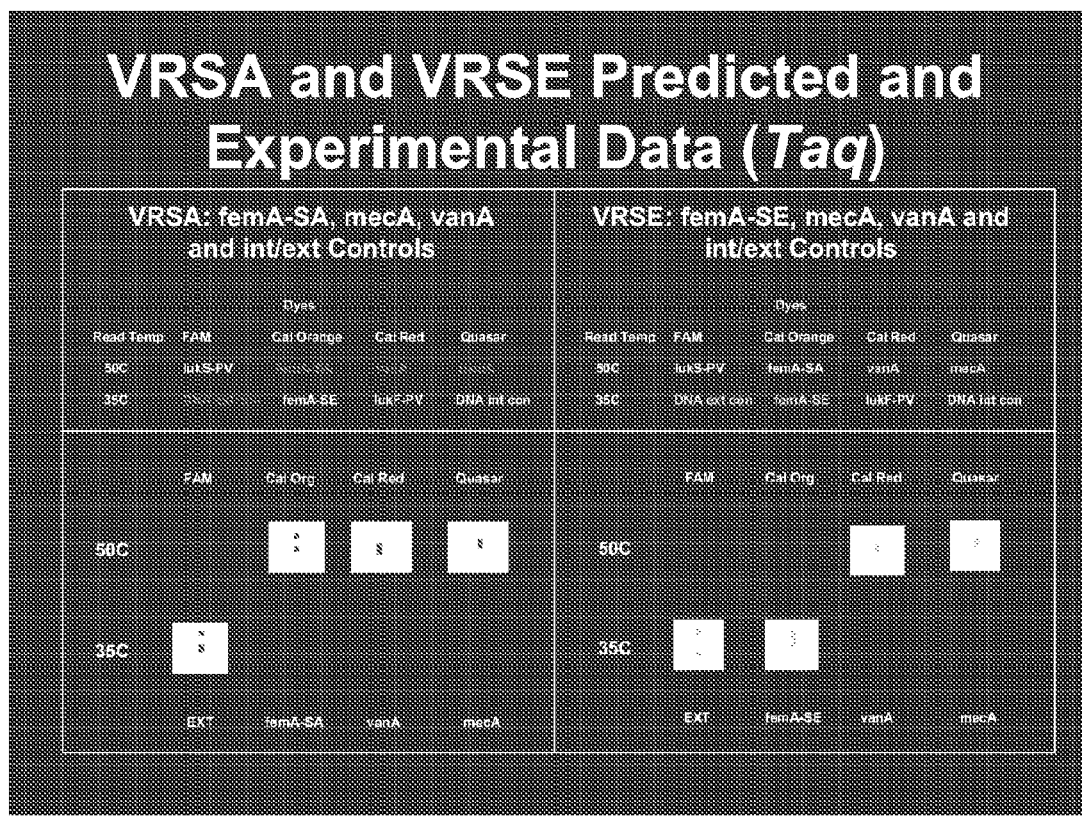
FIG. 15C shows full LATE-PCR multiplex results for VRSA and VRSE targets, showing only correct predicted results.
Figure 15D:
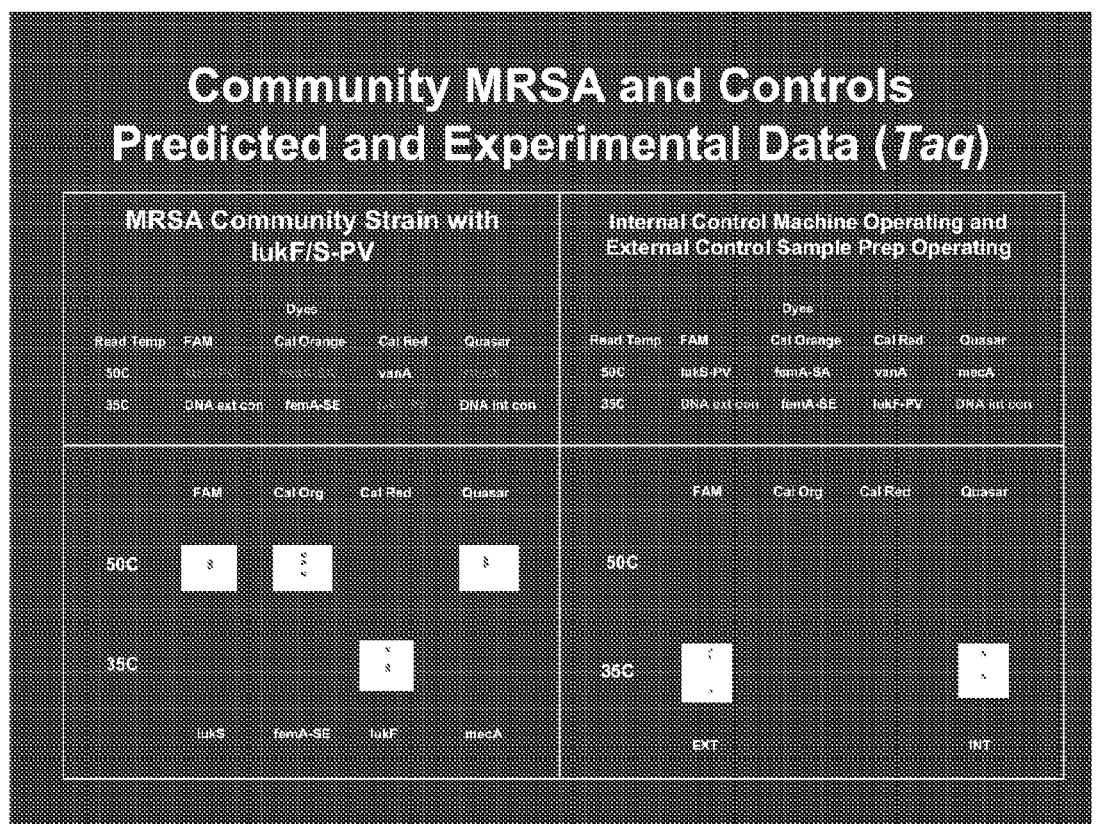
FIG. 15D shows full LATE-PCR multiplex results for CA-MRSA and control targets, showing only correct predicted results.

One example of the MRSA 1 assay is as follows. Using Pt Taq and 300 nM of Primesafe #2, and the MRSA eight-plex, LATE-PCR at endpoint is performed with the addition of the internal and external controls. All targets are detected. FIG. 15 A-D show exemplary experimental results. Each panel shows the results of the detecting specific bacteria. It is noted that the Cal Org channel is not performing properly on the Bio-Rad machine where background at low temperature drops below zero. It is believed that Pt Taq may cut the Cal Org probes and cause fluorescence in background that the machine cannot adequately handle. Signals shown are those above background after normalization and dye background subtraction. The top panel of each figure reflects the predicted result and the bottom panel shows the exemplary experimental result. FIG. 15A shows full LATE-PCR multiplex results for MSSA and MSSE targets, showing only correct predicted results. FIG. 15B shows full LATE-PCR multiplex results for MRSA and MRSE targets, showing only correct predicted results. FIG. 15C shows full LATE-PCR multiplex results for VRSA and VRSE targets, showing only correct predicted results. FIG. 15D shows full LATE-PCR multiplex results for CA-MRSA and control targets, showing only correct predicted results.

Figure 16A:
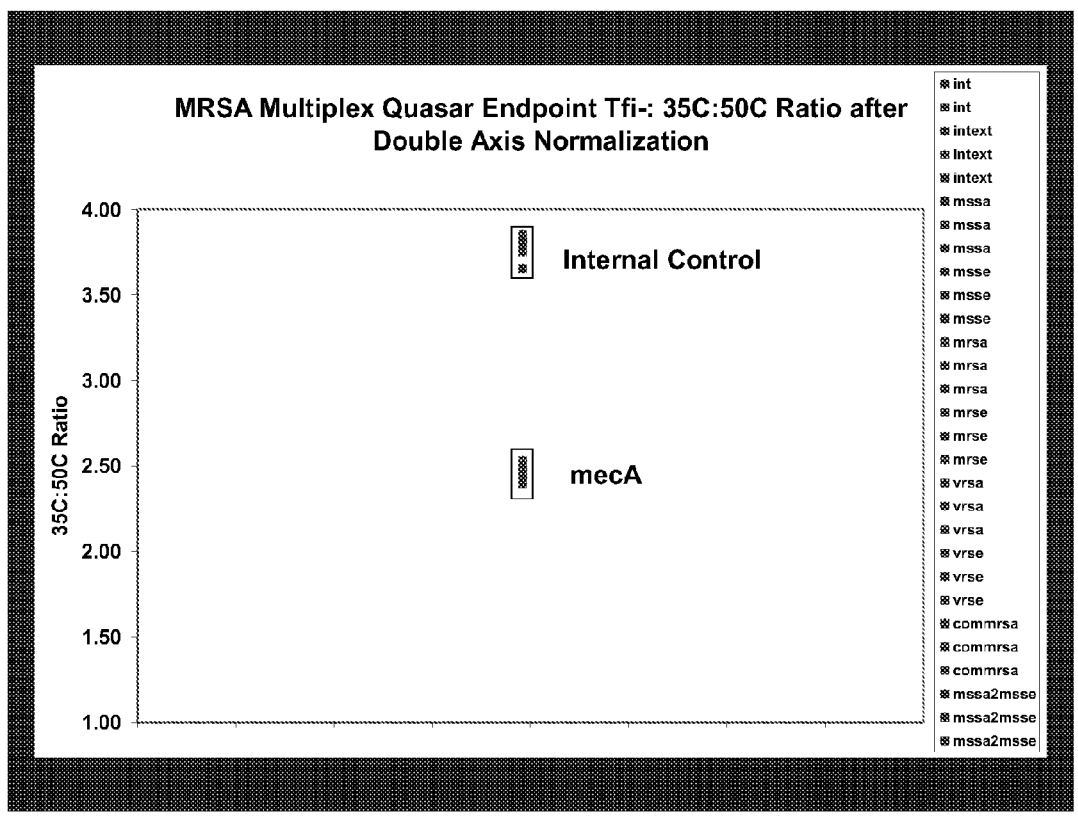
FIG. 16 shows results from an exemplary MRSA type 1 assay from Example 1. Full LATE-PCR multiplex endpoint ratio fluorescence showing internal control and mecA targets in shown in FIG. 16A. Full LATE-PCR multiplex endpoint ratio fluorescence showing lukF-PVL and vanA targets is shown in FIG. 16B. Full LATE-PCR multiplex endpoint ratio fluorescence showing femA-SA and femA-SE targets is shown in FIG. 16C. Full LATE-PCR multiplex endpoint ratio fluorescence showing external control and lukS-PVL targets is shown in FIG. 16D.
Figure 16B:
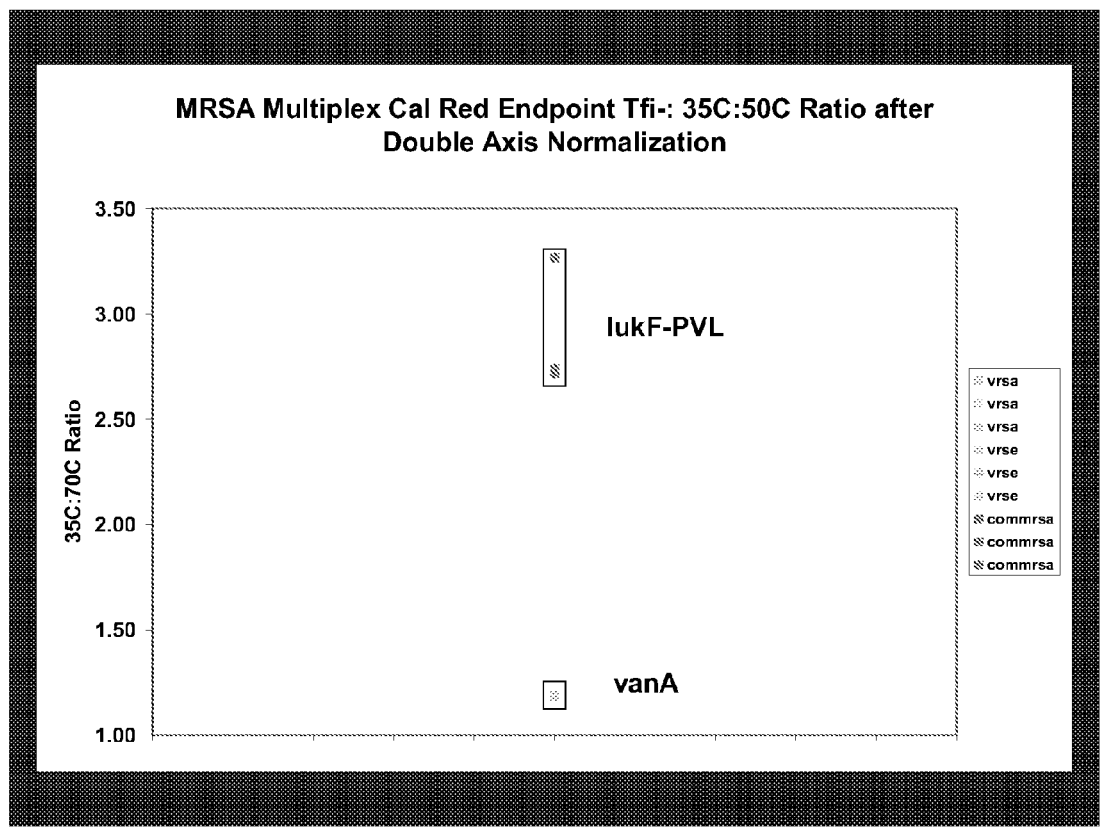
Figure 16C:
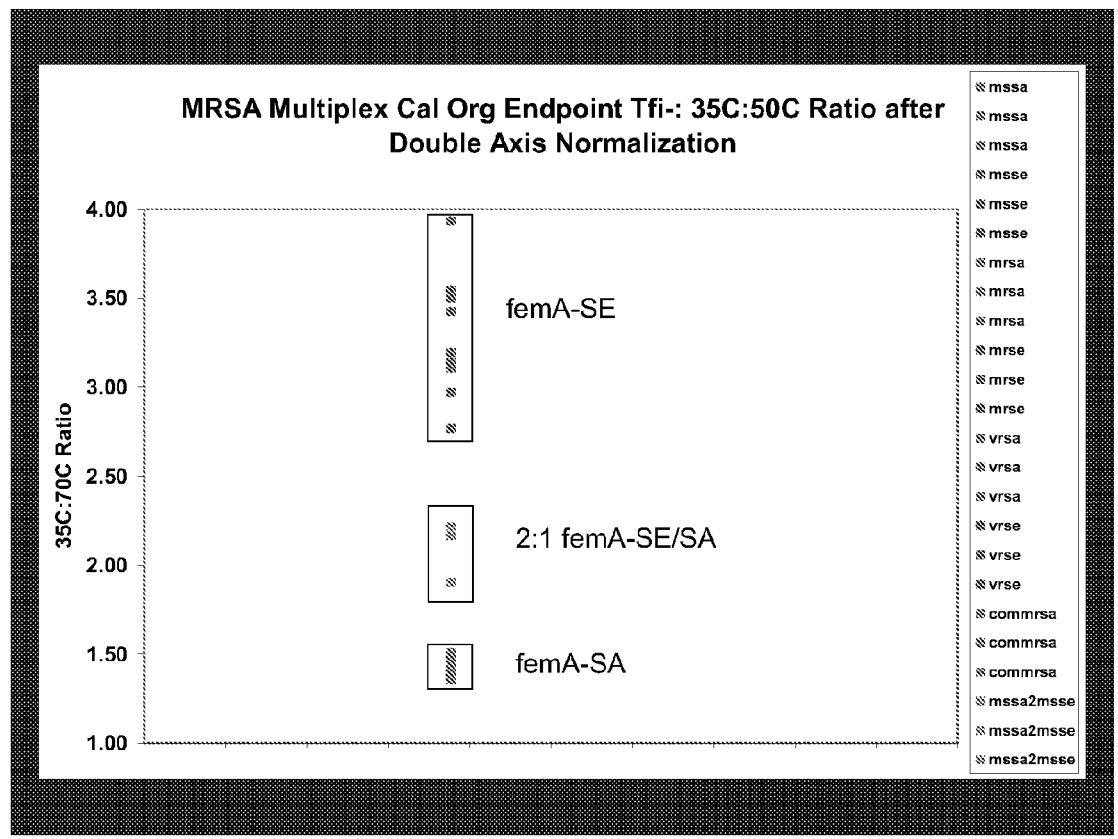
Figure 16D:
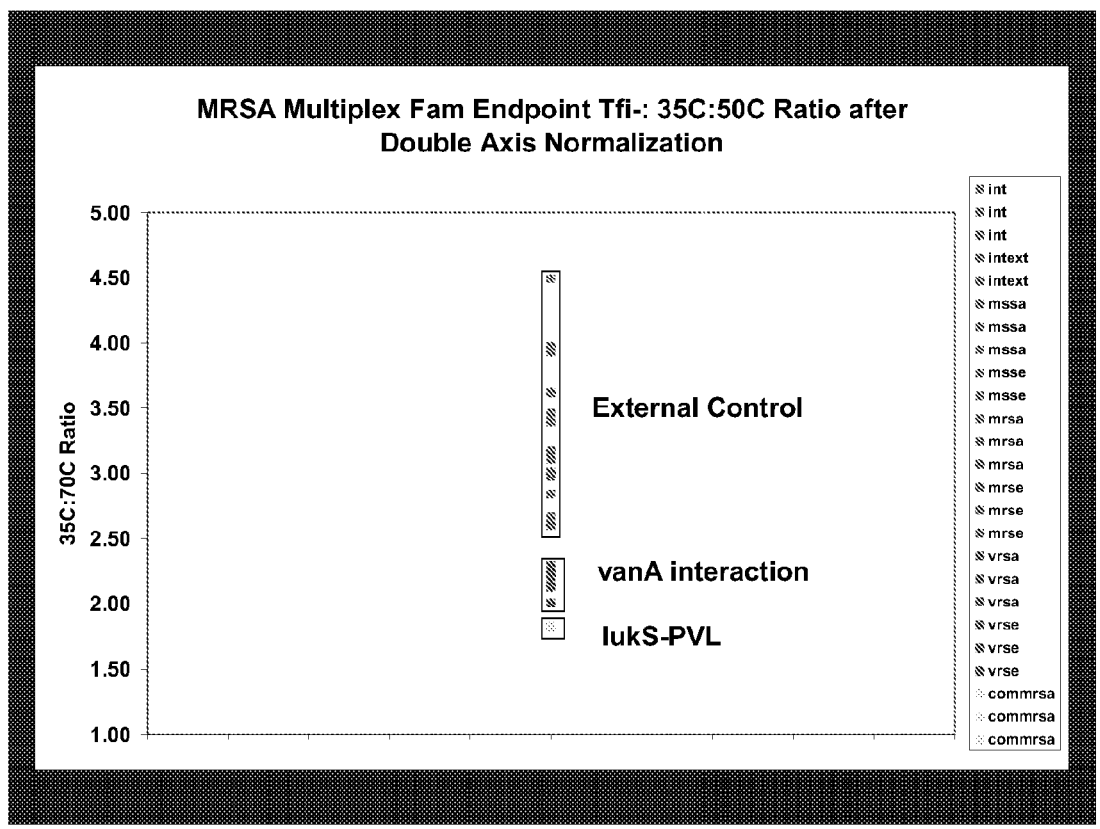

A second example of the MRSA assay is as follows. Using Tfi-, a full 8 plex can be run challenging the system with MSSA, MSSE, MRSA, MRSE, VRSA, VRSE, CA-MRSA, internal control, external and internal control, and 1:2 MSSA/MSSE. Three thousand (3,000) copies of each target, and 2 u Tfi- and 100 nm Primesafe 1, can be employed and annealed at 58° C. and extended at 68° C., with 100 nm probes. All targets are detected as shown in FIG. 16A-D. Fam channel shows some false positives from vanA which could be bleed through. Full LATE-PCR multiplex endpoint ratio fluorescence showing internal control and mecA targets in shown in FIG. 16A. Full LATE-PCR multiplex endpoint ratio fluorescence showing lukF-PVL and vanA targets is shown in FIG. 16B. Full LATE-PCR multiplex endpoint ratio fluorescence showing femA-SA and femA-SE targets is shown in FIG. 16C. Full LATE-PCR multiplex endpoint ratio fluorescence showing external control and lukS-PVL targets is shown in FIG. 16D.

Exemplary MRSA 2 Assays

Figure 17:
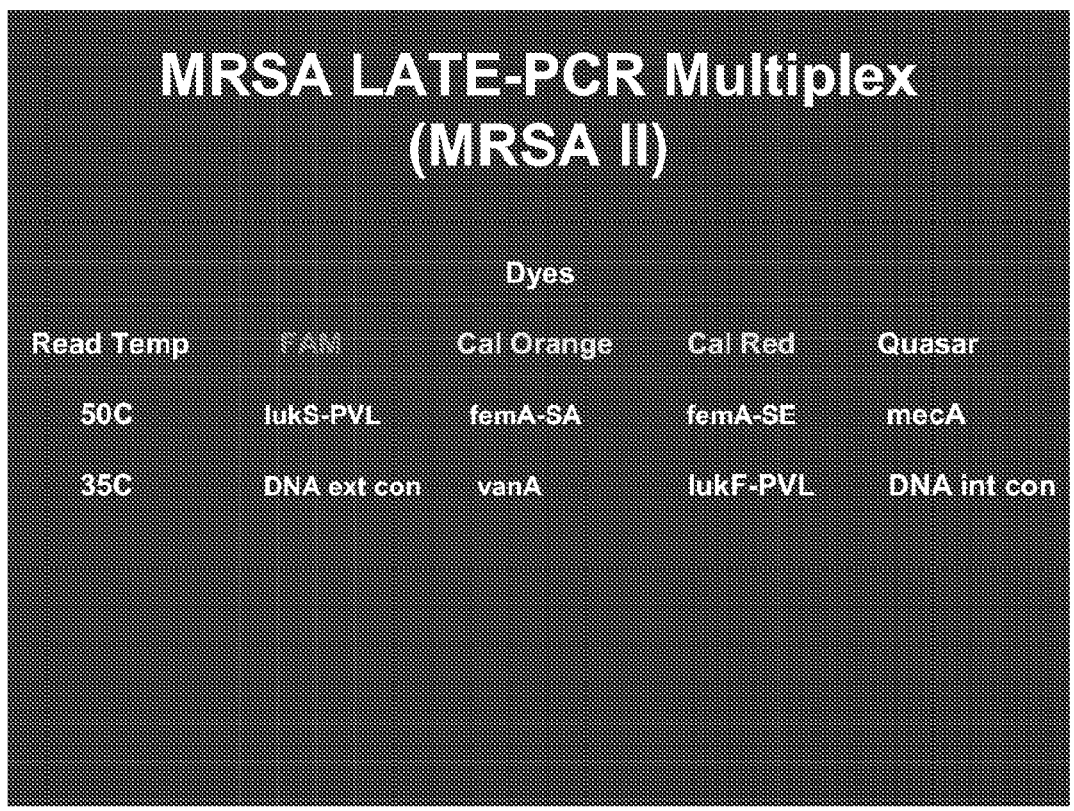
FIG. 17 shows an exemplary "MRSA 2" type assay configuration.

The MRSA 2 LATE-PCR multiplex assay makes one change in that the femA-SA and femA-SE are now separately read in Cal Org and Cal Red. The vanA is now read in the low temperature part of Cal Org. These changes allow the assay to be more quantitative for femA-SA and femA-SE. FIG. 17 shows the general details for MRSA 2 assays.

Figure 18A:
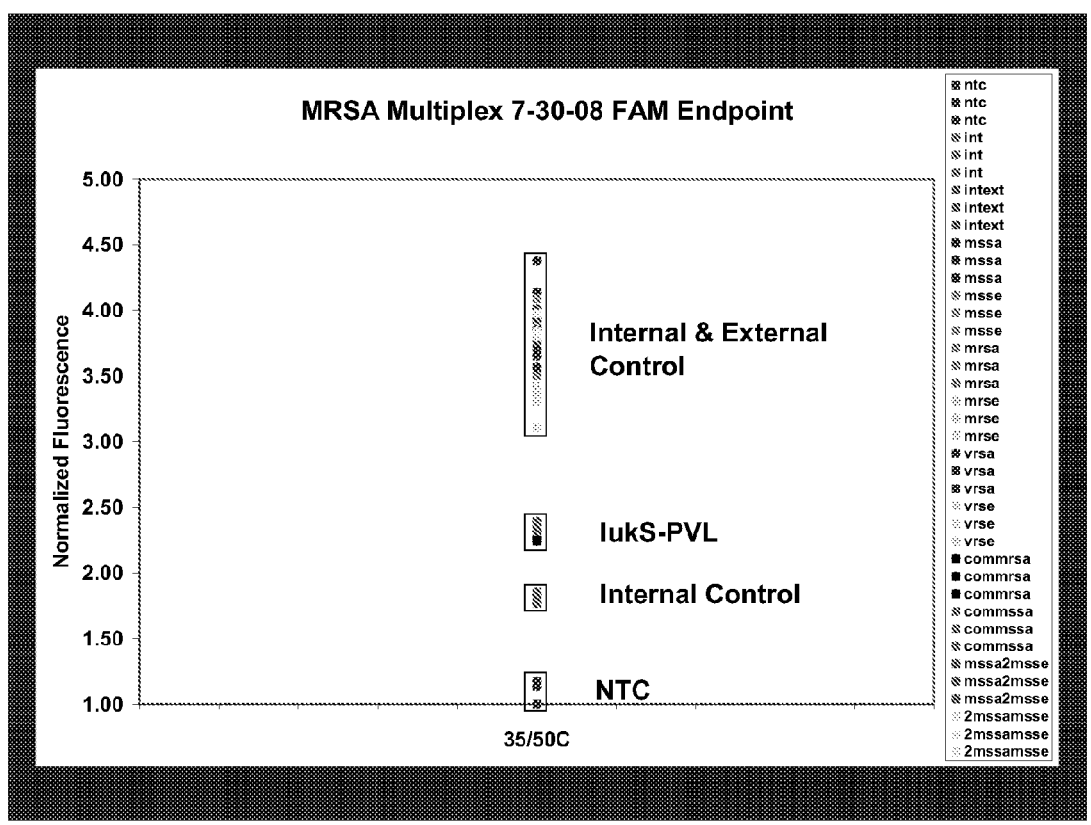
FIG. 18 shows results from an exemplary MRSA type 2 assay from Example 1. Full LATE-PCR multiplex endpoint ratio fluorescence showing controls and lukS-PVL targets is shown in FIG. 18A. Full LATE-PCR multiplex endpoint ratio fluorescence showing femA-SA and vanA targets is shown in FIG. 18B. Full LATE-PCR multiplex endpoint ratio fluorescence showing lukF-PVL and femA-SE targets is shown in FIG. 18C. Full LATE-PCR multiplex endpoint ratio fluorescence showing internal control and mecA targets is shown in FIG. 18D.
Figure 18B:
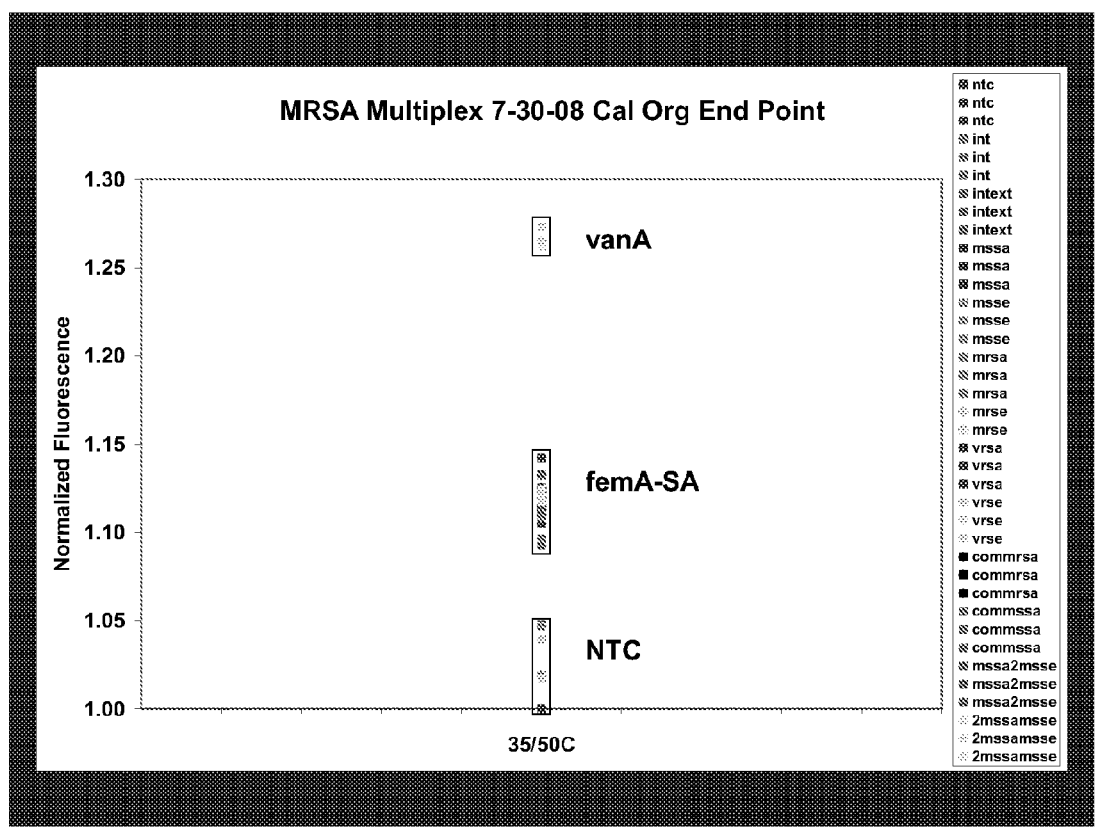
Figure 18C:
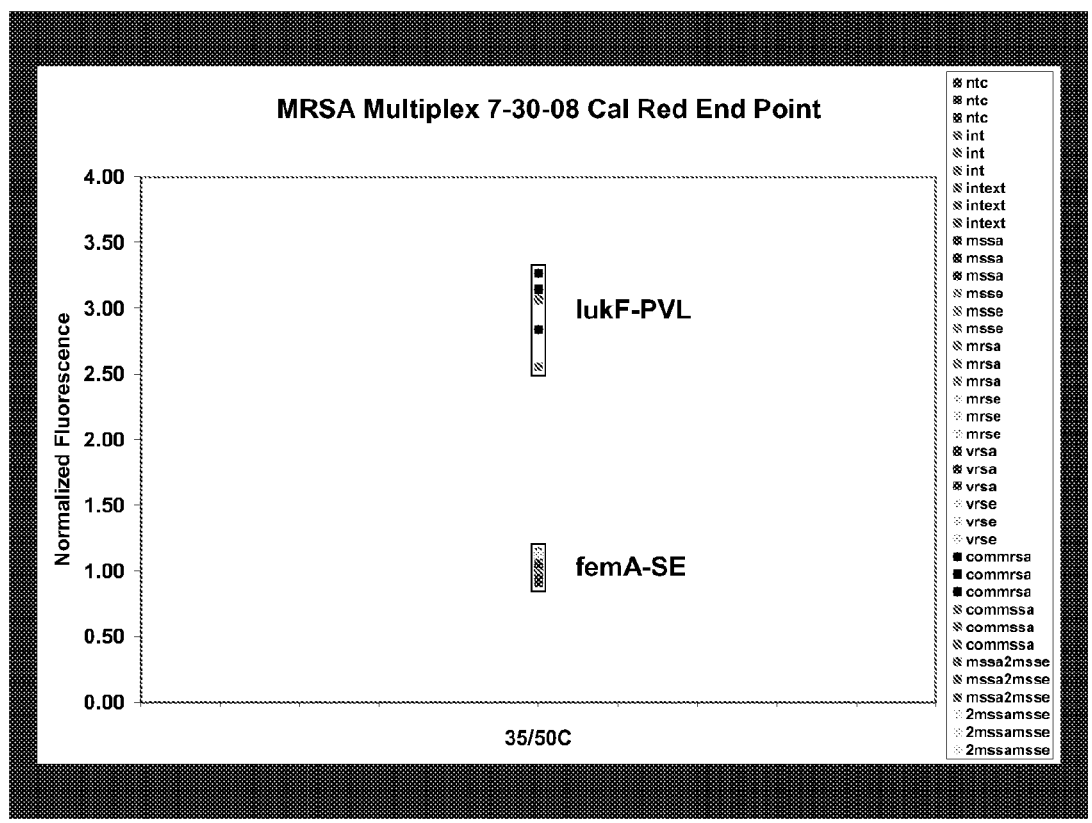
Figure 18D:
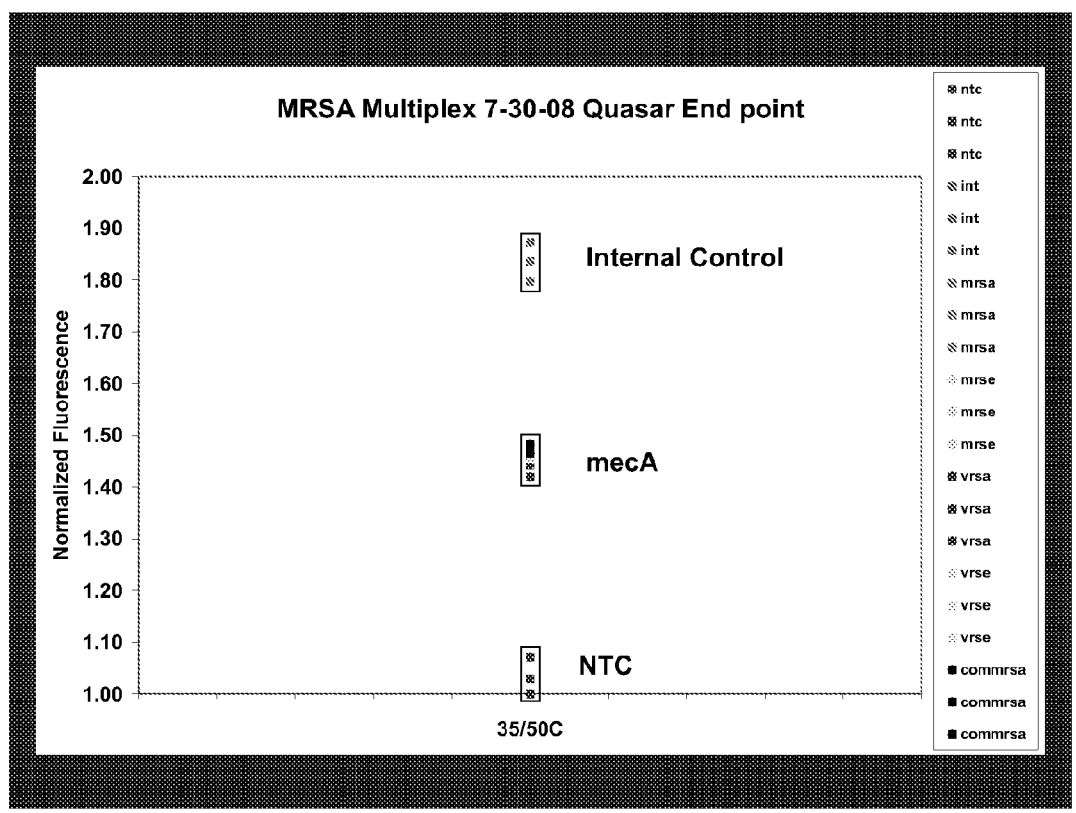

One example of the MRSA 2 assays is as follows. Full MRSA 2 multiplex is run using 3,000 copies of all targets and 100 nm of each probe with 600 nm of LDL22 and 300 nm of 4D22. Results are shown in FIG. 18 A-D. In the FAM channel, the lukS is strong. The internal control is strong, and is stronger in signal when the external control was added. In the Cal Org channel the femA-SA all are strong, but still some scatter in raw intensities even though the ratios are extremely tight. New vanA 2 primers and probe used. In the Cal Red channel the femA-SE is very strong, much tighter and ratios very tight. The lukF is strong for all samples for the first time. In the Quasar channel the mecA is strong, very tight and the ratios extremely tight. The external control is not present. No false positives are present. All analyses are done on melt data only. Full LATE-PCR multiplex endpoint ratio fluorescence showing controls and lukS-PVL targets is shown in FIG. 18A. Full LATE-PCR multiplex endpoint ratio fluorescence showing femA-SA and vanA targets is shown in FIG. 18B. Full LATE-PCR multiplex endpoint ratio fluorescence showing lukF-PVL and femA-SE targets is shown in FIG. 18C. Full LATE-PCR multiplex endpoint ratio fluorescence showing internal control and mecA targets is shown in FIG. 18D.

Exemplary MRSA 3 Assays

Figure 19:
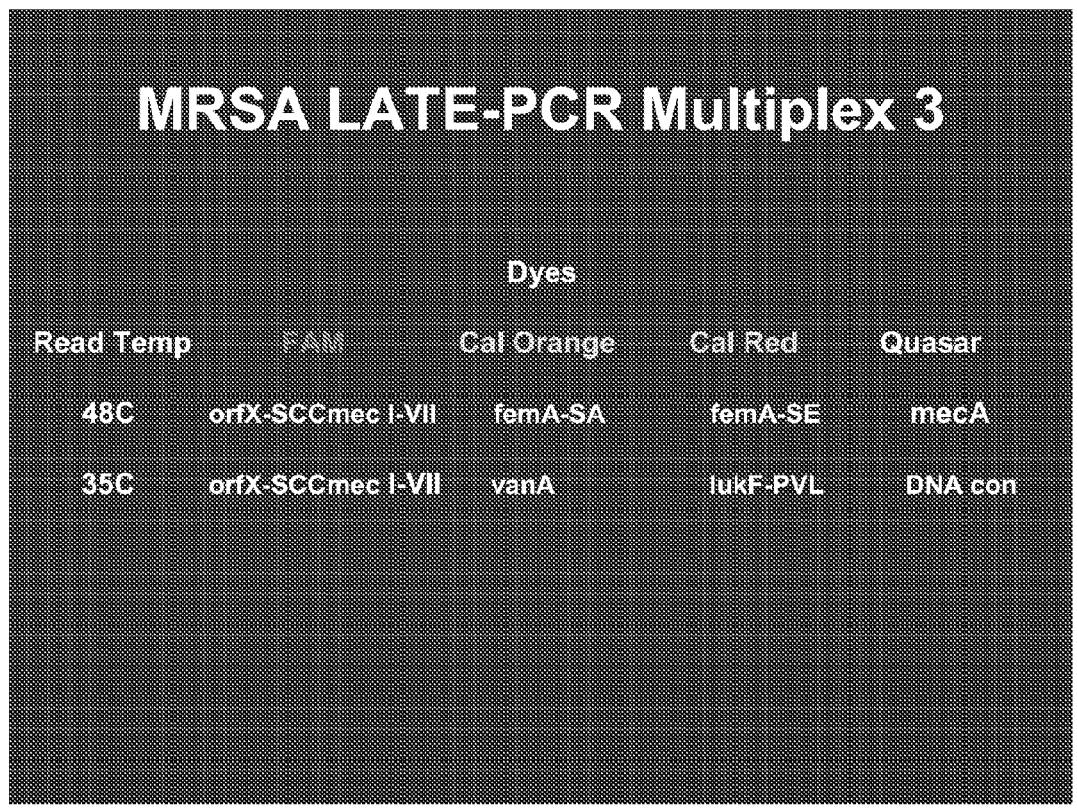
FIG. 19 shows an exemplary "MRSA 3" type assay configuration.

The MRSA 3 assays relates to the detection of SCCmec cassettes at orfX boundary. These assays use three limiting primers (see Material and Methods above) that are not all perfect matches to the SCCmec cassette and an excess primer and FAM probe in the orfX that are highly conserved to detect cassettes I-VII. The multiplex version of these assays that involves detecting the other genes discussed above is shown in FIG. 19, with the SCCmec cassettes incorporated into the FAM channel. Except for the addition of the SCCmec detection and the loss of the FAM control, the assay is generally the same as MRSA 2 assays.

Figure 20K:
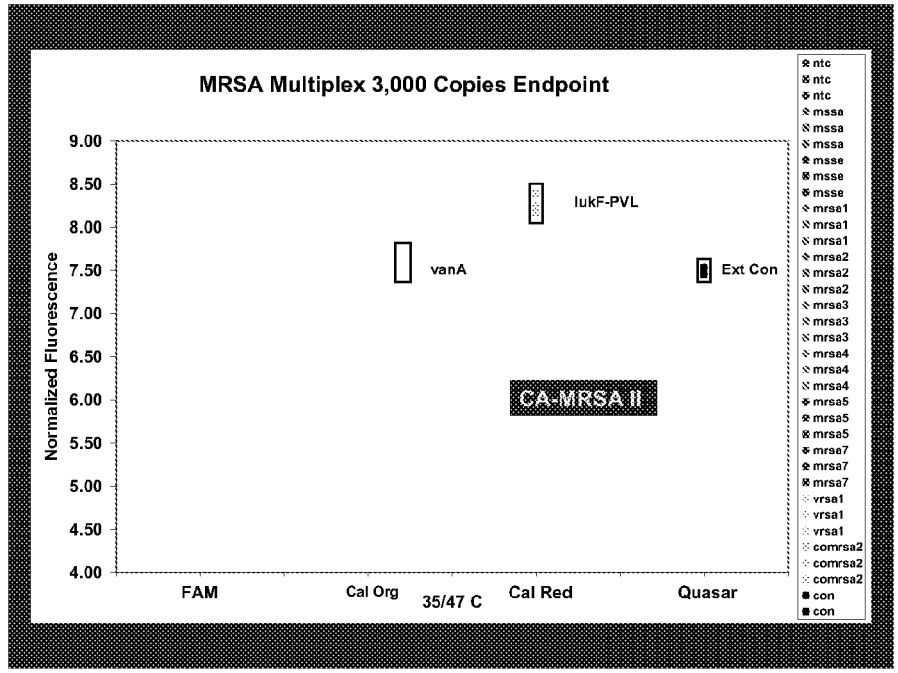
FIG. 20K shows full LATE-PCR multiplex endpoint ratio fluorescence showing CA-MRSA2 target.

One example of the MRSA 3 assays is as follows. This assay is challenged with MSSA, MSSE, MRSA I-VII, VRSA I, CA-MRSA II, and external control, using 600 nM of 4D22. Results are shown in FIG. 30 A-K. All SCCmec are detected, as well as femA-SA, femA-SE, luF-PVL, and mecA. The control signal was very weak, and the vanA signal does appear on top of the femA for the VRSA sample (vanA2 probe). FIG. 20A shows full LATE-PCR multiplex endpoint ratio fluorescence showing control targets. FIG. 20B shows full LATE-PCR multiplex endpoint ratio fluorescence showing MSSA target. FIG. 20C shows full LATE-PCR multiplex endpoint ratio fluorescence showing MSSE target. FIG. 20D shows full LATE-PCR multiplex endpoint ratio fluorescence showing HA-MRSA1 target. FIG. 20E shows full LATE-PCR multiplex endpoint ratio fluorescence showing HA-MRSA2 target. FIG. 20F shows full LATE-PCR multiplex endpoint ratio fluorescence showing HA-MRSA3 target. FIG. 20G shows full LATE-PCR multiplex endpoint ratio fluorescence showing HA-MRSA4 target. FIG. 20H shows full LATE-PCR multiplex endpoint ratio fluorescence showing HA-MRSA5 target. FIG. 20I shows full LATE-PCR multiplex endpoint ratio fluorescence showing HA-MRSA7 target. FIG. 20J shows full LATE-PCR multiplex endpoint ratio fluorescence showing CA-MRSA2 target. FIG. 20K shows full LATE-PCR multiplex endpoint ratio fluorescence showing CA-MRSA2 target.

Figure 21E:
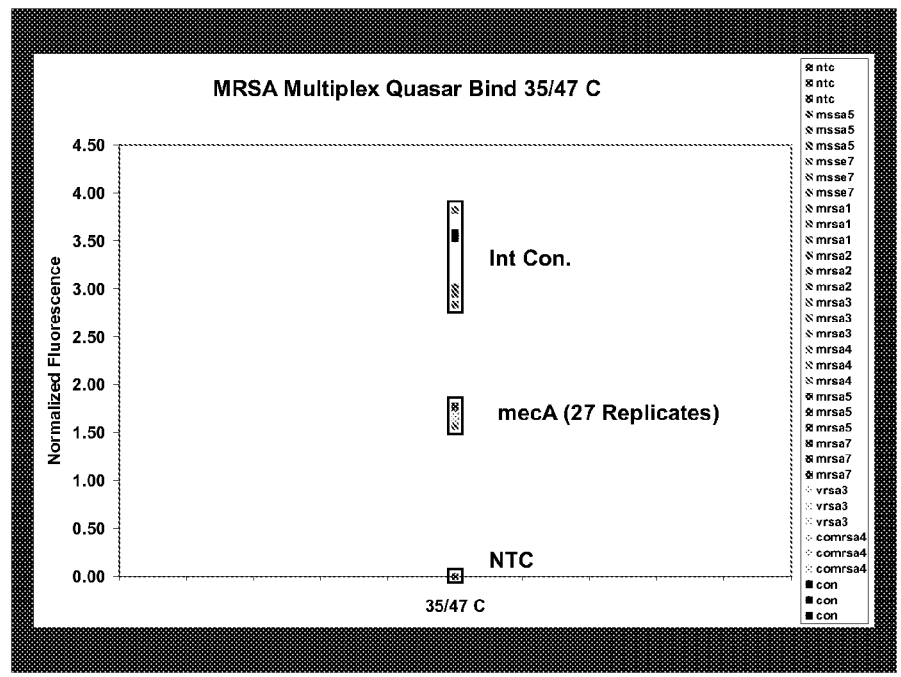
FIG. 21E shows full LATE-PCR multiplex endpoint ratios fluorescence showing internal control and mecA targets.

A second example of the MRSA 3 types assays is as follows. Full MRSA multiplex run may be challenged with NTC, MSSAV, MSSEVII, MRSA I, II, III, IV, V, VII, VRSAIII, CA-MRSAIV and internal control. Every signal is strong as shown in FIG. 21 A-F. FAM channel shows all SCCmec cassettes with some distortion due to SCCmec probe binding to an internal control target. SCCmec II, IV, III-VII, I-V are very distinctive on FAM bind and can be further defined on FAM melt using different ratios. Cal Org shows all femA-SA to have tight ratios and clear strong signal for VRSAIII. CalRed shows strong signal for femA-SE and lukF-PVL. Quasar shows that the internal control probe also binds to the femA at low temperature where strong signal observed for control only and weaker for all other signals as a contribution of control probe signal. All mecA signals are strong and specific. Data are also displayed calculating multiple end point ratios at 30/50 C, 30/45 C, and 30/40 C that will rigidly define the specific SCCmec product found in the reaction within the FAM channel detection. FIG. 21A shows full LATE-PCR multiplex at 3 endpoint ratios fluorescence showing SCCmec cassette targets. FIG. 21B shows full LATE-PCR multiplex at 3 endpoint ratios fluorescence showing SCCmec cassette targets. FIG. 21C shows Full LATE-PCR multiplex endpoint ratios fluorescence showing vanA and femA-SA targets. FIG. 21D shows full LATE-PCR multiplex endpoint ratios fluorescence showing lukF-PVL and femA-SE targets. FIG. 21E shows full LATE-PCR multiplex endpoint ratios fluorescence showing internal control and mecA targets.

As shown above, the MRSA 3 LATE-PCR multiplex assays run well for each targeted gene against all challenges and shows high selectivity and sensitivity. The Easyplex 4D22 at 600 nM cleans up reactions and allows dilution series from $10^8$ to 1 target. All SCCmec cassettes are distinguishable at endpoint bind/melt ratio analysis. One exemplary method is to use endpoint bind data, normalized to 60 C for SCCmec and 65 C for other dye channels, then subtract out background dye fluorescence. At this point data that are significantly above a background limit can be called as a positive result and will provide sensitivity of the assay. Then data are normalized at ratios of 30/50 C, 30/45 C and 30/40 C for maximum discrimination and selectivity. Each specific target (femA-SA and vanA) will have a discreet ratio that is independent of concentration in specific dye channel.

Exemplary MRSA 4 Assay

Figure 22:
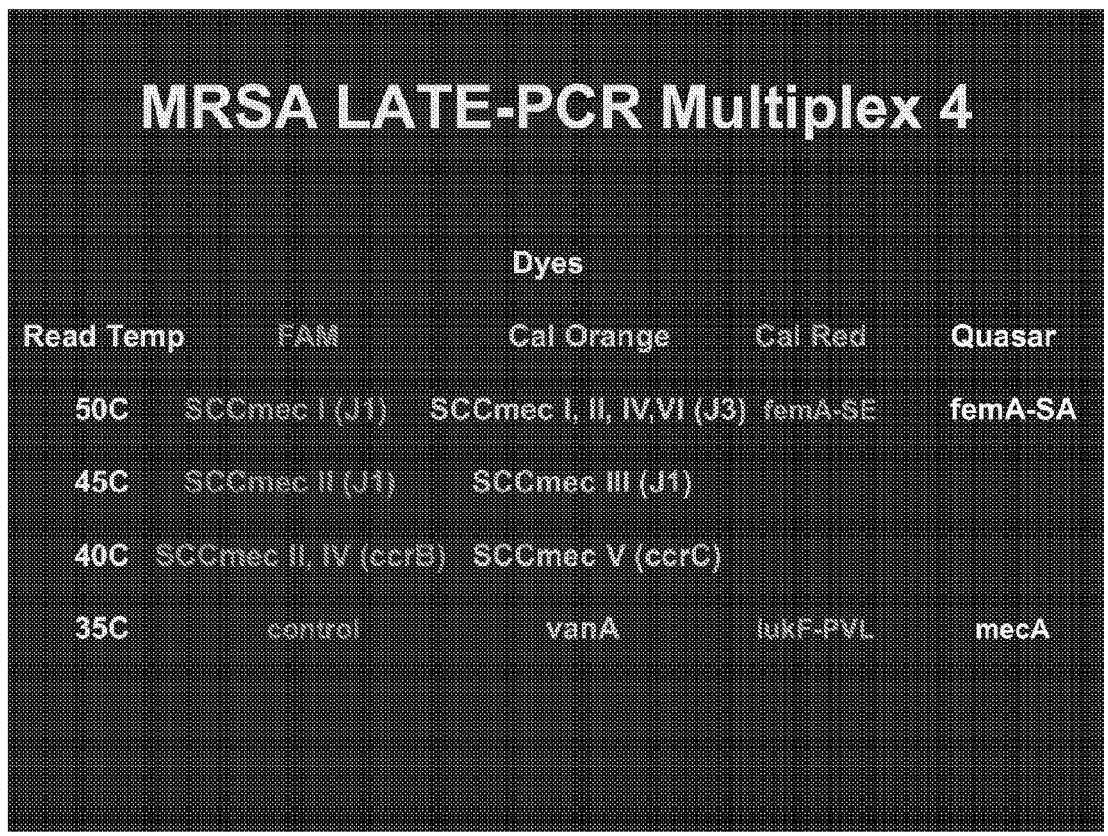
FIG. 22 shows an exemplary "MRSA 4" type assay configuration.

An additional assay configuration is the one shown in FIG. 22. Such an assay can be run as described above for the other MRSA assays and endpoint read at the temperatures indicated in FIG. 22.

All publications and patents mentioned in the present application are herein incorporated by reference in their entireties. Various modification and variation of the described methods and compositions will be apparent to those skilled in the art without departing from the scope and spirit of the assays described herein. Although the methods, compositions, and kits have been described in connection with specific exemplary embodiments, it should be understood that the claims are not limited to these specific embodiments. Indeed, various modifications of the described modes for carrying out the assays described herein are intended to be within the scope of the following claims.

We claim:

1. A method for identifying the presence of a polymorphic target sequence variant, comprising:
   (a) combining a sample suspected of containing a first or second variant of a polymorphic target sequence with a labeled probe, one excess reverse primer, and two or more limiting forward primers to generate a combined sample, wherein the limiting forward primers are not perfect matches to the target sequence;
   (b) treating the combined sample under amplification conditions such that a single stranded amplicon is generated, wherein the single-stranded amplicon comprises:
      (i) the first or second variant of the polymorphic target sequence, and
      (ii) a probe hybridization sequence, wherein the probe hybridization sequence is identical among different polymorphic target sequence variants and does not overlap the polymorphic target sequence;
   (c) detecting signal from the labeled probe at two temperatures;
   (d) calculating an experimental signal ratio of the signal at the two temperatures; and
   (e) comparing the experimental signal ratio with known signal ratios for the first and second variants of the polymorphic sequence, wherein a match between the experimental signal ratio and the known signal ratio for the first or second variant of the polymorphic sequence identifies the presence of said first or second variant.

2. The method of claim 1, wherein said excess reverse primer is added to said combined sample at a concentration at least five-times that of each of said two or more limiting forward primers, and wherein said amplification conditions comprise asymmetric PCR conditions.

3. The method of claim 1, wherein a single-stranded amplicon comprising the first polymorphic target sequence is generated in an amount that is at least 10-fold greater than a single-stranded amplicon comprising the second polymorphic target sequence, and wherein there is a match between said experimental signal ratio and the known signal ratio for the first variant of the polymorphic sequence, thereby identifying the presence of said first variant of the polymorphic sequence in the sample.

4. The method of claim 1, wherein a single-stranded amplicon comprising the second polymorphic target sequence is generated in an amount that is at least 10-fold greater than a single-stranded amplicon comprising the first polymorphic target sequence, and wherein there is a match between said experimental signal ratio and said the known signal ratio for the second variant of the polymorphic sequence, thereby identifying the presence of said second variant of the polymorphic sequence in the sample.

* * * * *